US011332750B2

(12) United States Patent
Mojzita et al.

(10) Patent No.: US 11,332,750 B2
(45) Date of Patent: May 17, 2022

(54) EXPRESSION SYSTEM FOR EUKARYOTIC ORGANISMS

(71) Applicant: Teknologian tutkimuskeskus VTT Oy, Espoo (FI)

(72) Inventors: Dominik Mojzita, Vtt (FI); Anssi Rantasalo, Vtt (FI); Jussi Jäntti, Vtt (FI); Christopher Landowski, Vtt (FI); Joosu Kuivanen, Vtt (FI)

(73) Assignee: Teknologian Tutkimuskeskus VTT OY, Espoo (FI)

( * ) Notice: Subject to any disclaimer, the term of this patent is extended or adjusted under 35 U.S.C. 154(b) by 0 days.

(21) Appl. No.: 15/737,696

(22) PCT Filed: Feb. 21, 2017

(86) PCT No.: PCT/FI2017/050114
§ 371 (c)(1),
(2) Date: Dec. 18, 2017

(87) PCT Pub. No.: WO2017/144777
PCT Pub. Date: Aug. 31, 2017

(65) Prior Publication Data
US 2018/0371468 A1 Dec. 27, 2018

(30) Foreign Application Priority Data

Feb. 22, 2016 (FI) .................... 20165137

(51) Int. Cl.
| | |
|---|---|
| *A61K 48/00* | (2006.01) |
| *C12N 15/79* | (2006.01) |
| *C07H 21/04* | (2006.01) |
| *C12P 21/06* | (2006.01) |
| *C12N 15/62* | (2006.01) |

(52) U.S. Cl.
CPC ........... *C12N 15/79* (2013.01); *C12N 15/625* (2013.01); *C07H 21/04* (2013.01); *C07K 2319/09* (2013.01); *C12N 2310/122* (2013.01); *C12N 2310/531* (2013.01); *C12N 2510/00* (2013.01)

(58) Field of Classification Search
CPC .. C12N 15/79; C12N 15/625; C12N 2510/00; C07H 21/04; C12P 21/06
USPC .......... 424/93.21; 435/320.1; 536/23.1, 23.5, 536/24.1
See application file for complete search history.

(56) References Cited

U.S. PATENT DOCUMENTS

2002/0081667 A1    6/2002  Gorlach et al.

OTHER PUBLICATIONS

Anssi Rantasalo et al.: "Synthetic Transcription Amplifier System for Orthogonal Control of Gene Expression in *Saccharomyces cerevisiae*", Plos One, vol. 11, No. 2, Feb. 22, 2016 (Feb. 22, 2016), p. e0148320 (Year: 2016).*
Yoichiro Ito et al.: "A Highly Tunable System for the Simultaneous Expression of Multiple Enzymes in *Saccharomyces cerevisiae*", ACS Synthetic Biology, vol. 4, No. 1, Jan. 16, 2015 (Jan. 16, 2015), pp. 12-16 (Year: 2015).*
Kadonaga et al. (2012, Wily Interdisip. Rev. Biol., vol. 1(1), pp. 40-51) (Year: 2012).*
Ito et al. (May 1, 2014, ACS Synthetic Biology, vol. 4, pp. 12-16). (Year: 2014).*
Liu et al., 2016, electronic publication date Oct. 31, 2015, Current Opinion in Biotechnology, vol. 37, pp. 36-44.*
Blount Benjamin et al; Construction of synthetic regulatory networks in yeast, FEBS Letters 586 (2012) p. 2112-2121.
Ito Yoichiro et al; A Highly Tunable System for the Simualtaneous Expression of Multiple Enzymes in *Saccharomyces cerevisiae*, ACS Publications, Synthetic Biology, 2015, 4, p. 12-16.
Vogl Thomas et al.; Synthetic Core Promoters for Pichia pastoris, ACS Synthetic Biology, Mar. 2014, p. 188-191.
Redden Heidi et al; The development and characterization of synthetic minimal yeast promoters, Nature Communications, Jul. 2015.
Rantasalo Anssi et. al; Synthetic Transcription Amplifier System for Orthogonal Control of Gene Expression in *Saccharomyces cerevisiae*; Plos One, Feb. 22, 2016.
Pachlinger Robert et. al; Metabolically Independent and Accurately Adjustable *Asppergillus* sp. Expression system Applied and Environmental Microbiology Feb. 2005, p. 672-678.
Purcell Oliver et al; Rule-Based Design of Synthetic Transcription Factors in Eukaryotes; ACS Synthetic Biology, 2014 vol. 3, p. 737-744.
Wusheng Liu et. al; Plant synthetic promoters and transcription factors.; Current Opinion in Biotechnology 2016, 37, p. 36-44.
Khalil Ahmad et. al; A Synthetic Biology Framework for Programming Eukaryotic Transcription Functions; Cell 150, Aug. 3, 2012, vol. 150, p. 647-658.
Curran Kathleen et al; Design of synthetic yeast promoters via tuning of nucleosome architecture; Nature Communications, May 27, 2014.
Ito Yoichiro et al; Combinatorial Screening for Transgenic Yeasts with High Cellulase Activities in Combination with a Tunable Expression System, PLoS One, Dec. 21, 2015.

(Continued)

*Primary Examiner* — Shin Lin Chen
(74) *Attorney, Agent, or Firm* — Merchant & Gould P.C.

(57) ABSTRACT

The present invention provides an expression system for a eukaryotic host, which comprises 1) an expression cassette comprising a core promoter, the core promoter controlling the expression of a DNA sequence encoding a synthetic transcription factor (sTF), and 2) one or more expression cassettes each comprising a DNA sequence encoding a desired product operably linked to a synthetic promoter, the synthetic promoter comprising a core promoter, and sTF-specific binding sites upstream of the core promoter. The present invention also provides a method for identifying universal core promoters for eukaryotic hosts, expression systems using universal core promoters, hosts comprising the systems, and methods for producing protein products in eukaryotic hosts.

9 Claims, 9 Drawing Sheets
Specification includes a Sequence Listing.

(56) References Cited

OTHER PUBLICATIONS

Hubmann Georg et al: Natural and Modified Promoters for Tailored Metabolix Engineering of the Yeast *Saccharomyces cerevisiae*, Yeast Metabolic Engineering, Methods and Protocols, Methiods in Molecular Biology, vol. 1152, 2014.

Farzadfard Fahim et. al; Tunable and Multifunctional Eukaryotic Transcription Factors Based on CRISPR/Cas ACS Synthetic Biology, 2013, 2, Aug. 26, 2013.

Brückner Kathleen et. al; A library of synthetic transcription activator-like effecktor-activated promoters for coordinated orthogonal gene expression in plants, The Plant Journal, 2015, 82, p. 707-716.

Search report of FI20165137, issued by Finnish Patent and Regisration Office dated Sep. 21, 2016.

International search report of PCT/FI2017/050114, issued by European Patent Office dated May 11, 2017.

Blumhoff Marzena et al; Six novel constitutive promoters for metabolic engineering of Aspergillus niger, Appliced Microbiology and Biotechnology, Jan. 2013, vol. 97, Issue 1, p. 259-267.

Blazeck, John et al., Promoter engineering: Recent advances in controlling transcription at the most fundamental level, Biotechnology Journal, article first published Aug. 14, 2012, pp. 46-58, vol. 8 No. 1.

* cited by examiner

EXPRESSION SYSTEM FOR EUKARYOTIC ORGANISMS

PRIORITY

This application is a U.S. national application of the international application number PCT/FI2017/50114 filed on Feb. 21, 2017 and claiming priority of Finnish national application FI20165137 filed on Feb. 22, 2016, the contents of both of which are incorporated herein by reference.

TECHNICAL FIELD

The present invention relates to an expression system for a eukaryotic host (such as a microorganism host), a host comprising said expression system, and a method for producing a desired protein product by using said host. Furthermore the present invention relates to a method for identifying a universal core promoter, a universal core promoter obtainable by said method, and an expression system, a eukaryotic organism host (such as a microorganism host) and method for producing a protein product by using a universal core promoter.

BACKGROUND

Controlled and predictable gene expression is very difficult to achieve even in well-established hosts, especially in terms of stable expression in diverse cultivation conditions or stages of growth. In addition, for many potentially interesting industrial hosts, there is a very limited (or even absent) spectrum of tools and/or methods to accomplish expression of heterologous genes. In many instances, this prohibits the use of these (often very promising hosts) in industrial applications. In some hosts, specific inducing conditions need to be in place to achieve desirable expression of target genes. This results in specific requirements for culture media or downstream processing that ultimately increase production costs. Another problem in industrial hosts is the establishment of complex expression programs where it is desired to have specific expression levels of multiple genes simultaneously. This is, for instance, important for metabolic pathway engineering, where the individual genes encoding enzymes in production pathways need to be expressed (and the corresponding enzymes produced) in balanced ratio to ensure optimal metabolic flux towards the desired products.

In order to achieve predictable and/or stable expression patterns of the target genes in a host organism (in variable conditions) it is important that the expression of these genes is minimally affected by the intrinsic regulatory mechanisms of the host. This can be accomplished by use of non-native (heterologous) components (promoters, transcription factors, and inducing agents) in the engineered target gene expression systems. These expression systems are called orthogonal, if they are not influenced by the host and also if they are not influencing the host in other ways than intended. The orthogonal expression systems still, however, rely on the host endogenous cellular functions, such as transcription and translation, so they have to fulfil certain criteria permitting their functionality in the host. These criteria are to some extent species (host)-specific, which makes it difficult to design an orthogonal system functional across a broad variety of very dissimilar species.

Typically, the current strategies for expression of heterologous genes employ use of endogenous (host specific) promoters in specific hosts (Hubmann et al. 2014 and Blumhoff et al. 2012). These promoters can be either inducible, or so-called constitutive, but in neither case are they orthogonal, because their function is dependent on specific factors existing in the host organism. Also, the use of host specific promoters prevents the inter-species transfer of these expression systems, which results in the necessity to develop customized expression systems for each host. The existing examples of inter-species transferable expression systems, based on the native host promoters, are limited to a narrow spectrum of closely related organisms, in which the promoters works. These include some yeast promoters, such as *Kluyveromyces lactis* URA3 and LEU2, or *Schizosaccharomyces pombe* HIS5 promoters functional in *Saccharomyces cerevisiae*. In filamentous fungi, for instance gpdA promoter of *Aspergillus nidulans* has been successfully used in *Aspergillus niger, Aspergillus fumigatus*, and *Trichoderma reesei*. These promoters are, however, mainly used for expression of selection marker genes in these organisms. They are not suitable for target gene expression (encoding a desired protein) and especially not for simultaneous expression of multiple genes (encoding a metabolic pathway), because their activity is strongly influenced by growth conditions or they confer an insufficient spectrum of transcriptional activities.

Several studies have reported the characterization and engineering of gene expression systems that employ synthetic (orthogonal) transcription factors (sTFs) and engineered sTF-dependent promoters to control the expression of target genes. The sTF-dependent promoters are composed of a variable number of sTF-binding sites linked to a core promoter. The number of binding sites in combination with a specific core promoter defines the level of expression of the target gene and it represents a significant improvement in expression level control compared to the systems which utilize host-specific promoters for the target gene expression. The sTFs used in these expression systems are, however, expressed from native (host-specific) promoters or modified native promoters, which makes these systems only partially orthogonal, and which prohibits their use in diverse species. Examples of the partially orthogonal expression systems include:

1) Expression system developed for *S. cerevisiae*, where the sTF is expressed from the *S. cerevisiae* TDH3 promoter or from promoter combining the TDH3 UAS and the *S. cerevisiae* CYC1 core promoter, and the target genes are expressed from synthetic promoters containing a diverse number of sTF binding sites and TDH3 or CYC1 core promoters (Ito et al., 2015)

2) Expression system developed for *A. nidulans* and *A. niger*, where the sTF is expressed from the *A. nidulans* gpdA promoter, and the target gene is expressed from a synthetic promoter containing three binding sites for the sTF, *S. cerevisiae* URA3 core promoter, and a 94 bp random sequence derived from *E. coli* (Pachlinger et al., 2005).

3) Expression system developed for *Arabidopsis thaliana*, where the sTF is expressed from the *A. thaliana* 35S promoter, or other *A. thaliana* promoter, or from a synthetic promoter containing four binding sites for the sTF and *A. thaliana* 35S minimal promoter. The minimal promoter probably refers to a core promoter in the referred publication. The target gene is expressed from the synthetic promoter containing four binding sites for the sTF and the *A. thaliana* 35S minimal promoter (US2002081667).

Although several gene expression systems have been disclosed in the prior art, there is still a need for gene expression systems for eukaryotic organism hosts (e.g. eukaryotic microorganism hosts) that can provide robust and stable expression, a broad spectrum of expression levels, and can be used in several different eukaryotic organism species and genera such as in several different eukaryotic microorganism species and genera. This would e.g. enable efficient transfer to and testing of engineered metabolic pathways simultaneously in several potential production hosts for functionality evaluation. Furthermore, a true orthogonal expression system would provide benefits to the scientific community who study eukaryotic organisms.

SUMMARY

One objective of the present invention is to provide orthogonal expression systems which are functional (transferable) in a large spectrum of eukaryotic organisms such as eukaryotic microorganisms. Such expression systems would overcome the need to use host-native DNA sequences in constructing the expression systems and, therefore, establishing expression systems not dependent on the intrinsic transcriptional regulation of the expression host.

A further objective of the invention is to provide expression systems, which allow robust, stable, and predictable expression levels of target genes, and which are not influenced by the cultivation conditions or developmental or growth stages of the host organism.

The motivation for the present invention is based on the finding that 1) the use of the host-specific promoters, or their parts, for expressing the sTFs, and 2) the use of species-specific core promoters in the sTF-dependent promoters controlling the expression of the target genes are the main reasons why the current expression systems based on sTFs cannot be transferred between diverse species without loss of their function.

The present invention shows that it is advantageous to use a core promoter alone for the expression of a sTF. This allows low, constitutive expression of sTF in the host (e.g. microorganism host).

Furthermore, the present invention shows that it is possible to develop a method to identify core promoters that are functional in distant species.

In addition, the present invention shows that it is possible to construct expression systems based on these core promoters functional in diverse species, which allow tunable expression levels of target genes across a large spectrum of eukaryotic organisms (e.g. eukaryotic microorganisms).

Hence, the present invention provides an expression system for a eukaryotic host (e.g. microorganism host), which comprises:
(a) an expression cassette comprising a core promoter, said core promoter being the only "promoter" controlling the expression of a DNA sequence encoding synthetic transcription factor (sTF), and
(b) one or more expression cassettes each comprising a DNA sequence encoding a desired protein product operably linked to a synthetic promoter, said synthetic promoter comprising a core promoter identical to (a) or another core promoter, and sTF-specific binding sites upstream of the core promoter.

The present invention provides also a eukaryotic host, such as a eukaryotic microorganism host, comprising the expression system.

Furthermore, the present invention provides a method for producing a desired protein product (or multiple desired protein products simultaneously) in a eukaryotic host comprising cultivating the eukaryotic host under suitable cultivation conditions.

Furthermore, the present invention provides a method for producing a desired protein product (or multiple desired protein products simultaneously) in a eukaryotic microorganism host comprising cultivating the eukaryotic microorganism host under suitable cultivation conditions.

The present invention provides also a method for identifying universal core promoters for eukaryotic hosts.

The identification method comprises the following steps:
constitutively expressing a synthetic transcription factor, sTF, in *Saccharomyces* cerevisiae,
in the same host co-expressing a reporter gene operably linked to a sTF-dependent test promoter, said sTF-dependent test promoter comprising a core promoter to be tested, and sTF binding sites upstream to that,
allowing said reporter gene to be expressed under the test promoter in the presence of activation by the sTF,
assessing the level of expression of the reporter gene, and
selecting from the tested core promoters, core promoters showing at least 40% as high expression of the reporter gene as obtained with *S. cerevisiae* PGK1 core promoter tested in the same reporter system;
In specific cases, also selecting core promoters showing lower than 40% expression of the reporter gene as compared to the reporter gene expression obtained with *S. cerevisiae* PGK1 core promoter tested in the same reporter system.

Furthermore, the present invention provides a universal core promoter (UCP). The universal core promoter is obtainable by the disclosed identification method.

A universal core promoter (UCP) typically comprises a DNA sequence containing the 5"-upstream region of a eukaryotic gene, starting 10-50 bp upstream of a TATA-box and ending 9 bp upstream of the ATG start codon. The distance between the TATA-box and the start codon is preferably no greater than 180 bp and no smaller than 80 bp. The UCP typically comprises also a DNA sequence comprising random 1-20 bp at its 3'-end. In one embodiment a UCP typically comprises a DNA sequence having at least 90% sequence identity to said 5"-upstream region of a eukaryotic gene, and a DNA sequence comprising random 1-20 bp at its 3'-end.

Furthermore, the present invention provides an expression system for a eukaryotic host, which comprises
(a) an expression cassette comprising a UCP, said UCP controlling the expression of a DNA sequence encoding synthetic transcription factor (sTF), and
(b) one or more expression cassettes each comprising a DNA sequence encoding a desired protein product operably linked to a synthetic promoter, said synthetic promoter comprising a UCP identical to (a) or another UCP, and sTF-specific binding sites upstream of the UCP.

In addition, the present invention provides a eukaryotic host (e.g. a eukaryotic microorganism host) comprising an expression system using universal core promoters.

The present invention provides also a method for producing a desired protein product (or multiple desired protein products simultaneously) in a eukaryotic host (e.g. a eukaryotic microorganism host) using an expression system with universal core promoters.

The present invention thus provides an orthogonal expression system which is functional (transferable) in a large spectrum of eukaryotic organisms or eukaryotic microorganisms, which allows robust, stable, and predictable expression levels of target genes, and is not influenced by cultivation conditions or developmental or growth stages of the host organism.

The expression system provided by the present invention simplifies and focuses the genetic tools needed for constructing new expression hosts. Currently there is a wide array of expression systems that are highly organism and species specific. With the present invention, industry and wider scientific community working on eukaryotic organisms can adopt a smaller, common set of orthogonal expression tools. This would benefit the community and drive forward new innovations in the field.

DETAILED DESCRIPTION

Definitions

Figure 1:
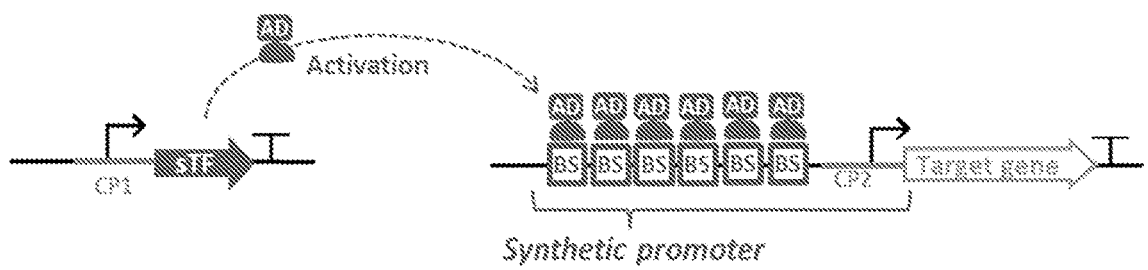
FIG. 1 depicts a scheme of an expression system for expression of a single gene in a eukaryotic organism (e.g. a eukaryotic microorganism).

Unless otherwise defined, all technical and scientific terms used herein have the same meaning as commonly understood by one of ordinary skill in the art to which this invention belongs.

DNA refers to deoxyribonucleic acid.

Codon is a tri-nucleotide unit which is coding for a single amino acid in the genes that code for proteins. The codons encoding one amino acid may differ in any of their three nucleotides. Different organisms have different frequency of the codons in their genomes, which has implications for the efficiency of the mRNA translation and protein production.

Coding sequence refers to a DNA sequence that encodes a specific RNA or polypeptide (i.e. a specific amino acid sequence). The coding sequence could, in some instances, contain introns (i.e. additional sequences interrupting the reading frame, which are removed during RNA molecule maturation in a process called RNA splicing). If the coding sequence encodes a polypeptide, this sequence contains a reading frame.

Reading frame is defined by a start codon (AUG in RNA; corresponding to ATG in the DNA sequence), and it is a sequence of consecutive codons encoding a polypeptide (protein). The reading frame is ending by a stop codon (one of the three: UAG, UGA, and UAA in RNA; corresponding to TAG, TGA, and TAA in the DNA sequence). A person skilled in the art can predict the location of open reading frames by using generally available computer programs and databases.

Eukaryotic Promoter is a region of DNA necessary for initiation of transcription of a gene. It is upstream of a DNA sequence encoding a specific RNA or polypeptide (coding sequence). It contains an upstream activation sequence (UAS) and a core promoter. A person skilled in the art can predict the location of a promoter by using generally available computer programs and databases.

Core promoter (CP) is a part of a eukaryotic promoter and it is a region of DNA immediately upstream (5'-upstream region) of a coding sequence which encodes a polypeptide, as defined by the start codon. The core promoter comprises all the general transcription regulatory motifs necessary for initiation of transcription, such as a TATA-box, but does not comprise any specific regulatory motifs, such as UAS sequences (binding sites for native activators and repressors).

Core promoter is defined for the purpose of the present invention as a DNA sequence containing: 1) a 5"-upstream region of a highly expressed gene starting 10-50 bp upstream of the TATA box and ending 9 bp upstream of the start codon, where the distance between the TATA box and the start codon is no greater than 180 bp and no smaller than 80 bp, 2) random 1-20 bp, typically 5 to 15 or 6 to 10, which are located in place of the 9 bp of the DNA region (1) immediately upstream of the start codon; or as a DNA sequence containing: 1) a DNA sequence having at least 90%, 91%, 92%, 93%, 94%, 95%, 96%, 97%, 98% or 99% sequence identity to said 5"-upstream region and 2) random 1-20 bp, typically 5 to 15 or 6 to 10, which are located in place of the 9 bp of the DNA region (1) immediately upstream of the start codon.

A highly expressed gene in an organism in the context of this invention is a gene which has been shown in that organism to be expressed among the top 3% or 5% of all genes in any studied condition as determined by transcriptomics analysis, or a gene, in an organism where the transcriptomics analysis has not been performed, which is the closest sequence homologue to the highly expressed gene.

TATA-box is defined for the purpose of the present invention as a DNA sequence (TATA) upstream of the start codon, where the distance of the TATA sequence and the start codon is no greater than 180 bp and no smaller than 80 bp. In case of multiple sequences fulfilling the description, the TATA-box is defined as the TATA sequence with smallest distance from the start codon.

Transcription factor refers to a protein that binds to specific DNA sequences present in the UAS, thereby controlling the rate of transcription, which is performed by RNA II polymerase. Transcription factors perform this function alone or with other proteins in a complex, by promoting (as an activator), or blocking (as a repressor) the recruitment of RNA polymerase to core promoters of genes.

Synthetic transcription factor (sTF) refers to a protein which functions as a transcription factor, but is not a native protein of a host organism. In the context of this invention, the sTF is an artificial protein which typically comprises a DNA-binding protein of prokaryotic origin, a nuclear localization signal, and a transcription activation domain of viral origin.

Synthetic promoter refers to a region of DNA which functions as a eukaryotic promoter, but it is not a naturally occurring promoter of a host organism. It contains an upstream activation sequence (UAS) and a core promoter, wherein the UAS, or the core promoter, or both elements, are not native to the host organism. In the context of this invention, the synthetic promoter comprises (usually 1-10, typically 1, 2, 4 or 8) sTF-specific binding sites (synthetic UAS sUAS) linked to a core promoter.

DNA binding domain or DBD refers to the region of a protein, typically specific protein domain, which is responsible for interaction (binding) of the protein with a specific DNA sequence.

Universal core promoter (UCP) is a core promoter which confers sufficient (usually but not necessarily at least 40% of) reporter expression or activity level, such as fluorescence level, obtained with the *Saccharomyces cerevisiae* PKG1 core promoter tested in a CP-screening system as disclosed in the present invention. A core promoter selected by using this system typically provides sufficient expression of a transcription factor in various species and genera of eukaryotic organisms.

An orthogonal expression system means here an expression system consisting of heterologous (non-native) core promoters, transcription factor(s), and transcription-factor-specific binding sites. Typically, the orthogonal expression system is functional (transferable) in diverse eukaryotic organisms such as eukaryotic microorganisms.

CP-screening system is constructed in *Saccharomyces cerevisiae* and it comprises a *Saccharomyces cerevisiae* strain constitutively expressing a sTF and preferably a centromeric type reporter plasmid assembled with the core promoter to be tested. The reporter plasmid typically contains binding sites specific for the sTF, a reporter gene, such as mCherry gene, and a terminator, such as the ADH1 terminator for the mCherry gene. The tested core promoter is inserted between the sTF binding sites and the reporter gene. The tested core promoter typically comprises at its 3'-end a sequence comprising 1-20 random nucleotides, such as sequence TTAATTAAA, and typically including restriction sites. The function of the core promoter is assessed by a reporter measurement, such as fluorescence measurement of the resulting strain and compared to a control strain where the core promoter is the *Saccharomyces cerevisiae* PKG1 core promoter.

A centromeric plasmid refers here to a single or low copy number plasmid used in *S. cerevisiae*. This plasmid is containing DNA regions functional as a centromere (CEN sequence) and as an autonomously replicating sequence (ARS) in *S. cerevisiae*. The ARS sequence provides replication origin and the CEN sequence regulates replication and distribution of the plasmids during cell division which makes the centromeric plasmid analogous to a chromosome.

Sufficient expression of a transcription factor is defined as an expression level of a transcription factor which leads to transcription activation of a gene or genes which are under the control of the transcription factor-dependent promoter(s).

Eukaryotic organism is defined in the context of this invention as an organism belonging to: 1) Fungal kingdom, including yeast, such as classes Saccharomycetales, including but not limited to species *Saccharomyces cerevisiae, Kluyveromyces lactis, Candida krusei (Pichia kudriavzevii), Pichia pastoris (Komagataella pastoris), Eremothecium gossypii, Kazachstania exigua, Yarrowia lipolytica*, and others; or *Schizosaccharomycetes*, such as *Schizosaccharomyces pombe*; filamentous fungi, such as classes Eurotiomycetes, including but not limited to species *Aspergillus niger, Aspergillus nidulans, Penicillium chrysogenum*, and others; Sordariomycetes, including but not limited to species *Trichoderma reesei, Myceliophthora thermophile*, and others; or Mucorales, such as *Mucor indicus* and others. 2) Plant kingdom, including flowering plants, such as orders Solanales, including but not limited to genus *Nicotiana (N. benthamiana), Solanum (S. tuberosum), Lycopersicon (L. esculentum), Capsicum (C. anuum)* and others; Brassicales including but not limited to genus *Arabidopsis (A. thaliana), Brassica (B. napus)*, and others; Poales including but not limited to species *Avena sativa, Secale cereale, Zea mays, Triticum* spp., *Oryza sativa, Hordeum* vulgare, *Sorghum bicolor, Saccharum officinarum*, and others; Fabales including but not limited to species *Phaseolus* spp., *Vigna* spp., *Glycine max, Pisum sativum, Lens culinaris, Cicer arietinum* and others; Malpighiales, including but not limited to genus *Populus*, and others; Pinales, including but not limited to genus *Pinus*, and others; or Arecales including but not limited to species *Elaeis guineensis, Cocos nucifera*, and others; and green algae, such as classes Chlorophyceae, including but not limited to genus *Chlamydomonas (C. reinhardtii)*; or Trebouxiophyceae, including but not limited to species *Chlorella* spp., and others. 3) Animal kingdom, including mammals (Mammalia), including but not limited to species *Mus musculus* (mouse), *Cricetulus griseus* (hamster), *Homo sapiens* (human), and others; insects, including but not limited to species *Mamestra brassicae, Spodoptera frugiperda, Trichoplusia ni, Drosophila melanogaster*, and others.

Eukaryotic microorganism is defined in the context of the invention as a microorganism including yeast, such as classes Saccharomycetales, including but not limited to species *Saccharomyces cerevisiae, Kluyveromyces lactis, Candida krusei (Pichia kudriavzevii), Pichia pastoris (Komagataella pastoris), Eremothecium gossypii, Kazachstania exigua, Yarrowia lipolytica*, and others; *Schizosaccharomycetes*, such as *Schizosaccharomyces pombe*; and filamentous fungi, such as classes Eurotiomycetes, including but not limited to species *Aspergillus niger, Aspergillus nidulans, Penicillium chrysogenum*, and others; Sordariomycetes, including but not limited to species *Trichoderma reesei, Myceliophthora thermophile*, and others; Mucorales, such as *Mucor indicus* and others.

The present invention provides an expression system for a eukaryotic host, which comprises
(a) an expression cassette comprising a core promoter; the core promoter being the only promoter for controlling the expression of a DNA sequence encoding synthetic transcription factor (sTF), and
(b) one or more expression cassettes each comprising a DNA sequence encoding a desired protein product operably linked to a synthetic promoter; the synthetic promoter comprises a core promoter, which is identical to the core promoter in (a) or another core promoter, and one or more sTF-specific binding sites upstream of the core promoter.

The core promoter typically comprises a DNA sequence containing the 5"-upstream region of a eukaryotic gene, starting 10-50 bp upstream of a TATA-box and ending 9 bp upstream of the ATG start codon. The distance between the TATA-box and the start codon is no greater than 180 bp and no smaller than 80 bp. The core promoter typically comprises also a DNA sequence comprising random 1-20 bp at its 3'-end. In one embodiment the core promoter typically comprises a DNA sequence having at least 90% sequence identity to said 5"-upstream region of a eukaryotic gene, and a DNA sequence comprising random 1-20 bp at its 3'-end.

The DNA sequence encoding the synthetic transcription factor (sTF) typically comprises a prokaryotic transcription regulator, a nuclear localization signal, and a transcription activation domain.

Figure 3:
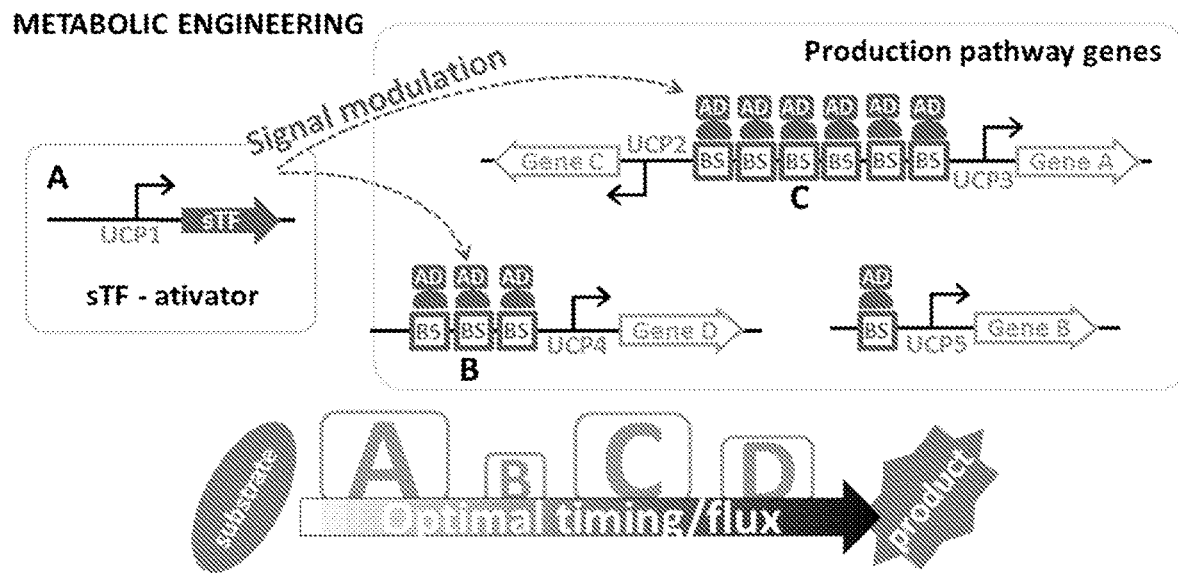
FIG. 3 depicts a scheme of an expression system utilizing the UCPs for simultaneously regulating the expression of multiple genes in a eukaryotic organism such as a eukaryotic microorganism.

The CPs used in the expression system can be different, or the first one, CP1, can be identical to the second one CP2, (or the third one CP3, or the fourth one CP4). This is illustrated in FIGS. 1 and 3.

The two expression cassettes ((a) and (b)) can be introduced to a eukaryotic host (typically integrated into a genome) as two individual DNA molecules, or as one DNA molecule in which the two (or more) expression cassettes are connected (fused) to form a single DNA.

In specific applications, where the target gene is a native (homologous) gene of a host organism, the synthetic promoter can also be inserted immediately upstream of the target gene coding region in the genome of the host organism, possibly replacing the original (native) promoter of the target gene.

More specifically, the expression system thus comprises two DNA-parts, which are assembled into the expression system comprising at least two individual expression cassettes:

(a) a sTF synthetic transcription factor cassette, which comprises a CP controlling expression of a gene encoding a fusion protein (sTF), the sTF itself, and a terminator. The sTF comprises a DNA-binding protein derived from prokaryotic origin, typically bacterial transcription regulators, such as from the TetR family; nuclear localization signal, such as the SV40 NLS; and a transcription activation domain, such as the VP16 or VP64 activation domain; and (b) a target gene expression cassette, which comprises a synthetic promoter, which comprises a variable number of sTF-binding sites, usually 1 to 10, typically 1, 2, 4 or 8, separated by 0-20, typically 5-15, random nucleotides, a CP, a target gene, and a terminator.

The composition of the example expression system is illustrated in FIG. 1. The present invention is based on the idea to use a core promoter (CP), instead of a full promoter, for expression of a synthetic transcription factor (sTF). Some CPs can sustain low level of transcription when placed in front of a gene. Due to the absence of specific regulatory sequences required for conditional transcription control which are present in full promoters (typically in the upstream activating sequence UAS), this transcription is constitutive that is constant in all growth or metabolic conditions. Because the general transcription machinery is evolutionarily conserved, some of the CPs can function in very diverse species. These features are used in the invention for construction of species-transferable expression systems.

The constitutive low expression of the sTF gene facilitated by a CP provides a sufficient amount of a synthetic transcription factor, which binds to its specific binding sites on the synthetic promoter of the target gene and activates its expression. The number of the binding sites is proportional to the expression level of the target gene(s), where more binding sites results in higher expression. The synthetic promoter comprises, in addition to the sTF-binding sites, also a CP. The choice of the CP in the synthetic promoter controlling the expression of the target gene(s) is also important for the expression level of the target gene(s). The combination of the sTF-binding sites and the CP can result in a range of expression levels which can be modulated from very low to very high. At the high end, the expression achieved by this system exceeds the expression levels of the most highly expressed native genes in a host organism.

FIG. 1 illustrates an example of a scheme of an expression system for expression of a single gene in a eukaryotic organism or microorganism. The synthetic transcription factor (sTF) expression cassette contains a CP (CP1), a sTF coding sequence, and a terminator. The CP1 provides constitutive low expression of the sTF. Therefore the sTF is present in a host cell in a constant level all the time, in all growth conditions, and all developmental and growth stages. The target gene expression cassette contains a synthetic promoter, a target gene coding sequence, and a terminator. The synthetic promoter comprises multiple sTF-specific binding sites (usually 1-10, typically 1, 2, 4 or 8; forming a synthetic upstream activating sequence sUAS), and a CP (CP2). The target gene encodes a protein product of interest.

The transcription activity of the CP1, the "signal", is "amplified" by the sTF bound to the sUAS. This leads to activation of transcription on the CP2, resulting in expression of the target gene. As discussed above, the two expression cassettes can be introduced into a eukaryotic host (typically integrated into a genome) as two individual DNA molecules, or as one DNA molecule in which the two cassettes are connected (fused) into a single DNA. In specific applications, where the target gene is a native (homologous) gene of a host organism, the synthetic promoter can also be inserted immediately upstream of the target gene coding region in the genome of the host organism. The CPs used in the expression system can be different, or the CP1 can be identical to the CP2.

The present invention also provides a eukaryotic host (e.g. a eukaryotic microorganism host) which comprises the expression system as disclosed herein.

A eukaryotic organism refers here in particular to 1) fungal species including yeast, such as species from classes Saccharomycetales, including but not limited to *Saccharomyces cerevisiae, Kluyveromyces lactis, Candida krusei* (*Pichia kudriavzevii*), *Pichia pastoris* (*Komagataella pastoris*), *Eremothecium gossypii, Kazachstania exigua, Yarrowia lipolytica*, and others; Schizosaccharomycetes, such as *Schizosaccharomyces pombe*; and filamentous fungi species, such as those from classes Eurotiomycetes, including but not limited to *Aspergillus niger, Aspergillus nidulans, Penicillium chrysogenum*, and others; Sordariomycetes, including but not limited to *Trichoderma reesei, Myceliophthora thermophile*, and others; Mucorales, such as *Mucor indicus* and others; 2) plant species including flowering plants, such as species from orders Solanales, including but not limited to *Nicotiana benthamiana, Solanum tuberosum, Lycopersicon esculentum, Capsicum anuum* and others; Brassicales, including but not limited to *Arabidopsis thaliana, Brassica napus*, and others; Poales, including but not limited to *Avena sativa, Secale cereale, Zea mays, Triticum* spp. *Oryza sativa, Hordeum vulgare, Sorghum bicolor, Saccharum officinarum*, and others; Poales, including but not limited to *Phaseolus* spp., *Vigna* spp., *Glycine max, Pisum sativum, Lens culinaris, Cicer arietinum* and others; Malpighiales, including but not limited to *Populus* sp., and others; Pinales, including but not limited to *Pinus* sp., and others; or Arecales including but not limited to *Elaeis guineensis, Cocos nucifera*, and others; and green algae species, including but not limited to *Chlamydomonas reinhardtii, Chlorella* spp. and others; 3) Animal species including but not limited to mammals (Mammalia), including but not limited to species *Mus musculus* (mouse), *Cricetulus griseus* (hamster), *Homo sapiens* (human), and others; insect species, including but not limited to species *Mamestra brassicae, Spodoptera frugiperda, Trichoplusia ni, Drosophila melanogaster*, and others.

The present invention also provides a method for producing a desired protein product in a eukaryotic host (e.g. microorganism host) comprising cultivating the host under suitable cultivation conditions.

By suitable cultivation conditions are meant any conditions allowing survival or growth of the host organism, and/or production of the desired product in the host organism. Desired product can be a product of the target gene or genes (protein or proteins), or compound produced by a protein (enzyme) or by a metabolic pathway. In the present context the desired product is typically a protein (enzyme) product.

The present invention also provides a gene expression system which is functional in several different eukaryotic species and genera. The key element in the system is a core promoter which facilitates expression in several species. Such a core promoter is here called universal core promoter UCP.

This property, so called basal transcription activity, is based on efficient recruitment of the RNA polymerase II complex to the core promoter; and it results in low but stable expression level in all cultivation and growth (developmental) conditions. This low constitutive signal is amplified by a synthetic transcription factor (sTF), whose expression is controlled by the UCP, to adjustable expression level of target genes (native or heterologous). Each target gene is under the control of an engineered promoter and comprises a selected number of sTF-specific binding sites and a UCP. The combination of the sTF-specific binding sites and the UCP defines the expression level of the target gene.

This provides means to control expression in diverse hosts, including those with undeveloped know-how. Applications of the use of UCPs are protein production, metabolic engineering and artificial genetic regulatory networks.

Furthermore, the system can be used as a platform to identify new UCPs with novel properties.

The present invention provides a method for identifying a universal core promoter for eukaryotic hosts. The method comprises
  constitutively expressing a synthetic transcription factor, sTF, in *Saccharomyces* cerevisiae,
  co-expressing in the same host a reporter gene operably linked to a sTF-dependent test promoter, said sTF-dependent test promoter comprising a core promoter to be tested, and sTF binding sites upstream to that,
  allowing said reporter gene to be expressed under the test promoter in the presence of activation by the sTF,
  assessing the level of expression of the reporter gene, and
  selecting from the tested core promoters, core promoters showing at least 40% as high expression of the reporter gene as obtained with *S. cerevisiae* PGK1 core promoter tested in the same reporter system.
  in specific cases, also selecting core promoters showing lower than 40% level of reporter expression More specifically, the method optimally comprises the use of a circular centromeric plasmid comprising sTF specific binding sites operably linked to the tested core promoter, and a reporter gene.

The DNA sequence encoding synthetic transcription factor (sTF) typically comprises a DNA sequence encoding a DNA-binding protein of prokaryotic origin, a nuclear localization signal, and a transcription activation domain. The sTF comprises a DNA-binding protein derived from prokaryotic, typically bacterial origin, transcription regulators, such as a protein from the TetR family; a nuclear localization signal, such as the SV40 NLS; and a transcription activation domain, such as the VP16 or VP64 activation domain.

The promoter to be tested is selected from the promoters of eukaryotic genes expressed to the level of the highest 3% or 5% of all genes in any condition in the given eukaryotic organism.

The present invention provides a universal core promoter (UCP), in which the core promoter is obtainable by the identification method as disclosed herein.

Typically a universal core promoter comprises a DNA sequence containing 1) the 5"-upstream region of a eukaryotic gene, starting 10-50 bp upstream of a TATA-box, and ending 9 bp upstream of the ATG start codon; and 2) a random 1-20 bp DNA sequence which is located in place of the 9 bp of the DNA region (1) immediately upstream of the start codon. The distance between the TATA-box and the start codon of the original eukaryotic gene is no greater than 180 bp and no smaller than 80 bp. In one embodiment the core promoter comprises a DNA sequence having at least 90% sequence identity to said 5'-upstream region, and a random 1-20 bp DNA sequence which is located in place of the 9 bp of the DNA region (1) immediately upstream of the start codon.

The selection of the CPs functional in distant organisms is carried out in *Saccharomyces cerevisiae*, and the sources of the candidate CPs are preferably (but not necessarily) industrially relevant organisms, preferably (but not necessarily) distant in terms of evolutionary divergence or in other features, such as genome architecture or GC-content.

The selection of the candidate CPs is based on the level of expression of the genes in the selected source organisms, containing the candidate CP in their promoters. Another selection criterion is the presence of a TATA-box in the candidate CP (FIG. 2A).

Figure 2A:
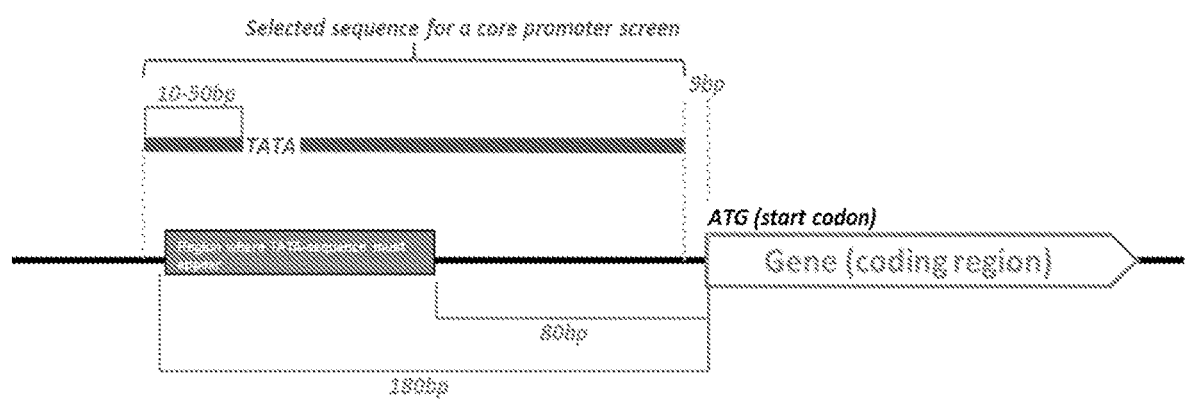
FIGS. 2A, 2B and 2C depict a scheme of the screening method for selecting UCPs from the candidate core promoters.
Figure 2B:
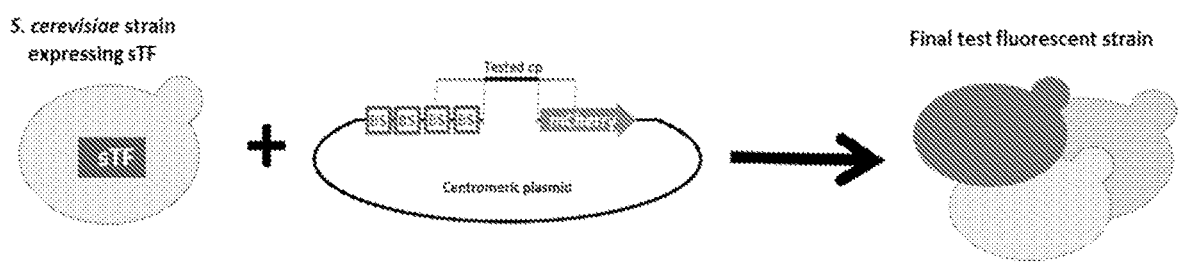

In one embodiment the screen for functional CPs is advantageously performed by in vivo assembling the candidate CP with the sTF-dependent reporter cassette expressed in a *S. cerevisiae* strain constitutively expressing the sTF (FIG. 2B). The resulting strains are tested for a level of a reporter, preferably fluorescence, and these levels are compared to a control strain where the *S. cerevisiae* PGK1 core promoter is used in the reporter construct. The candidate CPs, which facilitate sufficient reporter, preferably fluorescence, levels (usually but not necessarily higher than 40% of) the control strain (FIG. 2C), and therefore fulfil the criteria of the screening are called universal core promoters, UCPs. The selected CPs and UCPs are used for constructing of expression systems.

The resulting expression systems are functional in eukaryotic hosts. These hosts include all eukaryotic organisms, in particular: 1) Fungal microorganisms including filamentous fungi and yeasts, in particular organisms from the following taxa: A) Saccharomycetales, including but not limited to species *Saccharomyces cerevisiae, Kluyveromyces lactis, Candida krusei* (*Pichia kudriavzevii*), *Pichia pastoris* (*Komagataella pastoris*), *Eremothecium* gossypii, *Kazach-* stania exigua, Yarrowia lipolytica, and others; Schizosaccharomycetes, such as Schizosaccharomyces pombe; B) Eurotiomycetes, including but not limited to species Aspergillus niger, Aspergillus nidulans, Penicillium chrysogenum, and others; C) Sordariomycetes, including but not limited to species Trichoderma reesei, Myceliophthora thermophile, and others; D) Mucorales, such as Mucor indicus and others. 2) Plant organisms, including flowering plants and green algae, in particular organisms from the following taxa: E) Solanales, including but not limited to species Nicotiana benthamiana, Solanum tuberosum, Lycopersicon esculentum, Capsicum anuum, and others; F) Brassicales, including but not limited to species Arabidopsis thaliana, Brassica napus, and others; G) Poales, including but not limited to species Avena sativa, Secale cereale, Zea mays, Triticum spp., Oryza sativa, Hordeum vulgare, Sorghum bicolor, Saccharum officinarum, and others; H) Fabales including but not limited to species Phaseolus spp., Vigna spp., Glycine max, Pisum sativum, Lens culinaris, Cicer arietinum and others; I) Malpighiales, including but not limited to species Populus sp., and others; J) Pinales, including but not limited to species Pinus sp., and others; K) Arecales including but not limited to species Elaeis guineensis, Cocos nucifera, and others; L) Chlorophyceae, including but not limited to species Chlamydomonas reinhardtii, and others; M) Trebouxiophyceae, including but not limited to species Chlorella spp., and others. 3) Animal organisms, in particular organisms from the following taxa: N) mammals (Mammalia), including but not limited to species Mus musculus (mouse), Cricetulus griseus (hamster), Homo sapiens (human), and others; O) insects (Insecta), including but not limited to species Mamestra brassicae, Spodoptera frugiperda, Trichoplusia ni, Drosophila melanogaster, and others.

FIGS. 2A, B and C illustrate an example of a scheme of the screening method used for selecting UCPs from the candidate core promoters.

FIG. 2A illustrates a scheme of selection of a candidate core promoter in a eukaryotic organism. The DNA region immediately upstream of a gene of any eukaryotic organism, which belongs to a group of top 3% or 5% most highly expressed genes in any condition, is analyzed for presence of TATA sequence (TATA-box) within −180 bp and −80 bp upstream of a start codon (ATG). If more than one TATA sequence appears in this region, then the one closest to the ATG (start codon) is chosen as a TATA-box. The sequence starting 10-50 bp upstream of the TATA-box and ending 9 bp upstream of the ATG (start codon) is selected for the core promoter screen.

FIG. 2B illustrates a Saccharomyces cerevisiae strain constitutively expressing a sTF. It is co-transformed typically with a linearized centromeric (single or low copy number) plasmid, and a library, or individual versions, of the core promoters to be tested. The centromeric plasmid contains typically for example 4 sTF binding sites, the reporter gene, such as mCherry gene, and it is linearized between these two features as shown in the figure. Each core promoter DNA fragment comprises the selected DNA sequence (FIG. 2A) followed by a sequence comprising random nucleotides, typically containing restriction sites, here one useful sequence is for example TTAATTAAA, and flanked by 20-50 bp long DNA sequences on each end. These flanking sequences are homologous to each end of the linearized plasmid, the 5'-flanking sequence is homologous to a region partly covering the sTF binding sites in the linearized plasmid, and the 3'-flanking sequence is homologous to the 5'-end of the reporter gene, such as mCherry gene, open reading frame. After the transformation, the plasm id is assembled in vivo by an intrinsic homologous recombination machinery of the Saccharomyces cerevisiae yeast, resulting in the circular centromeric plasmid comprising the sTF binding sites, followed by a core promoter including a sequence, such as TTAATTAAA, and the reporter gene, such as mCherry gene. The resulting strains are analyzed for the reporter, such as a red fluorescence caused by the produced mCherry protein. The level of intensity of the reporter, such as fluorescence, is corresponding to the level of expression of the reporter gene, such as mCherry gene, which is corresponding to the function of the tested core promoter.

Figure 2C:
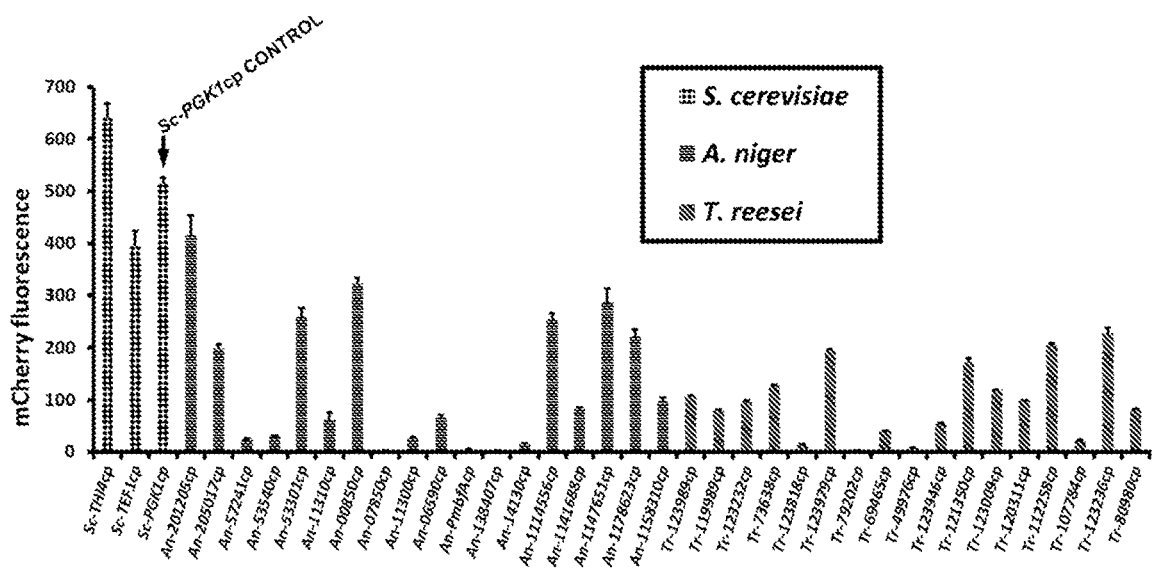
Figure 2C:
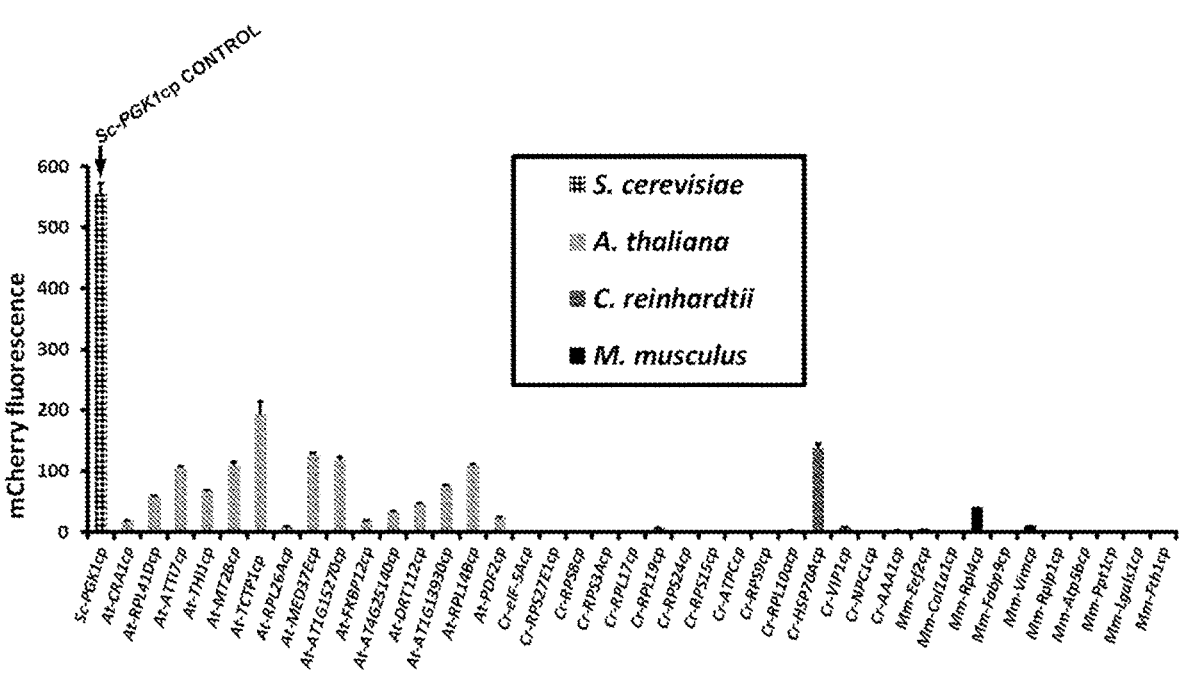

FIG. 2C) The transformed strains, which confer sufficient level of reporter, such as fluorescence, which is typically 40% or higher than the reporter, such as fluorescence of the strain containing the PGK1 core promoter assembled in the same centromeric plasmid (highlighted by arrow in the figure), are selected. The centromeric plasmids are isolated from the selected strains, the plasmid DNA is purified and sequenced, and the selected core promoters are used for subsequent constructions of expression cassettes for testing in other eukaryotic organisms. In specific cases, also core promoters which do not confer 40% or higher level of reporter expression are used for constructions of expression cassettes for eukaryotic organisms. In case the core promoter is functional in the core-promoter-donor host and also in at least one other host which is different species than the core-promoter-donor host, then the core promoter is assigned as universal core promoter, UCP.

The present invention provides a universal core promoter (UCP), which is obtainable by the disclosed method. Typically the UCP comprises a DNA sequence containing: 1) the 5'-upstream region of a eukaryotic gene, starting 10-50 bp upstream of a TATA-box and ending 9 bp upstream of the ATG start codon, and wherein the distance between the TATA-box and the start codon is no greater than 180 bp and no smaller than 80 bp. 2) and a DNA sequence comprising random 1-20 bp which is located at the 3'-end of the DNA sequence (1). In one embodiment the universal core promoter comprises 1) a DNA sequence having at least 90% sequence identity to said 5'-upstream region and 2) a DNA sequence comprising random 1-20 bp which is located at the 3'-end of the DNA sequence.

The present invention provides also an expression system for a eukaryotic host, which comprises
(a) an expression cassette comprising an UCP,
said UCP controlling the expression of a DNA sequence encoding synthetic transcription factor (sTF), and
(b) one or more expression cassettes each comprising a DNA sequence encoding a desired protein product operably linked to a synthetic promoter,
said synthetic promoter comprising UCP of (a) or another UCP, and sTF-specific binding sites upstream of the UCP.

It is possible to construct multiple synthetic promoters with different numbers of binding sites (usually 1-10, typically 1, 2, 4 or 8, separated by 0-20, typically 5-15 random nucleotides) controlling different target genes simultaneously by one sTF. This would for instance result in a set of differently expressed genes forming a metabolic pathway.

FIG. 3 illustrates an example of a scheme of an expression system utilizing the UCPs for a simultaneous regulation of expression of multiple genes in a eukaryotic organism (e.g. microorganism). The scheme depicts a hypothetical metabolic pathway, but the approach could also be used for other multi-gene expression systems (signaling, transport, or glycosylation pathways, simultaneous protein production, etc.) or their combinations.

The synthetic transcription factor (sTF) expression cassette (A) in FIG. 3 is analogous to the one shown in FIG. 1, fulfilling the same purpose. The target gene expression cassettes can be present in variable number ranging from 1 to 20. Each target gene expression cassette contains a synthetic promoter, which can have either classical (monodirectional) architecture (B), or a bidirectional design (C). The synthetic promoter (mono- or bidirectional) consists of multiple sTF-specific binding sites (usually 1-10, typically 1, 2, 4 or 8), and a UCP. The target genes (Gene A, B, C, D) encode proteins of interest which can form a metabolic pathway or its part, or encode any combination of proteins depending on the application.

The function of the expression system illustrated in FIG. 3 is analogous to the one presented in FIG. 1, transcription activity of the UCP1 is "modulated" by sTF bound to the sUASs of the target genes. The occupancy of each sUAS in combination with UCPs leads to specific expression levels of each individual gene, resulting in specific levels of the target proteins. The expression cassettes can be introduced to a eukaryotic host (typically integrated into a genome) as individual DNA molecules or as larger DNA molecules where the individual expression cassettes are fused together. In specific applications, where the target genes are native (homologous) genes of a host organism the synthetic promoters can also be inserted immediately upstream of each target gene coding region in the genome of the host organism. The UCPs used in the expression system can be different, or some or all of the UCPs can also be identical.

The present invention provides a eukaryotic host comprising the disclosed expression system. These hosts include all eukaryotic organisms, in particular fungal microorganisms, including filamentous fungi and yeasts, plant hosts, including flowering plans and algae, and animal hosts, including mammals and insects.

The present invention provides also a method for producing a desired protein product in a eukaryotic host (e.g. microorganism host) comprising cultivating the host under suitable cultivation conditions.

The tuning of the expression system for different expression levels can be carried out in *S. cerevisiae* where a multitude of options, including choices of UCPs, sTFs, different numbers of BSs, and target genes, can be tested rapidly. The established optimal set of differently expressed genes can be directly transferred into destination host, where it retains its function. The high level of expression achieved by this system can also be utilized in the protein (enzyme) production hosts. The advantage of using *S. cerevisiae* is the availability of well-established and fast methods for genetic modifications, DNA transformation, screening, analyses, cultivations, and in silico modelling. This will speed up the process of industrial host development and enable the use of novel hosts which have high potential for specific purposes, but very limited spectrum of tools for genetic engineering.

Figure 4:
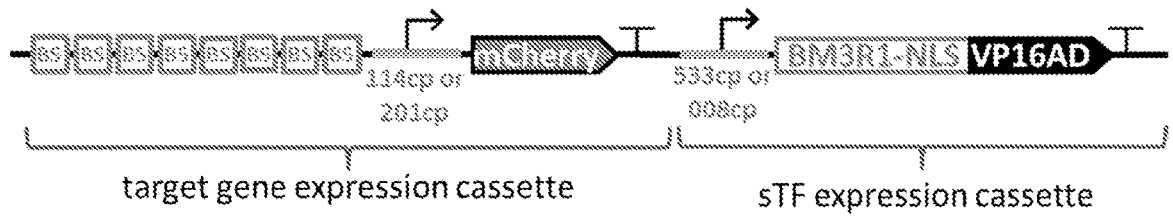
FIG. 4 depicts examples of the expression systems functional/transferable in diverse organisms or microorganisms.

FIG. 4 illustrates examples of the expression systems functional/transferable in diverse eukaryotic organisms. The expression systems assembled in a single DNA molecule comprises two expression cassettes: 1) sTF expression cassette, which comprises different UCPs, exemplified here either with the 533 cp or 008 cp (see Table 1 and 2), the sTF version with the DNA-binding protein, exemplified here by BM3R1, and a terminator, exemplified here by the *Trichoderma reesei* TEF1 terminator. And 2) the target gene expression cassette comprises a number of sTF specific binding sites, exemplified here by eight BM3R1-specific binding sites, different UCPs, exemplified here by either 114 cp or 201 cp (see Table 1 and 2), the reporter gene coding region, exemplified here by the mCherry (red fluorescent protein) coding region, and a terminator, exemplified here by the *S. cerevisiae* ADH1 terminator. The coding region of the DNA binding protein, here BM3R1, was codon-optimized to fit the codon usage of *Aspergillus niger*. In the Example 3, the expression system version containing 201 cp and 008 cp is referred to as "version A", and the expression system version containing 114 cp and 533 cp is referred to as "version B".

Figure 5A:
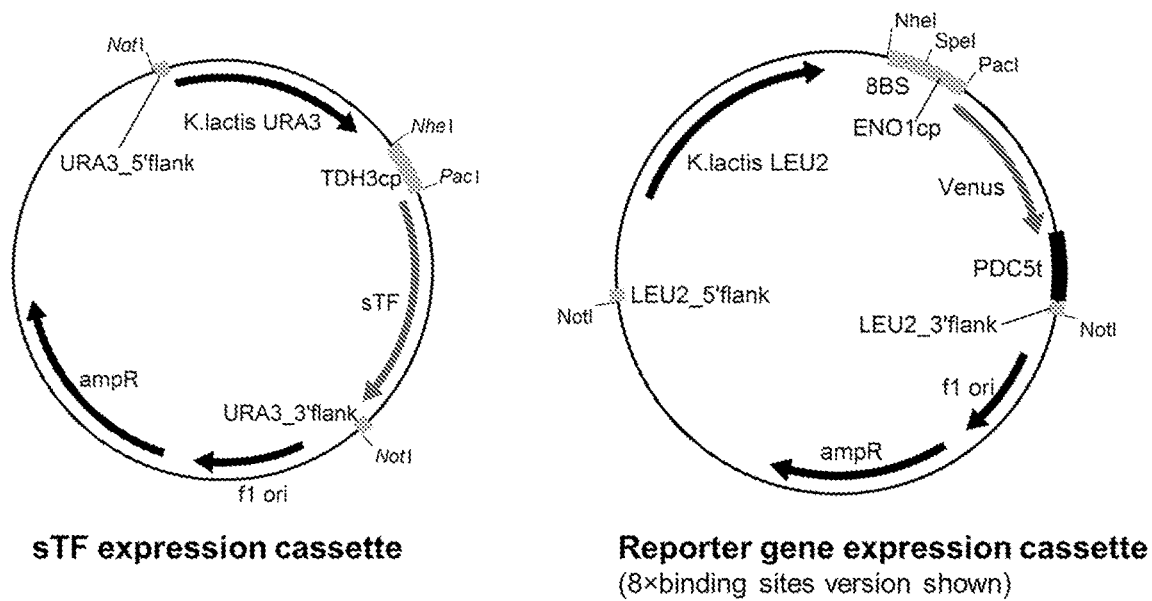
FIGS. 5A and 5B depict testing of different versions of the sTFs and assessment of modulation of the expression system's performance in *Saccharomyces cerevisiae* by fluorometry.
Figure 5B:
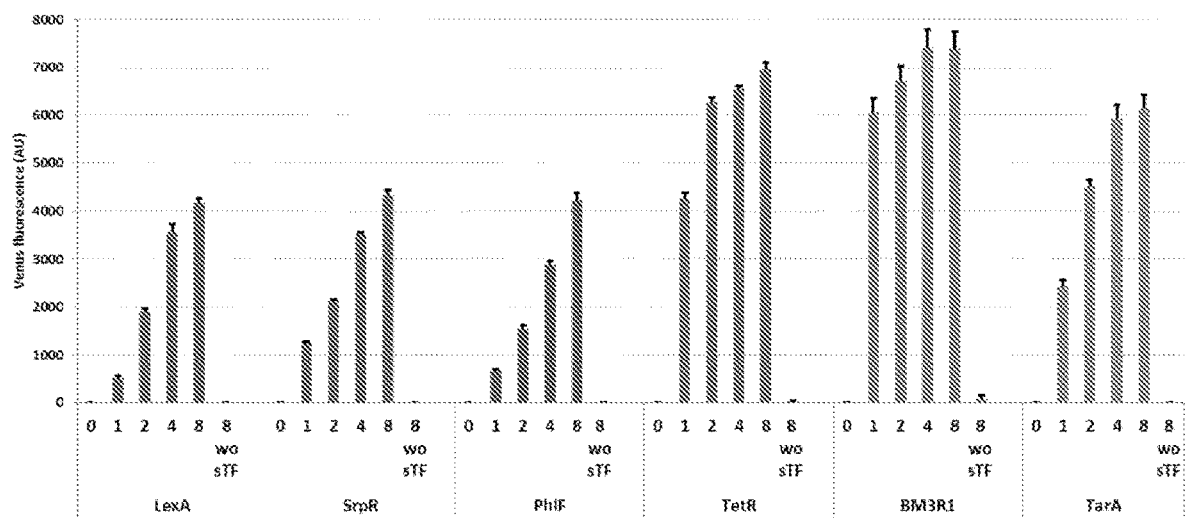

FIGS. 5A and 5B illustrate an example of a test of different versions of the sTFs and assessment of modulation of the expression systems performance in *Saccharomyces cerevisiae*.

FIG. 5A) The expression systems analogous to the one presented in FIG. 4 were constructed with following modifications to the above described system: 1) different DNA-binding proteins were used as parts of the sTFs (LexA, SrpR, PhIF, TetR, BM3R1, and TarA, see Example 1); 2) different numbers of the sTF-specific binding sites were used in the synthetic promoters of the target gene expression cassettes (the version with 8 binding sites shown in the figure); 3) the individual cassettes (the sTF expression cassette and the reporter cassette) were integrated each in a single copy into the *Saccharomyces cerevisiae* genome in two separate genomic loci (exemplified here by URA3 and LEU2); 4) the sTFs were expressed from *S. cerevisiae* core promoter, here exemplified by TDH3 core promoter; 5) the core promoter used in the reporter expression cassette was here exemplified by *S. cerevisiae* ENO1 cp.

FIG. 5b) The strains with both expression cassettes integrated were tested for level of fluorescence. Control expression systems were tested which have eight sTF-specific binding sites and which lack the sTF expression cassettes (shown as "wo sTF" in the figure). The DNA-binding proteins, SrpR, PhIF, TetR, BM3R1, and TarA, were codon-optimized to the codon usage of *Saccharomyces cerevisiae*. In most of the cases, a clear modulation of the expression level of the target gene is demonstrated, which reflects the number of sTF-specific binding sites (0-8 as specified in the figure) in the synthetic promoters of the target gene expression cassettes.

Figure 6A:
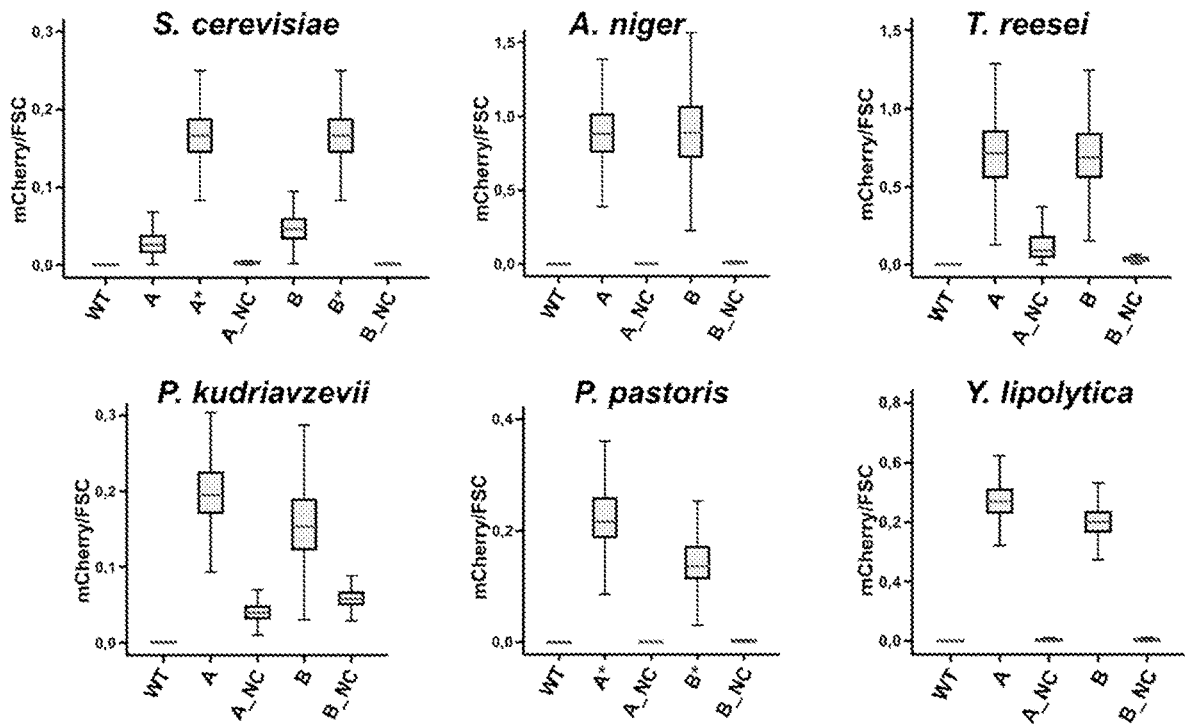
FIGS. 6A and 6B depict the analysis of the expression systems in diverse fungal hosts. Quantitative analysis of the reporter gene expression determined by fluorescence flow cytometry (6A) and by fluorometry (6B).
Figure 6B:
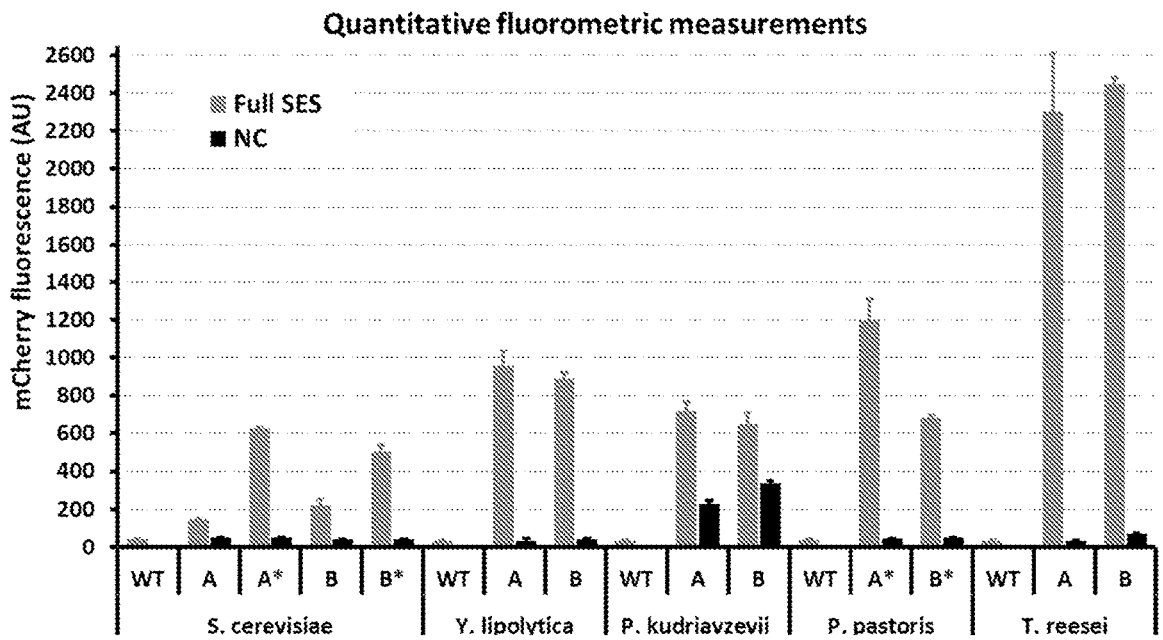

FIGS. 6A and 6B depict examples of the analysis of the expression systems in diverse fungal hosts. Quantitative analysis of the reporter gene expression determined by fluorescence flow cytometry (6A) and by fluorometry (6B). The constructed expression systems (Table 2) were integrated in a single copy into the genomes of: *Saccharomyces cerevisiae, Aspergillus niger, Trichoderma reesei, Yarrowia lipolytica, Candida krusei (Pichia kudriavzevii)*, and *Pichia pastoris (Komagataella pastoris)*. The functionality of the system in all these organisms was confirmed by fluorescent analysis of the transformed strains. The expression systems used for each organism are identical to those presented in FIG. 4. The strain identifiers in the FIGS. 6A and 6B) mean the following: "WT" represents a background strain of each expression host to which the expression systems were not transformed; "A" represents strains with a version of the expression system (integrated in the genome in single copy) shown in FIG. 4 containing 201 cp and 008 cp; "A*" represents strains with the expression system version A where the DNA-binding part of the sTF was codon-optimized to match codons frequent in *Saccharomyces cerevisiae*; "B" represents strains with a version of the expression system (integrated in the genome in single copy) shown in FIG. 4 containing 114 cp and 533 cp; "B*" represents strains with the expression system version B where the DNA-binding part of the sTF was codon-optimized to match codons frequent in *Saccharomyces cerevisiae*; "A_NC' and "B_NC" represent strains with the negative-control-versions of the expression systems (A or B) (integrated in the genome in single copy) where the sTF expression cassette was absent (deleted), leaving only the target gene expression cassette (exemplified here with 8 BS+201/114 cp+mCherry+Sc-ADH1 terminator).

FIG. 6A depicts the flow-cytometry analysis (DB FACSAria III instrument) of the mCherry expression in the hosts. It was performed on cells (for the unicellular fungi—*Saccharomyces cerevisiae, Yarrowia lipolytica, Pichia kudriavzevii, Pichia pastoris*) or spores (for the filamentous fungi—*Aspergillus niger, Trichoderma reesei*). The graphs show the fluorescence intensity (mCherry) normalized by the particle (cell/spore) size (FSC forward scatter) for 10000 cells/spores from each strain. The horizontal line (inside the grey box) represents the median value, the grey box represents the interquartile range (IQ range), the bottom of grey box represents the 25% percentile value, the top of grey box represents the 75% percentile value, and the whiskers in box plot represent values that extend from 25%/75% percentile values to the highest and lowest values which are no greater than 1.5 times the IQ range, which, together with the IQ range, represent about 99% of all measured instances (cells/spores) in these experiments.

FIG. 6B depicts an example of the analysis of the mCherry expression in the hosts. It was performed by fluorometry measurement using the Varioskan instrument (Thermo Electron Corporation), on cell/mycelium suspensions after growing 18 hours in SCD medium. The graphs show fluorescence intensity (mCherry) normalized by the optical density of cell/mycelium suspensions used for the fluorometric analysis. The columns represent average values and the error bars standard deviations from at least 3 experimental replicates.

FIGS. 7A, 7B, 7C and 7D depict examples of the analysis of the tunable expression levels in different hosts (*Pichia kudriavzevii, Aspergillus niger*, and *Trichoderma reesei*).

Figure 7A:
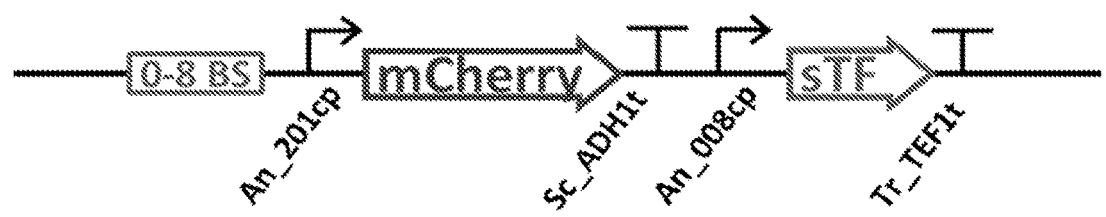
FIGS. 7A, 7B, 7C and 7D depict the analysis of the tunable expression levels in different hosts (*Pichia kudriavzevii*, *Aspergillus niger*, and *Trichoderma reesei*) by fluorescence flow cytometry and western blotting.

FIG. 7A depicts an example (shown as a scheme) of the expression system with variable number of sTF-binding sites used for modulation of reporter gene expression in *Pichia kudriavzevii* and *Aspergillus niger*. The expression system assembled in a single DNA molecule comprises two expression cassettes (analogous to those in FIG. 4): 1) sTF expression cassette, which comprises a UCP, exemplified here with the 008 cp (see Table 1), the sTF version with the DNA-binding protein, exemplified here by BM3R1, and the activation domain, exemplified here by VP16), and a terminator, exemplified here by the *Trichoderma reesei* TEF1 terminator. And 2) the target gene expression cassettes, which comprise different number of sTF specific binding sites, exemplified here by 0, 1, 2, 4, and 8 BM3R1-specific binding sites, different UCP, exemplified here by 201 cp (see Table 1), the reporter gene coding region, exemplified here by the mCherry (red fluorescent protein) coding region, and a terminator, exemplified here by the *S. cerevisiae* ADH1 terminator. The coding region of the DNA binding protein, here BM3R1, was codon-optimized to fit the codon usage of *Aspergillus niger*.

Figure 7B:
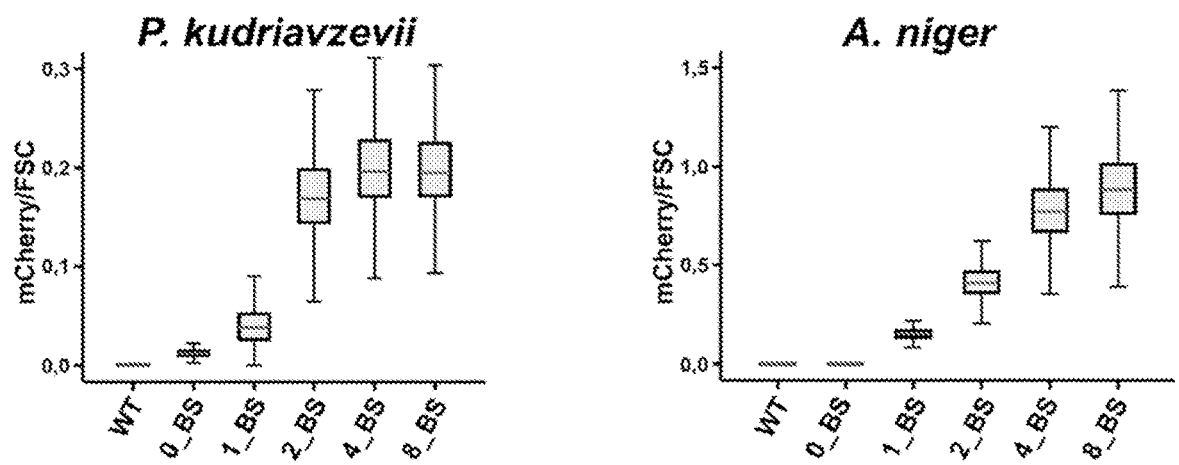

FIG. 7B depicts the flow-cytometry analysis (DB FACSAria III instrument) of the mCherry expression in *Pichia kudriavzevii* and *Aspergillus niger* containing the expression systems with variable number of sTF-binding sites (0, 1, 2, 4, and 8). It was performed on cells obtained from 18 hours cultivation in SCD medium (for *Pichia kudriavzevii*), or on spores obtained after 4 days of cultivation on PDA agar plates (*Aspergillus niger*). The graphs show fluorescence intensity (mCherry) normalized by particle (cell/spore) size (FSC forward scatter) for 10000 cells from each strain. The horizontal line (inside the grey box) represents the median value, the grey box represents the interquartile range (IQ range), the bottom of grey box represents the 25% percentile value, the top of grey box represents the 75% percentile value, and the whiskers in box plot represent values that extend from 25%/75% percentile values to the highest and lowest values which are no greater than 1.5 times the IQ range, which, together with the IQ range, represent about 99% of all measured instances (cells/spores) in these experiments.

Figure 7C:
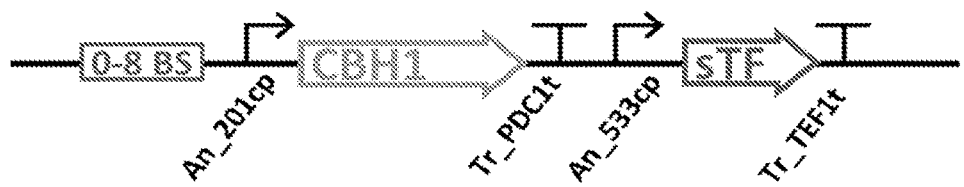

FIG. 7C depicts an example (shown as a scheme) of the expression system with variable number of sTF-binding sites used for modulation of the CBH1 protein production in *Trichoderma reesei*. The expression system assembled in a single DNA molecule comprises two expression cassettes (analogous to those in FIGS. 4 and 7A): 1) sTF expression cassette, which comprises a UCP, exemplified here with the 533 cp (see Table 1), the sTF version with the DNA-binding protein, exemplified here by BM3R1, and the activation domain, exemplified here by VP16, and a terminator, exemplified here by the *Trichoderma reesei* TEF1 terminator. And 2) the target gene expression cassettes, which comprise different number of sTF specific binding sites, exemplified here by 0, 1, 2, 4, and 8 BM3R1-specific binding sites, different UCP, exemplified here by 201 cp (see Table 1), the target gene coding region, exemplified here by the *Trichoderma reesei* CBH1 coding region (including introns occurring in the native *Trichoderma reesei* CBH1 gene), and a terminator, exemplified here by the *S. cerevisiae* ADH1 terminator. The coding region of the DNA binding protein, here BM3R1, was codon-optimized to fit the codon usage of *Aspergillus* niger.

Figure 7D:
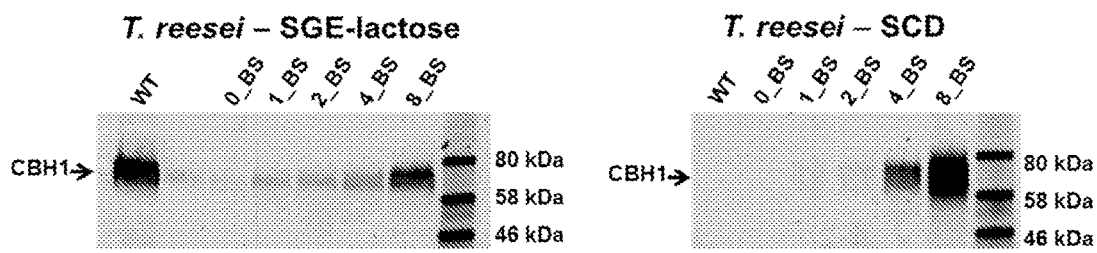

FIG. 7D depicts western blot analyses of the CBH1 protein produced by *Trichoderma reesei* to different levels with use of the expression systems with variable number of sTF-binding sites (0, 1, 2, 4, and 8). Two different culture conditions were used, 1) a medium with spent-grain extract and lactose ("SGE-lactose" in the Figure), which leads to strong upregulation of the native CBH1 gene expression (in the background strain WT), and 2) SCD ("SCD" in the Figure), which has a strong inhibitory effect on the native CBH1 gene expression (in the background strain WT). Equivalent of 15 µl of the 3-days-culture supernatant from each culture was loaded on a gel (4-20% gradient). The gel was transferred onto a nitrocellulose membrane, and the CBH1 protein was detected with specific (mouse) anti-CBH1 primary antibody (and anti-mouse-IR680-conjugated secondary antibody), and the visualization of the signal was performed on the Odyssey CLx Imaging System instrument (LI-COR Biosciences).

Figure 8A:
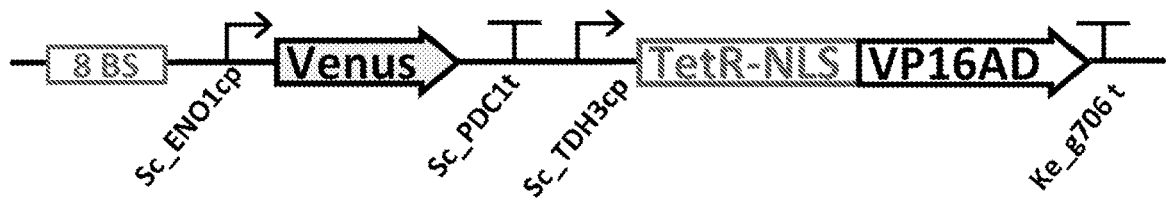
FIGS. 8A and 8B depict the scheme of the expression system (8A) and the analysis of a reporter gene expression in *Kazachstania exigua* (8B) by quantitative real-time PCR (qPCR).
Figure 8B:
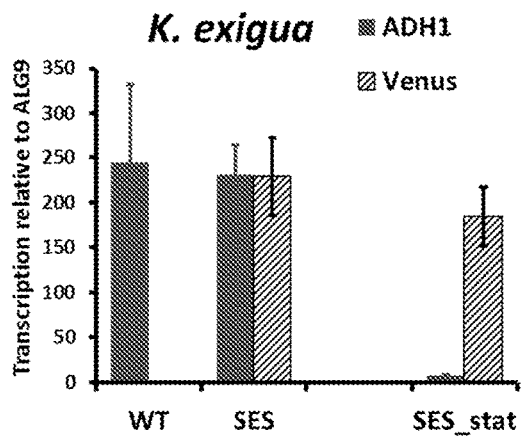

FIGS. 8A and 8B depict the scheme of the expression system (8A) and the analysis of a reporter gene expression in *Kazachstania exigua* (8B).

FIG. 8A depicts an example (shown as a scheme) of the expression system used for *Kazachstania exigua*. The expression system assembled in a single DNA molecule comprises two expression cassettes (Table 3): 1) sTF expression cassette, which comprises a UCP, exemplified here with the Sc-TDH3 cp (see Table 1), the sTF version with the DNA-binding protein, exemplified here by TetR, and the activation domain, exemplified here by VP16, and a terminator, exemplified here by the *Kazachstania exigua* g706 terminator. And 2) the target gene expression cassette comprises a number of sTF specific binding sites, exemplified here by eight TetR-specific binding sites, different UCP, exemplified here by Sc-ENO1 cp (see Table 1), the reporter gene coding region, exemplified here by the Venus (yellow fluorescent protein) coding region, and a terminator exemplified here by the *S. cerevisiae* PDC1 terminator. The coding region of the DNA binding protein, here TetR, and the coding region of the target gene, here Venus reporter, were codon-optimized to fit the codon usage of *Saccharomyces cerevisiae*.

FIG. 8B depicts an example of an analysis of the Venus expression in *Kazachstania exigua* containing the expression system (described in FIG. 8A, Table 3). The expression cassette was integrated into the genome of the background strain of *Kazachstania exigua* ("WT" in the Figure), replacing the native g706 coding region, to obtain the tested strain ("SES" in the Figure). The two strains (WT and SES) were cultivated in the SCD medium for 10 hours, and the SES strain for 22 to reach the stationary phase ("SES_stat" in the Figure). The transcription of Venus and ADH1 genes were analysed by qPCR, with the ALG9 gene being the normalization control for expression quantification. The columns represent the average values and the error bars the standard deviations from 3 experimental replicates.

FIGS. 9A, 9B, 9C and 9D depict the analysis of the protein production in diverse expression hosts (*Trichoderma reesei* and *Pichia pastoris*) containing the expression system.

Figure 9A:
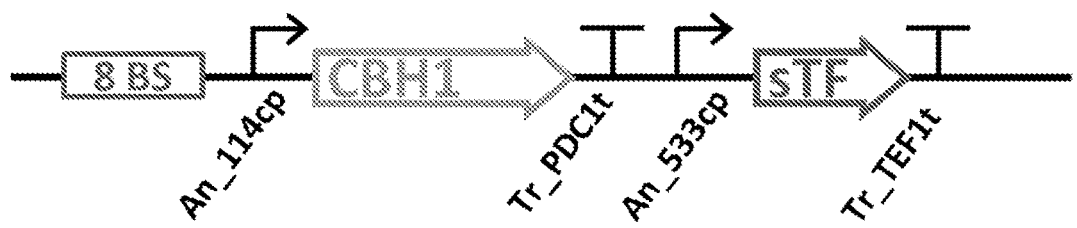
FIGS. 9A, 9B, 9C and 9D depict the analysis of the protein production in diverse expression hosts (*Trichoderma reesei* and *Pichia pastoris*) containing the expression system.

FIG. 9A depicts an example (shown as a scheme) of the expression system for the CBH1 protein production in *Trichoderma reesei*. The expression system assembled in a single DNA molecule comprises two expression cassettes (analogous to those in FIGS. 4 and 7C): 1) sTF expression cassette, which comprises a UCP, exemplified here with the 533 cp (see Table 1), the sTF version with the DNA-binding protein, exemplified here by BM3R1, and the activation domain, exemplified here by VP16, and a terminator, exemplified here by the *Trichoderma reesei* TEF1 terminator. And 2) the target gene expression cassettes, which comprise a number of sTF specific binding sites, exemplified here by eight BM3R1-specific binding sites, different UCP, exemplified here by 114 cp (see Table 1), the target gene coding region, exemplified here by the *Trichoderma reesei* CBH1 coding region (including introns occurring in the native *Trichoderma reesei* CBH1 coding region), and a terminator, exemplified here by the *Trichoderma reesei* PDC1 terminator. The coding region of the DNA binding protein, here BM3R1, was codon-optimized to fit the codon usage of *Aspergillus* niger.

Figure 9B:
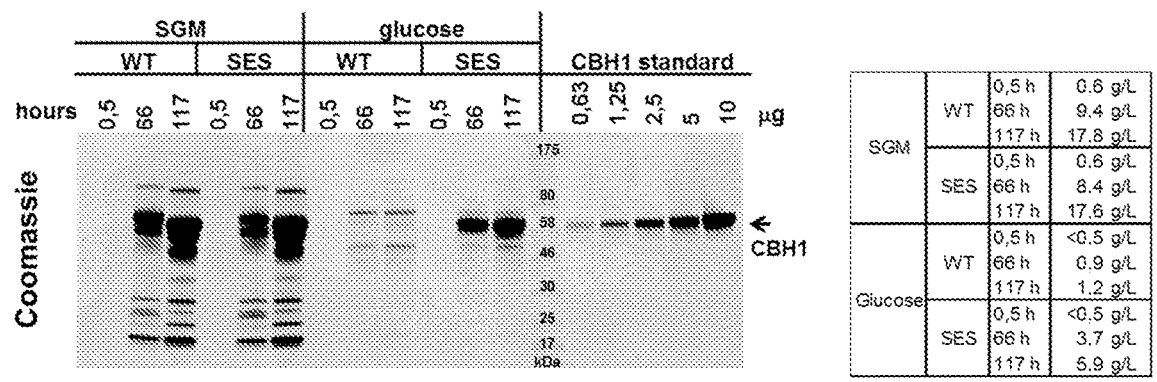
Figure 9B:
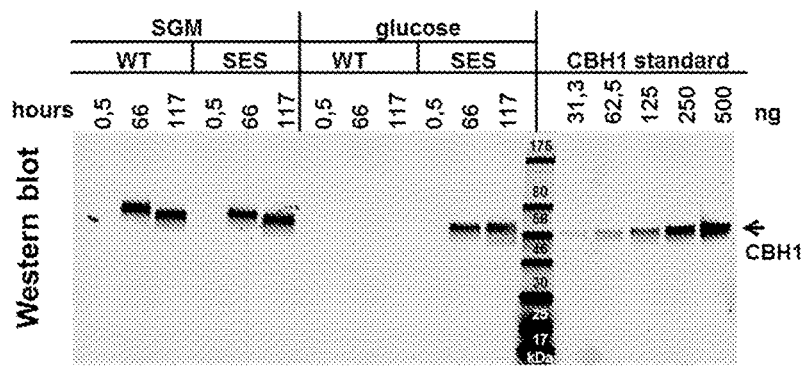

FIG. 9B depicts an example of an analysis of the production of CBH1 in *Trichoderma reesei* containing the expression system (described in FIG. 9A). The background strain of *Trichoderma reesei* ("WT" in the Figure) was a mutant strain harboring multiple deletions of the genes encoding 8 diverse proteases. The expression cassette was integrated into the genome of the background strain to obtain the tested strain ("SES" in the Figure). The two strains (WT and SES) were cultivated in the bioreactor (fermentor) in two different conditions: 1) in a medium containing spent grain, spent-grain extract, and lactose ("SGM" in the Figure) which leads to a strong upregulation of the native CBH1 gene expression (in the background strain WT) and other cellulolytic genes expression (in both strains), and 2) in a medium containing yeast extract and glucose ("glucose" in the Figure) which has a strong inhibitory effect on the native CBH1 gene expression (in the background strain WT) and other cellulolytic genes expression (in both strains). The supernatants from these cultures were analyzed by the SDS-PAGE (SDS-polyacrylamide gel electrophoresis) analysis, for total protein content (Coomassie) and for the specific CBH1 content (western blot). For the total protein content analysis, equivalent of 1.5 µl of different time-points culture supernatants, and the range of purified CBH1 protein (loading control), were loaded on a gel (4-20% gradient), and the gel was stained with colloidal coomassie (PageBlue Protein Staining Solution; Thermo Fisher Scientific). For the CBH1 specific analysis, equivalent of 0,075 µl of different time-points culture supernatants, and the range of purified CBH1 protein (loading control), were loaded on a gel (4-20% gradient), and the CBH1 protein (after transfer onto a nitrocellulose membrane) was detected with specific (mouse) anti-CBH1 primary antibody (and anti-mouse-IR680-conjugated secondary antibody). For both analyses, the visualization of the signal was performed on the Odyssey CLx Imaging System instrument (LI-COR Biosciences). The protein concentration (in the culture supernatants) was estimated from the range of purified CBH1 loaded on each gel, and the values are shown in the Figure.

Figure 9C:
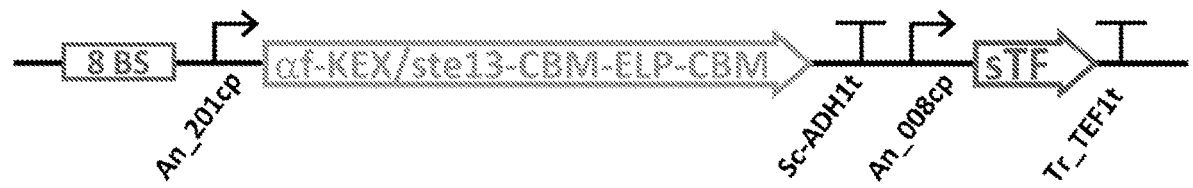

FIG. 9C depicts an example (shown as a scheme) of the expression system used for *Pichia pastoris* for production of a protein product. The expression system assembled in a single DNA molecule comprises two expression cassettes (analogous to those in FIG. 4): 1) sTF expression cassette, which comprises a UCP, exemplified here with the 008 cp (see Table 1), the sTF version with the DNA-binding protein, exemplified here by BM3R1, and the activation domain, exemplified here by VP16, and a terminator, exemplified here by the *Trichoderma reesei* TEF1 terminator. And 2) the target gene expression cassette comprises a number of sTF specific binding sites, exemplified here by eight BM3R1-specific binding sites, different UCP, exemplified here by 201 cp (see Table 1), the target gene coding region, exemplified here by the coding region of the fusion protein comprising *S. cerevisiae* secretion signal (α-factor), KEX/spe13 protease cleavage site, carbohydrate-binding module (CBM), elastin-like protein (ELP5), and another CBM, and a terminator exemplified here by the *S. cerevisiae* ADH1 terminator. The coding region of the DNA binding protein, here BM3R1, was codon-optimized to fit the codon usage of *Saccharomyces cerevisiae*.

Figure 9D:
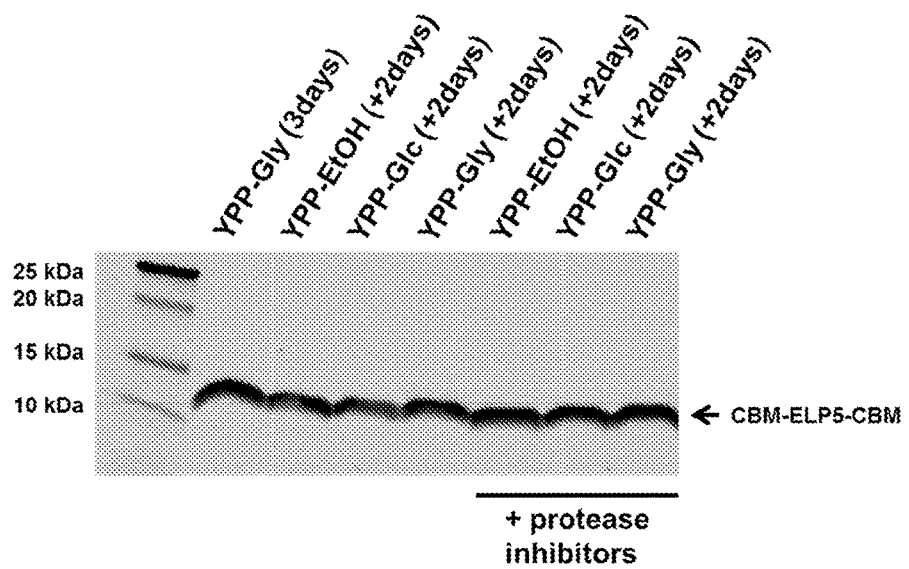

FIG. 9D depicts an analysis of the production of CBM-ELP5-CBM in *Pichia pastoris* containing the expression system (described in FIG. 9C). The strain was cultivated in diverse conditions, and the supernatants from these cultures were analyzed by the western blot. Equivalent of 22.5 µl of the culture supernatants were loaded on a gel (4-20% gradient), and the CBM-ELP5-CBM protein (after transfer onto a nitrocellulose membrane) was detected with specific (mouse) anti-CBM primary antibody (and anti-mouse-IR680-conjugated secondary antibody). The visualization of the signal was performed on the Odyssey CLx Imaging System instrument (LI-COR Biosciences).

TABLE 1

Selection of core promoters tested in *Saccharomyces cerevisiae* and other organisms. The bolded sequences are the 3'-flanking regions added to the core promoter sequences for screening or cloning purposes. The ATG (start codon) is underlined. Sc—*Saccharomyces cerevisiae* origin; An—*Aspergillus niger* origin; Tr—*Trichoderma reesei* origin; At—*Arabidopsis thaliana* origin; Cr—*Chlamydomonas reinhardtii* origin; Mm—*Mus musculus* origin DNA sequences of the selected UCPs and other CPs used for constructing the expression systems

| | |
|---|---|
| Sc-THI4cp | ATCATGAAATTGATTTTTTGATTTTCAATTTATGAACTACCCAGATATATAAATATTGGAATAAATTGTGTATTAA GTAGTCGGGAAATATCTTTTATGTTCTCTTTCTTATCATCTAGAAATAATAAATCACAACCAAAAAAATCAACTAA CTTAATTAAAATG (SEQ ID NO: 1) |
| Sc-TEF1cp | CTCTTTCGATGACCTCCCATTGATATTTAAGTTAATAAACGGTCTTCAATTTCTCAAGTTTCAGTTTCATTTTTCT TGTTCTATTACAACTTTTTTTACTTCTTGCTCATTAGAAAGAAAGCATAGCAATCTAATCTAAGTTTTAATTAAAA TG (SEQ ID NO: 2) |
| Sc-TDH3cp | AGCTGAAAAAAAAGGTTGAAACCAGTTCCCTGAAATTATTCCCCTACTTGACTAATAAGTATATAAAGACGGTA GGTATTGATTGTAATTCTGTAAATCTATTTCTTAAACTTCTTAAATTCTACTTTTATAGTTAGTCTTTTTTTTAGTT TTAAAACACCAAGAACTTAGTTTCGAATAAACACACATAATTAATTAAAATG (SEQ ID NO: 3) |
| Sc-ENO1cp | TCTCCCCGGAAACTGTGGCCTTTTCTGGCACACATGATCTCCACGATTTCAACATATAAATAGCTTTTGATAAT GGCAATATTAATCAAATTTATTTTACTTCTTTCTTGTAACATCTCTCTTGTAATCCCTTATTCCTTCTAGCTATTTT TCATAAAAAACCAAGCAACTGCTTATCAACACACAAACACTTAATTAAAATG (SEQ ID NO: 4) |
| Sc-PGK1cp | AAGGGGGTGGTTTAGTTTAGTAGAACCTCGTGAAACTTACATTTACATATATATAAACTTGCATAAATTGGTCAA TGCAAGAAATACATATTTGGTCTTTTCTAATTCGTAGTTTTTCAAGTTCTTAGATGCTTTCTTTTTCTCTTTTTAC AGATCATCAAGGAAGTAATTATCTACTTTTTACAACAAATTAATTAAAATG (SEQ ID NO: 5) |
| An-201205cp (201cp) | TTCTCTTTTCTTAAGAATATGTTCAAAGACTAGGATGGATAAATGGGGTATATAAAGCACCCTGACTCCCTTCCT CCAAGTTCTATCTAACCAGCCATCCTACACTCTACATATCCACACCAATCTACTACAATTATTAATTAAAATG (SEQ ID NO: 6) |
| An-53301cp (533cp) | CGCCCCAAGAGAGCTGAAGATGCTGAGTAGGGTTGTCCAGGCAGCACATATATAAGATGCTTCGTCCCCTCC CATCGAGTCCTTCTTTTCTCTCTCATCAATCACTCTACTTCCTACTCTACCTTAAACTCTTCACTACTTCATAC ATTAATTAAAATG (SEQ ID NO: 7) |
| An-205017cp | TATAGTACTATTGATTTAGTATTGTTGTTGGATGTGCTGGTAGGTGTGTAGTATATATAGGAGATAGTAGAGGC AGATGATGATGATGGTACTATTTTGAATCACCTCAAACGATACTATTCGCATCTTTGATAAAGATATCAAGAAAC CAGAACAATCATTACTACTCTCCATAAGGATATATATATACTTTACATCTTAATTAAAATG (SEQ ID NO: 8) |
| An-00850cp (008cp) | AACCCAAAGTAATAAGTCTGTAGTAATTGGTCTCGCCCTGAATTCCAAACTATAAATCAACCACTTTCCCTCCT CCCCCCCGCCCCCACTTGGTCGATTCTTCGTTTTCTCTCTACCTTCTTTCTATTCGGTTTTCTTCTTCTTTTATTT TCCCTCTCCCATCAATCAAATTCATATTTGAAAAAAATTAACATTAATTAAAATG (SEQ ID NO: 9) |
| An-1114556cp | GGGGCGGAAACTTGAAACTGGACGCCTTGTGAACGGCGTATGTGGTATATAAGGAACCAAGTCCCGCTGTAG TCTTCGGTTCATCAGACCCAGCACAGCACAGCAACACAACATTACAGCATGCATAGCAAGCACTTCTCTATATTTCTA CACATCACAGCACATTTCTATACAGTTTACGTCTAATTATCTCCTGTTAATTAAAATG (SEQ ID NO: 10) |
| An-1147651cp (114cp) | GCCCTGCAGTGCCTGATCACCTTATCAAGTGGCCAAATATCCCACTATAAAAGGCTTGGGAACCCCTCGTTCT GTCTTACCTTCTATCATCTTACCAAATCCACTCCTCTTCCTTCATACATCAATCTTACCAATCAACTACCTCTACA ACTCCAATACACTTAATTAAAATG (SEQ ID NO: 11) |
| An-1178623cp | GGCTACTCGGGTTTTAAGCCGTCTTAAAAGCCGACACGAATTAGTTATAAAAGACTCTGTACTTGAGCAGGATA TTCCTTCATTCTTTTCATTTAGATTGATATCGAATTCATTCTACAAGGATCGGATACTCTTCCATCCTTTATTTTG TCTCTGTGAATCAAACTTAATTAAAATG (SEQ ID NO: 12) |
| An-57241cp | AGGTAATGAATATTGGTTGCTGGCGGGCTGATCTTCTCCCGACACGTCTATATAAACTGGTCACCTTCTGGCC CTTCCTTTCTATCTCTTCCTTCTCATCATCAGTCTCAAACAAGCCTCTTTCTCTCCTACCTTCACTCTCCACTTTC TCCTTTCGAAAGGGATAAAACTCCTCCTCATTCTCACCTATATATACCTTGTGCTTTAATTAAAATG (SEQ ID NO: 13) |
| An-06590cp | GATTTCTAGAAATTTCTGCCCTTTACTTGCCTTCCCTCTTTGTCAACAAATATAAAGAGACTCCAATTCCCCTTC TCTGATTTCCAACATTTTTCATTCTCCACTTCAGAACCATCTGAAGGAGCTTGGCTGTCTCGCTTCTTCTTCTTT CCTTCTTTACTAACATCCCTACCCCTCCTTAGAAAACCAAGTCTCTCCTCCTTTAATTAAAATG (SEQ ID NO: 14) |
| An-1141688cp | ACTTGGATGATGAGGAGTTGATCGAGGTCAATGAGGAGAGGCTTGCAAGTATAAGAAGAGACTGCTCGACC AGCAGAATGGATCTTCTTGTTCATCAACCAAGAGTCCAAGGCTTCTTTGTCTGGTTCTATCTCTTCTCCGAACT CTCTTGCTTGACATTCTCTTAATTAAAATG (SEQ ID NO: 15) |
| Tr-123979cp | TAGCCAGCAGTGAAGAAGAGGGGAAGAAGATAAACCTGTAGGTTGGACAGAGTGTATAAAAGGGAGGGCTGT GCCCAACGAGGAGCGAGATTAACTTTGGATTTGGAGCAGAACAATATTGGAATCACAAGAAGAAGGATCTCTG TCTTTAATTAAAATG (SEQ ID NO: 16) |
| Tr-112258cp | TAGCCACATCCTTGGAGATCAGTTGCAGTCTATTCATTCAGGCTCAACATATAAAGATGGGATACTTCCAACAG ATGATAGTTGTCAAACAACCTCTTTGATCCTACACAATTTGGCCCAAGACACACAAGACGCTCACATCTCCTAC CTAACCAAACAAAGAAAAAAACATCCACCAACTTAATTAAAATG (SEQ ID NO: 17) |
| Tr-123236cp | ATCTTACAAAGTTGCTTGGCAGTAAACCGTGCAATGGACACCAGGTATAAAGTCAGTGATATCCTCCCCGAATT CAAAGTTTCATCACCAAGCTCCTCAATCAACTCTACTTGAACAATACTACAAACAACCAAACCTCATTCAACAAC TTAATTAAAATG (SEQ ID NO: 18) |

TABLE 1-continued

Selection of core promoters tested in *Saccharomyces cerevisiae* and other organisms. The bolded sequences are the 3'-flanking regions added to the core promoter sequences for screening or cloning purposes. The ATG (start codon) is underlined. Sc—*Saccharomyces cerevisiae* origin; An—*Aspergillus niger* origin; Tr—*Trichoderma reesei* origin; At—*Arabidopsis thaliana* origin; Cr—*Chlamydomonas reinhardtii* origin; Mm—*Mus musculus* origin DNA sequences of the selected UCPs and other CPs used for constructing the expression systems

| | |
|---|---|
| Tr-123989cp | TAAACGGAATGAGCTAGTAGGCAAAGTCAGCGAATGTGTATATATAAAGGTTCGAGGTCCGTGCCTCCCTCAT GCTCTCCCCATCTACTCATCAACTCAGATCCTCCAGGAGACTTGTACACCATCTTTTGAGGCACAGAAACCCA ATAGTCAACCGCGGACTTAATTAAAATG (SEQ ID NO: 19) |
| Tr-119989cp | AACAGCCTGCGAGAGCTGGAAGATGAAGAGGGCCAGAAAAAAAGTATAAAGAAGACCTCGATTCCCGCCAT CCAACAATCTTTTCCATCCTCATCAGCACACTCATCTACAACCATCACCACATTCACTCAACTCCTCTTTCTCAA CTCTCCAAACACAAACATTCTTTGTTGAATACCAACCATCACCACTTAATTAAAATG (SEQ ID NO: 20) |
| Tr-123232cp | GGTCTGGATGAAACGTCTTGGCCAAATCGTGATCGATTGATACTCGCATCTATAAGATGGCACAGATCGACTC TTGATTCACAGACATCCGTCAGCCCTCAAGCCGTTTGCAAGTCCACAAACACAAGCACAAGCATATTAATTAA AATG (SEQ ID NO: 21) |
| Tr-73638cp | CCGGCACAAATCAGGAGCAACAGGCACTGCAAAATGACCTGGCAGTATATATAGACCTGACCGTATGAGTCTA TTGTAGACATTCTAGCTAAGAGATCCGAGCCTAGTTCATAATACAGTAGTTGAGTTCATAGCAACTTCACTCTC TAGCTGAACAAATTATCTTTAATTAAAATG (SEQ ID NO: 22) |
| Tr-123818cp | GAGACGAGGCAAGCTTGATGAGGCCAAATTATCCGTCAACTGTCTTATAAAGGAGCCCATGCCAAACCCCCC CTAAAGACTCAAGAAGCCAAACCTGAACAACCCCAGCACCTGAACAGTCATACAACCCCTCCAAGCCCAAAAG ACACAACAACTCCTACTAGCTGAAGCAAGAAGTTAATTAAAATG (SEQ ID NO: 23) |
| Tr-123979cp | CAGCAGTGAAGAAGAGGGGAAGAAGATAAACCTGTAGGTTGGACAGAGTGTATAAAAGGGAGGGCTGTGCCC AACGAGGAGCGAGATTAACTTTGGATTTGGAGCAGAACAATATTGGAATCACAAGAAGAAGGATCTCTGTCTT TAATTAAAATG (SEQ ID NO: 24) |
| Tr-69465cp | GAAAAATGGTGAGGAGATCTGCCTTCGAGTGCGTGTAGAAAAATGTATATAAGGATGTGTTTCACTCAACTTGT CTTAAGAATCGGTTCTCTAGCCGCGCTTTCAATTACTTCGAGACTTTCGCTTAAAATCGCCCTGCCATTTAATT AAAATG (SEQ ID NO: 25) |
| Tr-49976cp | TGCCCCTGGCGTTGCAAGCCGCGTACAACTGCCCTTTTACCTAGGTATAAAAGACCTGTAGTAACCAACTACT ATTGCAATTCTTCTTCACGTGGGCATCTATTCGTATCTTACACAAGGGCGCTGCAACTAATTGACTTGATCTTC CATCTCGTGTCTTGCTTGTAACCATTTAATTAAAATG (SEQ ID NO: 26) |
| Tr-123946cp | CTGTTAGGCTGTGAGTTATAAAGGTTGATGGATTGGGTCGAGGTTGTCAATGTCAGAGCATCTTACCTCTCAC GCTTCAATCTTACCTACACGCTTCCTCTCAATCCTTGAACACCAATTGTTGCTCTAGCGCCTATCCTTCACTCAT CACTCGCCTCGTACACTAAACTCTTCATCCCGAACAGACACGGCTTTAATTAAAATG (SEQ ID NO: 27) |
| At-CRA1cp | AAGTCATAAATAGCAATTTAAGTGAAGTGTAAATTGTACATAGTCGACTCTATATACCTGGTTCTTATCTCATTC AATTTATCCTCAACAACTTTAATAGAAAAATATCAAATAAATTCCCTATAAATAGCTTCACATAATGCAAGTGAGA AACCACAAAAAGTAAGAAATATAAGATTAATTAAAATG (SEQ ID NO: 28) |
| At-RPL41Dcp | ATCCCCTCTGGCAAATTCTTATCCATTTGGGTTTTATTGGGCTTTTGAAATAATAAAGCCCATTAAGTTAGTTAC TAGGGTTTTGTTGTTGTTTAAAGGAGGAATAAGAGCGTAAGCTACAAAATCTTTCTATTCATCTCCGCCGCTCC TCATCCTGTAAAGCTAAACAAATAATCAGAGGAACGAAGGAGACAGCTTCTGCTTAATTAAAATG (SEQ ID NO: 29) |
| At-ATTI7cp | GAATTTGTGGTTCTCGTGAAGTCGTGATAATAGTTTGTCCAAGCGATAAATATAAAATAGTATTGCACCTCAAC AAGTGTTAAGCATGCAAATCCATTTACGCATACATATTAACTCCGAGTGAAATATAAATATTAGAGAGTAGAGA CAGAGAAAAGACAGAGACAAAGTTAATTAAAATG (SEQ ID NO: 30) |
| At-THI1cp | ATCGTTACTTTCCATTGATGGCTAAAAATTAAAATAATCACGATAAATATTAATAATACAAAAAACAATTAAAATA ACAAAAAAGATCAAAAATTCTCTAACCCTTCATTCCTTATCTCTGACGTGGCCATCAATCTTCAGATTTTCTTC TTCTTCTAATTTAAATACTCAACAACCACTCTTCACTTCACCATCAGCATCACTAAACTCGAACCCTAAAGTTAA TTAAAATG (SEQ ID NO: 31) |
| At-MT2Bcp | GTGGACAAAGATCGTTGACACGTGGACGGTCTACAAATTCTAATTTTGCCTATAAATATCAAAGCTCCTGAATA TGTAAGTTTCATTCACTGATTATCGTTTAAGGCAAATTAAGATCATCTTCATAAATCTTCTCAGATCTCTTCCAAT TTTCTTTAATTAAAATG (SEQ ID NO: 32) |
| At-TCTP1cp | CCAAAATTGTAATTTACCGAGAATTGTAAATTTACCTGAAAACCCTACGCTATAGTTTCGACTATAAATACCAAA CTTAGGACCTCACTTCAGAATCCCCTCGTCGCTGCGTCTCTCTCCCGCAACCTTCGATTTTCGTTTATTCGCAT CCATCGGAGAGAGAAAACAATCAATTAATTAAAATG (SEQ ID NO: 33) |
| At-RPL26Acp | GAATTAACTTTTACTAGGCCAGAAGTGTAGCTAACATAGAAGAGGCCCATTATAAAACTCTTTAAAATCAAAATC TAAAACAGGCCCAGCCCATTCATAACAAAGCCCTAATATATCGAGTAAACCTAGCTCCACTCAAAACCTAACTA TATAACCTTCACACACACTCATAACCTCTTCCTCATCCCCTTAAAAAACCCTAAGAGTAGAGACTCTCTCAATCC CGTTAATTAAAATG (SEQ ID NO: 34) |
| At-MED37Ecp | ACCAATTTTTGACCGTCCGATGGAAACTCTAGCCTCAACCCAAAACTCTATATAAAGAAATCTTTTCCTTCGTTA TTGCTTACCAAATACAAACCCTAGCCGCCTTATTCGTCTTCTTCGTTCTCTAGTTTTTTCCTCAGTCTCTGTTCT TAGATCCCTTGTAGTTTCCAAATCTTTTTAATTAAAATG (SEQ ID NO: 35) |

TABLE 1-continued

Selection of core promoters tested in *Saccharomyces cerevisiae* and other organisms. The bolded sequences are the 3'-flanking regions added to the core promoter sequences for screening or cloning purposes. The ATG (start codon) is underlined. Sc—*Saccharomyces cerevisiae* origin; An—*Aspergillus niger* origin; Tr—*Trichoderma reesei* origin; At—*Arabidopsis thaliana* origin; Cr—*Chlamydomonas reinhardtii* origin; Mm—*Mus musculus* origin DNA sequences of the selected UCPs and other CPs used for constructing the expression systems

| | |
|---|---|
| At-AT1G15270cp | ATACACTTTCAGAGCCCATTTAATAGGTTGCGTTGTTACTACGAACTCATTATAAATATGAACCGTAGCCCCAAT CAGAGAGATTCGATACCGTCTGCAACTCTCAGCTACTTTTTCCCCAATTTTGAGCTCAACATCGAACCCTAGCT CAACTTAATTAAAATG (SEQ ID NO: 36) |
| At-FKBP12cp | TCTGCTTCTTAATTCGGTCTGGTACAGTATTATATTATCCACCTTTGAGAAAGAATAAATAATGGGCCTAAATTT CATCGAATTGGGTTTTGGATTATTGTTAGGCCCAGATAGGGTTTAGATCAAACAGCATGATAATTGATAAATAA CAAAATATATAGGCAAAAGCTACTCCGAGATTCGAAGCTGCAAAGAACGCGAAACAGTGAGAGAGACAGAGA GAATTAATTAAAATG (SEQ ID NO: 37) |
| At-AT4G25140cp | CAATTGCATGATGTCTCCATTGACACGTGACTTCTCGTCTCCTTTCTTAATATATCTAACAAACACTCCTACCTC TTCCAAAATATATACACATCTTTTTGATCAATCTCTCATTCAAAATCTCATTCTCTCTAGTAAACAAGTTAATTAA AATG (SEQ ID NO: 38) |
| At-DRT112cp | ATGCCATGTCACGACACAGTATCTAAAATCAACCAATCACAACGCGTCTTTATAGATAACTTGTTTTTTTATGGA GTTTGCTTTTAGAGCCATCCATTGTCCTATCTCACTTTCTCTCTTTCACCACATAAAAACTCATAAACTCGATCG AACCAAAGCTAAACGAAAAACTTAAAACCCAAATCTTATCACTACTCTAAAAGATTAATTAAAATG (SEQ ID NO: 39) |
| At-AT1G13930 | TTTTCACATTTACGTCTACAATCACAATGTATGTTATTTAGAACAATAATTATAGTGGCTTAAAAATCATTAATGA AAGTAGATAATAGTATACTTTTTCTTTTTCTTTGTGTGGCCAACATATCCATTTTCTAGTCTATATATACACATAT CCATCTCTTAACTCTTCCATCCAAAAAAAACAAAACAAAAAATTATATTCAAGAGAAATTAATTAAAATG (SEQ ID NO: 40) |
| At-RPL14Bcp | TATTTAGTAAAGATAGGCCCAAACCACAAAACCCTAGAATGAAGATTATATATAGTGCAAAACCTAATCGATTTT TTCCTCTGCTGTCGCTCGTCTACATTTACACTCGGAGCTTAGACCTTCCAATCTACCGTTAATTAAAATG SEQ ID NO: 41) |
| At-PDF2cp | TTAAAAATGCAATTCTCTAATAGACTATCAAATATCCCGATACCTCTTTATATAGTGCCATCTTCATCCTTAGTAA TGTACACACACACACATAACACTTATTTCCAACTCTGTCTCTCAATTTTCTTTCTCTTTTAATTAAAATG (SEQ ID NO: 42) |
| Cr-eIF-5Acp | CGACGAAGGGATGTCTCCGCAAGGCAAGTATATAACGGCTAGCAACGTATGCCTTAGCATAGTAGAGCAATTA GTTGTCTATGTGCCTCGGTGCAAGCGCACACGCCGGGAATAATGCGGCATGGGGGCTTCGTTGGCCCCATG CGAGCCCCCAGGAAGAAAAGTCGCGCGGCGCCCGTATTCTGCCCTCTTGCTGTGCCAACCTCCTAGTCGCTT CTTCGCACTTTTTAATTAAAATG (SEQ ID NO: 43) |
| Cr-RPS27E1cp | GGATGGTGCCAAGGGTCCGGGTCACCGAGTAGCATTGGCCCACTCTAAGATATAAGTTGAGCCGTGTTTAAC TTGTTGCAACATCAGGCCTCGCGCGCAACGTCAGGAATGGCTGCATGGGGCCACCGTACCATGGCGCGGAG GGAGGGTATTGTCGCTGAGCGCGACTCAGAGCTCCCTCTCCTTTTGCTGACCGCGGAGCCTGCCCCTCTTAA TTAAAATG (SEQ ID NO: 44) |
| Cr-RPS8cp | CTGTTCTGGACGGGTCCAATGAGCCCGCTCTAAATAAACGTCTAGGAGAAGCAGTTAACCTAAGGGAAGGTG GCAGCAGGGGAGAGAGGGAGAGAGGGAGCGGGTCCATTGCTCCAGGGCGAGCCGGAATGGGGCCGGCGC TGCCTGGGCTTTGTCCGGCTGCAGACACACGGCTCTTTCTCTTTCCATTCCTTAGGGGCTGGGAACGGTTAAT TAAAATG (SEQ ID NO: 45) |
| Cr-RPS3Acp | CCGAACTTGCTCTCGGTGTCATATTGCACCATCCCATCTTGTATAACCGATATAACATAGCTTCGAGTGTGCCG ATAAATTATTGTGAGGGCGTCGGGGGCGAGCTGAGGGAAATGGAGGGGGCACTCATCTCGGCCGCCCCTC CCATCGCGACCTCGGCGCTCAAGCGGGGGTCCCGCACTCGCTTCGGTCTCTTTTGGTCAGCAGCCGTTTGTT GACTACCGTTAATTAAAATG (SEQ ID NO: 46) |
| Cr-RPL17cp | AAGCGGACAGAAATTTAGTTCAGGAAGAATTGTCAGATTTGCTACTGGCATATAATTTTTTCTGCAGGGTCTGG CGTGGAAGAATGCCAAATGGCGCGGAGCTGGCTGCATGGGGCGCCACCTCCCAGCAAGGGCCACCACTGCA ACCTGCTCTTTCTCTTTCGTCGCGCCTTGCACGTAGCGTTAATTAATTAAAATG (SEQ ID NO: 47) |
| Cr-RPL19cp | AGAACGCGCCTAGTACTCATGCCACGAGAGTTTCATCATTCCAGCATGCATAATAAATTTGTCACTCAGGCAG AGCATTTGCGGGGCGCGCAATGTTTAGCGGGGCCCAAAGTCGCCATCGCGGTCGCGCCCCCATGCAGCGTT CCACCCTGGCTTTCAGGCGCGGGCGCACCTGGACTATCCCTTTCTTTGCGTCGTCCGCTTGCAACAGATTA ATTAAAATG (SEQ ID NO: 48) |
| Cr-RPS24cp | AGCGAGCGAACTAGTCTCGCGCCCCGGCCCCCCCGTCGCCAACAGACCGCTATAACCAAGTAATTTTGTGTG GCTTTATTTGTATTGCTAAAAACCCCCGAGCGGGGTGAGCCCAAGACAAGAAACGAAGGCGGCCCCCTCCTG GAGCAATGGGCGTCTGAGAGACGGGCAAGACCAGGGAGAGTCCCAGCCTCCTCCCTCTTTCTCTTGGCAC ACTTAATTAAAATG (SEQ ID NO: 49) |
| Cr-RPS15cp | TCTAGGAGGGGTTTTCCCTTGTTTAGCCCTATATAACGTAAAGCTCACACTTTGAATGAGCAACATAAATTATAT TTAGTGCGAAAGCCGGCTATGAAAATGGACATGGGGATCGCGATGGGCGCCCCCGCGCCCTGGCGGCGGTG TGCACAGGAGCGAGGCCCTCGCCTGCTCCTTCCTCTTTCTCTCGCCGTCAGGCTCGTAGTTTCAAAGTTAAT TAAAATG (SEQ ID NO: 50) |

TABLE 1-continued

Selection of core promoters tested in *Saccharomyces cerevisiae* and other organisms. The bolded sequences are the 3'-flanking regions added to the core promoter sequences for screening or cloning purposes. The ATG (start codon) is underlined. Sc—*Saccharomyces cerevisiae* origin; An—*Aspergillus niger* origin; Tr—*Trichoderma reesei* origin; At—*Arabidopsis thaliana* origin; Cr—*Chlamydomonas reinhardtii* origin; Mm—*Mus musculus* origin DNA sequences of the selected UCPs and other CPs used for constructing the expression systems

| | |
|---|---|
| Cr-ATPC cp | CGTGCAAGCTACTCCCAGGCTCCTGCATTCTATAAGCGTAATTTTATGCCGGGTATGCTTGTGATTTGACGAA GATCTACTCGACGGCGTTCTGGTGGGCAAAATCGGAGGCAAACCCAATTGGCCCCCCTGGAGTGATAAGTCC TGGGTGCCAAGTGCGCAAGTGAAGCCTTGAACTGCGCCTTTCCTTGCACCTTGTTCGCCGCTCTTTCTATTAA TTAAAATG (SEQ ID NO: 51) |
| Cr-RPS9 cp | GCAGAAGGGTGCCAAAGGGAGGCTCTAAGCAGTCCAGGCGGGCACAAACATATAAAGCTGAAGCTAGTGGTA TACCTAAATTAATTTTGGGGCGCTCCACTGAAAAATGGACTGCCTGCATGGGCCCTGTACGGCTTCGCCGAGC GAGCCCGGTGCAAGGGCCGCGACCGTGCATAAGTCTCTCTCTTTCAAGTTGGCAGAGGGAGCGCCAGTTAAT TAAAATG (SEQ ID NO: 52) |
| Cr-RPL10a cp | CTGGGCCTTACTTTCATCATAGGGAAAGCATAAATCATAACAGTGTAGTTTATATTATGCATGATGTCTTCCGC AGAAGAGGCACCGTGATGCCCACCGCCCCCATGCATCAATTGTGAGGGTCAAGAGCGCCCGCGGACCCCTG GACATTCCTTTTCCTTGGGTGATTAATTAAAATG (SEQ ID NO: 53) |
| Cr-HSP70A cp | CGCGCGGCGTCCAGAAGGCGCCATACGGCCCGCTGGCGGCACCCATCCGGTATAAAAGCCCGCGACCCCG AACGGTGACCTCCACTTTCAGCGACAAACGAGCACTTATACATACGCGACTATTCTGCCGCTATACATAACCA CTCAACTCGCTTAAGAGTTAATTAAAATG (SEQ ID NO: 54) |
| Cr-VIP1 cp | CAGCTGCGGGCAGGCCGGCTGCATGGCTTGCTTCTGGAGAGGGCCAATTGTAATTACCGCTTTCCTGCCTTT CCAAGAGCCCCCTACAACCTACGCACTTTAAAATCACATACAGCCTGTGGCCCAACTTCCTTGTTAGTCCTTAA TTAAAATG (SEQ ID NO: 55) |
| Cr-NPC1 cp | CCTGGTAAATATTCTGCGCCGCTTTCGTAACAGGTGCAGGCGCAGGTAGCTATACAAATATGGTCGCGGCTG CAAATGCGGGGGGAGGAGGAGTACTTGCATGGGTCGCCCGCGATCGGCACTCCCGCTCGGTCCCCGACTGA ACACCCGCGCGAGCCCCGTGGTTCCCCCCTTTTCAACATTAGCCAACTCGACCCCAGTCGACTTTTCTCGTCG TTTTAATTAAAATG (SEQ ID NO: 56) |
| Cr-AAA1 cp | TCGCCATTGGGGGCCGCATGGGGCCCTGGAGCACCGAAAGTGCAGAGCTCTATAGAGCGCCACTCGTTCTT CTTGCCTCTTCACTAGCCCGCCCACAATAATTGGGTTGCAGTCAAGTGAGTGCGTAGCTTCACAGCAGGGTCT ATAGGGCCCCGACACTTGCACCAAACCTGCCGATCACAAGCATTAATTAAAATG (SEQ ID NO: 57) |
| Mm-Eef2cp | CCCGGACGAGCACCCGGCGCCGTCACGTGACGCACCCAACCGGCGTCGACCTATAAAAGGCCGGGCGTTGAC GTCAGCGGTCTCTTCCGCCGCAGCCGCCGCCATCGTCGGCGCGCTTCCCTGTTCACCTCTGACTCTGAGAAT CCGTCGCCATTAATTAAAATG (SEQ ID NO: 58) |
| Mm-Col1a1cp | TCCCCCTCTCCGAGAGGCAGGGTTCCTCCCAGCTCTCCATCAAGATGGTATAAAAGGGGCCCAGGCCAGTCG TCGGAGCAGACGGGAGTTTCTCCTCGGGACGGAGCAGGAGGCACGCGGAGTGAGGCCACGCATGAGCCGA AGCTAACCCCCCACCCCAGCCGCAAAGAGTCTACATGTCTAGTTAATTAAAATG (SEQ ID NO: 59) |
| Mm-Rpl4cp | CTCTAATTTGATTTTGATAAGGGGCAGGATGCGGAAGACGAGTGGAAGGATATATAGAGTACAAGTGACAAGT CTTTCCTTTTCCTGTGGGAGCAGCCGGGTAGAGAGGAGCGTGGCCTTCTCCTTTAATTAAAATG (SEQ ID NO: 60) |
| Mm-Fabp9cp | TAGAGAGGCTCCCTGAATTAAACTTTGCAGGTTAGTTTCTGTTGGTGGTATATAAAATGAGTCAACCGCCGGT GCCTGGAATCTCAGATTCCTGGCAGCCCATTGGTTGCTTCAGGAATGCCACGTGACAAAGATGTTCTTTAAAA GAAGGGGCTGGCGGCACAGCGATGCCCACACTTCATGGTTTTTTAATTAAAATG (SEQ ID NO: 61) |
| Mm-Vimcp | GCTCGGCGGCTAGGATGGCAGTGGGAGGGACCCTCTTTCCTAACAGTGTTATAAAAGCAGCGCCCTTGGC GTTGTCCAGTCCTCTGCCACTCTTGCTCCGGGACCCCAGAGACCCCAGCGCTCCTACGATTCACAGCCACCG CGCCCTCATTCCCTTGTTGCAGTTTTTCCAGCCGCAGCAAGCCAGCCCACCTTAATTAAAATG (SEQ ID NO: 62) |
| Mm-Rplp1cp | GTCGGGCATCGATTGGTCGGCGCGGTCCCATAAGAAGCTGCGCGCAGGCGTATATGATCTTTTCCTCAGCTG CCGCCAAGGTGCTCGGTCCTTCCGAGGAAGCTAAGGCCGCGTTGGGGTGAGGCCCTCACTTCATCCGGCGA CTAGCACCGTGCCGGCATTAATTAAAATG (SEQ ID NO: 63) |
| Mm-Atp5bcp | ATTGGCACCAGTTTAGACCAATAGCTGATAAGCTCCGAGTTTTTTACCCTATAGAAGCGTTAGTGGTGATGAC GAACAGCAAAATCACCCAATTACTGTGCCTACGGCGGAGGTTGCCCCGCCCCAGCTGCAGGACCGGCGGAG AGGACCGCTTCGGCGCTCAGTCTCCACCCGTTAATTAAAATG (SEQ ID NO: 64) |
| Mm-Ppt1cp | TGTAAAATGAGAGCAGTGCATAAGATCAATTAAAAGATGGAAAGCCCTTATATAGTAGAGTCTGGTGGGTGTTA AGCAATGAATAAAGTCTCTGTCAGGATGCAGAGCCCGGCAGGGGCGTGGCCACCGGAATTACTTTGGTCC ACAGTCCCCGCGGTCATGTGTTAATTAAAATG (SEQ ID NO: 65) |
| Mm-Lgals1cp | GACTGGTCACCTCTGCTCCAAAATTGACTTTATAATCCATAGACTCCACTTCTGGTGGCCCCCATCCTTGTCCT GACATGCAATTGGCTGAACTCCCGGGGAGGGGCGGGACTCACCGGGTCTGATCCAGTTAAAAAGGTCGGAG CGGGCCTGGGGCCCGTCTCTCGGGTGGAGTCTTCTGACTGCTGGTGGAGCAGGTCTCAGGAATCTCTTCGC TTCATTAATTAAAATG (SEQ ID NO: 66) |

TABLE 1-continued

Selection of core promoters tested in *Saccharomyces cerevisiae* and other organisms. The bolded sequences are the 3'-flanking regions added to the core promoter sequences for screening or cloning purposes. The ATG (start codon) is underlined. Sc—*Saccharomyces cerevisiae* origin; An—*Aspergillus niger* origin; Tr—*Trichoderma reesei* origin; At—*Arabidopsis thaliana* origin; Cr—*Chlamydomonas reinhardtii* origin; Mm—*Mus musculus* origin DNA sequences of the selected UCPs and other CPs used for constructing the expression systems

| | |
|---|---|
| Mm-Fth1cp | GGCCAGCGCTCGCCTGACGCAGGATCCCGCTATAAGTGCGGCCCGCTGTCCCCTCCTGCGCCAGACGTTCT CGCCCAGAGTCGCCGCGGTTTCCTGCTTCAACAGTGCTTGAACGGAACCCGGTGCTCGACCCCTCCGACCC CCGCCGGCCGCTTCGAGCCTGAGCCCTTTGCAACTTCGTCGTTCCGCCGCTCCAGCGTCGCCACCGCGCCT CGCCCCTTAATTAAAATG (SEQ ID NO: 67) |

TABLE 2

DNA sequences of some of the tested inter-species transferable expression systems. The functional DNA parts are indicated: 8 x BM3R1 binding site (black text, bolded); core promoters (underlined); mCherry coding region (black text, bolded, underlined); terminators (italics); BM3R1-sTF (bolded italics). DNA sequences of the tested inter-species transferable expression systems

| | |
|---|---|
| 8BS(BM3R1)-<br>201cp-<br>mCherry +<br>008cp-<br>BM3R1_sTF | GCATTTGCTCGGCTAGTCGGAATGAACATTCATTCCGAGACCTAGGAT<br>GTGACGGAATGAAGGTTCATTCCGGACTCTAGATAAGCACGGAATGAA<br>CTTTCATTCCGCTGAAGCTTGTCAATCGGAATGAAGGTTCATTCCGGC<br>TAGTCGGAATGAACATTCATTCCGAGACCTAGGATGTGACGGAATGAA<br>GGTTCATTCCGGACTCTAGATAAGCACGGAATGAACTTTCATTCCGCT<br>GAAGCTTGTCAATCGGAATGAAGGTTCATTCCGGCTAGTTCTCCCCGG<br>AAACTGTGGC<u>CATATGTTCAAAGACTAGGATGGATAAATGGGGTATATA</u><br><u>AAGCACCCTGACTCCCTTCCTCCAAGTTCTATCTAACCAGCCATCCTAC</u><br><u>ACTCTACATATCCACACCAATCTACTACAATTATTAATTAAA</u><u>ATGGTGAG</u><br><u>CAAGGGCGAGGAGGATAACATGGCCATCATCAAGGAGTTCATGCGCT</u><br><u>TCAAGGTGCACATGGAGGGCTCCGTGAACGGCCACGAGTTCGAGATC</u><br><u>GAGGGCGAGGGCGAGGGCCGCCCCTACGAGGGCACCCAGACCGCC</u><br><u>AAGCTGAAGGTGACCAAGGGTGGCCCCCTGCCCTTCGCCTGGGACAT</u><br><u>CCTGTCCCCTCAGTTCATGTACGGCTCCAAGGCCTACGTGAAGCACC</u><br><u>CCGCCGACATCCCCGACTACTTGAAGCTGTCCTTCCCCGAGGGCTTC</u><br><u>AAGTGGGAGCGCGTGATGAACTTCGAGGACGGCGGCGTGGTGACCG</u><br><u>TGACCCAGGACTCCTCCCTGCAGGACGGCGAGTTCATCTACAAGGTG</u><br><u>AAGCTGCGCGGCACCAACTTCCCCTCCGACGGCCCCGTAATGCAGAA</u><br><u>GAAGACCATGGGCTGGGAGGCCTCCTCCGAGCGGATGTACCCCGAG</u><br><u>GACGGCGCCCTGAAGGGCGAGATCAAGCAGAGGCTGAAGCTGAAGG</u><br><u>ACGGCGGCCACTACGACGCTGAGGTCAAGACCACCTACAAGGCCAA</u><br><u>GAAGCCCGTGCAGCTGCCCGGCGCCTACAACGTCAACATCAAGTTGG</u><br><u>ACATCACCTCCCACAACGAGGACTACACCATCGTGGAACAGTACGAA</u><br><u>CGCGCCGAGGGCCGCCACTCCACCGGCGGCATGGACGAGTTATACA</u><br><u>AG</u>TAATGAGGATCCGAATTTCTTATGATTTATGATTTTTATTATTAAATAA<br>*GTTATAAAAAAAATAAGTGTATACAAATTTTAAAGTGACTCTTAGGTTTTA*<br>*AAACGAAAATTCTTATTCTTGAGTAACTCTTTCCTGTAGGTCAGGTTGCT*<br>*TTCTCAGGTATAGCATGAGGTCGCTCTTATTGACCACACCTCTACCGGC*<br>*CAGCTTTTGTTCCCTTTAGTGAGGGTTAATTGCGCGTCGAGGCTAAC*AA<br>CCCAAAGTAATAAGTCTGTAGTAATTGGTCTCGCCCTGAATTCCAAACT<br>ATAAATCAACCACTTTCCCTCCTCCCCCCCGCCCCCACTTGGTCGATTC<br>TTCGTTTTCTCTCTACCTTCTTTCTATTCGGTTTTCTTCTTCTTTTATTTTC<br>CCTCTCCCATCAATCAAATTCATATTTGAAAAAAATTAACCATTAATTAAC<br><sub>*A*</sub>*ATGGAGTCCACACCCACGAAACAAAAAGCTATTTTTTCTGCCTCGCT*<br>*CCTTCTGTTCGCCGAACGCGGGTTTGACGCCACTACGATGCCGATGA*<br>*TCGCTGAAAATGCTAAGGTCGGCGCAGGAACGATTTACCGATACTTT*<br>*AAGAATAAGGAGAGTCTGGTCAACGAGCTGTTCCAGCAGCACGTTAA*<br>*TGAATTTTTGCAATGTATCGAGAGTGGCTTGGCGAACGAAAGGGACG*<br>*GTTATCGCGATGGGTTCCATCATATCTTCGAGGGAATGGTCACATTCA*<br>*CAAAGAACCATCCGCGCGCCTTGGGATTTATCAAGACACATTCCCAA*<br>*GGTACATTCCTAACCGAAGAGTCACGCCTTGCATACCAAAAACTTGTT*<br>*GAGTTCGTCTGCACCTTCTTTCGAGAGGGACAGAAACAGGGCGTAAT*<br>*TCGAAACTTGCCCGAGAATGCCCTGATCGCCATCCTATTCGGATCGTT*<br>*TATGGAGGTCTATGAGATGATCGAAAACGATTATCTCTCTAACGGA*<br>*TGAGTTGCTTACGGGGTAGAGGAATCGCTCTGGGCTGCTCTCTCCC*<br>*GACAATCGGCTAGCCCTCCCAAGAAGAAGCGCAAGGTCAGCACGGC*<br>*CCCCCCACGGACGTCTCCCTCGGCGACGAGCTCCACCTGGACGGC*<br>*GAGGACGTCGCCATGGCCCACGCCGACGCCCTCGACGACTTCGACC*<br>*TCGACATGCTGGGCGACGGCGACAGCCCCGGCCCCGGCTTTACCCC*<br>*CCACGACTCCGCCCCCTACGGCGCCCTGGACATGGCCGACTTCGAGT*<br>*TTGAGCAGATGTTCACCGACGCCCTGGGCATTGACGAGTACGGCGGC*<br>TGAGGCCGGCC*GCGATACCCATCATCAACACCTGATGTTCTGGGGTC*<br>*CCTCGTGAGGTTTCTCCAGGTGGGCACCACCATGGCTCACTTCTTAC*<br>*GACGAAACGATCAATGTTGCTATGCATGAGCACTCGACTATGAATCG* |

TABLE 2-continued

DNA sequences of some of the tested inter-species transferable expression systems. The functional DNA parts are indicated: 8 × BM3R1 binding site (black text, bolded); core promoters (underlined); mCherry coding region (black text, bolded, underlined); terminators (italics); BM3R1-sTF (bolded italics). DNA sequences of the tested inter-species transferable expression systems

| | |
|---|---|
| | *AGGCACGTTAATTGAGAGGCTGGGAATAAGGGTTCCATCAGAACTTC*<br>*TCTGGGAATGCAAAACAAAAGGGAACAAAAAAACTAGATAGAAGTGA*<br>*ATTCATGACTTCGACAACCAAATCATCTTGTCTCCGTCTGCATACGTG*<br>*AAGCTTGTGACGATTATTCTCGCGATGCCACGACAAAGGTTGTGCGA*<br>*CCGTATCTTGTCCACTGTCGTCCAGTCTGCCTATTCCCCCTCCAGTGC*<br>*TGCCATGTGTCGTACCTTGAGGTAGGTAGTCTACCTAGGCCAGGGAG*<br>*CTGTTAGTGCCCGGCTACTGGGTAATTTGTAGCGCTGGAGCGATTCG*<br>*GTCACAGGCGTCAAGAGTGCTGTAGCAATGTCCGACGCCATTGATCC*<br>*TGATATCAAATACCACCTGGGCAGGTCTGGGTATGTGAGGTCTTGTCG*<br>*GATGTGTCGAGTTCTTCTCCAACGTAGTGTTCATTCGCGCTCAT*GCCC<br>(SEQ ID NO: 68) |
| 8BS(BM3R1)-<br>114cp-<br>mCherry +<br>533cp-<br>BM3R1_sTF | GCATTTGCTCGGCTAGTCGGAATGAACATTCATTCCGAGACCTAGGAT<br>GTGACGGAATGAAGGTTCATTCCGGACTCTAGATAAGCACGGAATGAA<br>CTTTCATTCCGCTGAAGCTTGTCAATCGGAATGAAGGTTCATTCCGGC<br>TAGTCGGAATGAACATTCATTCCGAGACCTAGGATGTGACGGAATGAA<br>GGTTCATTCCGGACTCTAGATAAGCACGGAATGAACTTTCATTCCGCT<br>GAAGCTTGTCAATCGGAATGAAGGTTCATTCCGGCTAGTTCTCCCCGG<br><u>AAACTGTGGCCATATGCCCTGCAGTGCCTGATCACCTTATCAAGTGGC</u><br><u>CAAATATCCCACTATAAAAGGCTTGGGAACCCCTCGTTCTGTCTTACCT</u><br><u>TCTATCATCTTACCAAATCCACTCCTCTTCCTTCATACATCAATCTTACC</u><br><u>AATCAACTACCTCTACAACTCCAATACACTTAATTAAA</u><u>ATGGTGAGCAA</u><br><u>GGGCGAGGAGGATAACATGGCCATCATCAAGGAGTTCATGCGCTTCA</u><br><u>AGGTGCACATGGAGGGCTCCGTGAACGGCCACGAGTTCGAGATCGA</u><br><u>GGGCGAGGGCGAGGGCCGCCCCTACGAGGGCACCCAGACCGCCAA</u><br><u>GCTGAAGGTGACCAAGGGTGGCCCCCTGCCCTTCGCCTGGGACATCC</u><br><u>TGTCCCCTCAGTTCATGTACGGCTCCAAGGCCTACGTGAAGCACCCC</u><br><u>GCCGACATCCCCGACTACTTGAAGCTGTCCTTCCCCGAGGGCTTCAA</u><br><u>GTGGGAGCGCGTGATGAACTTCGAGGACGGCGGCGTGGTGACCGTG</u><br><u>ACCCAGGACTCCTCCCTGCAGGACGGCGAGTTCATCTACAAGGTGAA</u><br><u>GCTGCGCGGCACCAACTTCCCCTCCGACGGCCCCGTAATGCAGAAGA</u><br><u>AGACCATGGGCTGGGAGGCCTCCTCCGAGCGGATGTACCCCGAGGA</u><br><u>CGGCGCCCTGAAGGGCGAGATCAAGCAGAGGCTGAAGCTGAAGGAC</u><br><u>GGCGGCCACTACGACGCTGAGGTCAAGACCACCTACAAGGCCAAGA</u><br><u>AGCCCGTGCAGCTGCCCGGCGCCTACAACGTCAACATCAAGTTGGAC</u><br><u>ATCACCTCCCACAACGAGGACTACACCATCGTGGAACAGTACGAACG</u><br><u>CGCCGAGGGCCGCCACTCCACCGGCGGCATGGACGAGTTATACAAG</u><br>*TAATGAGGATCCGAATTTCTTATGATTTATGATTTTTATTATTAAATAAGT*<br>*TATAAAAAAAATAAGTGTATACAAATTTTAAAGTGACTCTTAGGTTTTAAA*<br>*ACGAAAATTCTTATTCTTGAGTAACTCTTTCCTGTAGGTCAGGTTGCTTT*<br>*CTCAGGTATAGCATGAGGTCGCTCTTATTGACCACACCTCTACCGGCC*<br>*AGCTTTTGTTCCCTTTAGTGAGGGTTAATTGCGCGTCGAGGCTAGC*CG<br>CCCCAAGAGAGCTGAAGATGCTGAGTAGGGTTGTCCAGGCAGCACATA<br>TATAAGATGCTTCGTCCCCTCCCATCGAGTCCTTCTTTTCTCTCTCAT<br>CAATCACTCTACTTCCTACTCTACCTTAAACTCTTCACTACTTCATACGA<br>TTAACAA*ATGGAGTCCACACCCACGAAACAAAAAGCTATTTTTTCTGCC*<br>*TCGCTCCTTCTGTTCGCCGAACGCGGGTTTGACGCCACTACGATGCC*<br>*GATGATCGCTGAAAATGCTAAGGTCGGCGCAGGAACGATTTACCGAT*<br>*ACTTTAAGAATAAGGAGAGTCTGGTCAACGAGCTGTTCCAGCAGCAC*<br>*GTTAATGAATTTTTGCAATGTATCGAGAGTGGCTTGGCGAACGAAAGG*<br>*GACGGTTATCGCGATGGGTTCCATCATATCTTCGAGGGAATGGTCAC*<br>*ATTCACAAAGAACCATCCGCGCCTTGGGATTTATCAAGACACATTC*<br>*CCAAGGTACATTCCTAACCGAAGAGTCACGCCTTGCATACCAAAAAC*<br>*TTGTTGAGTTCGTCTGCACCTTCTTTCGAGAGGGACAGAAACAGGGC*<br>*GTAATTCGAAACTTGCCCGAGAATGCCCTGATCGCCATCCTATTCGGA*<br>*TCGTTTATGGAGGTCTATGAGATGATCGAAAACGATTATCTCTCTCTA*<br>*ACGGATGAGTTGCTTACGGGGGTAGAGGAATCGCTCTGGGCTGCTCT*<br>*CTCCCGACAATCGGCTAGCCCTCCCAAGAAGAAGCGCAAGGTCAGC*<br>*ACGGCCCCCCCACGGACGTCTCCCTCGGCGACGAGCTCCACCTGG*<br>*ACGGCGAGGACGTCGCCATGGCCCACGCCGACGCCCTCGACGACTT*<br>*CGACCTCGACATGCTGGGCGACGGCGACAGCCCCGGCCCCGGCTTT*<br>*ACCCCCCACGACTCCGCCCCCTACGGCGCCCTGGACATGGCCGACTT*<br>*CGAGTTTGAGCAGATGTTCACCGACGCCCTGGGCATTGACGAGTACG*<br>*GCGGCT*TGAGGCCGGCC*GCGATACCCATCATCAACACCTGATGTTCTG*<br>*GGGTCCCTCGTGAGGTTTCTCCAGGTGGGCACCACCATGCGCTCACT*<br>*TCTACGACGAAACGATCAATGTTGCTATGCATGAGCACTCGACTATGA*<br>*ATCGAGGCACGTTAATTGAGAGGCTGGGAATAAGGGTTCCATCAGAA*<br>*CTTCTCTGGGAATGCAAAACAAAAGGGAACAAAAAAACTAGATAGAA*<br>*GTGAATTCATGACTTCGACAACCAAATCATCTTGTCTCCGTCTGCATA*<br>*CGTGAAGCTTGTGACGATTATTCTCGCGATGCCACGACAAAGGTTGT*<br>*GCGACCGTATCTTGTCCACTGTCGTCCAGTCTGCCTATTCCCCCTCCA*<br>*GTGCTGCCATGTGTCGTACCTTGAGGTAGGTAGTCTACCTAGGCCAG* |

TABLE 2-continued

DNA sequences of some of the tested inter-species transferable expression systems. The functional DNA parts are indicated: 8 × BM3R1 binding site (black text, bolded); core promoters (underlined); mCherry coding region (black text, bolded, underlined); terminators (italics); BM3R1-sTF (bolded italics). DNA sequences of the tested inter-species transferable expression systems

***GGAGCTGTTAGTGCCCGGCTACTGGGTAATTTGTAGCGCTGGAGCGA
TTCGGTCACAGGCGTCAAGAGTGCTGTAGCAATGTCCGACGCCATTG
ATCCTGATATCAAATACCACCTGGGCAGGTCTGGGTATGTGAGGTCTT
GTCGGATGTGTCGAGTTCTTCTCCAACGTAGTGTTCATTCGCGCTCAT
GCCC*** (SEQ ID NO: 69)

TABLE 3

DNA sequence of the expression system tested in *Kazachstania exigua* and *Saccharomyces cerevisiae*. The functional DNA parts are indicated: 8 × TetR binding site (black text, bolded); core promoters (underlined); Venus coding region (black text, bolded, underlined); terminators (italics highlight); TetR-sTF (bolded italics).
DNA sequence of the expression system tested in *Kazachstania exigua* and *Saccharomyces cerevisiae*

| | |
|---|---|
| 8BS(TetR)-<br>ENO1cp-<br>Venus +<br>TDH3cp-<br>TetR_sTF | GCTAGCTCTCTATCACTGATAGGGAGTATTGACAAGCTTTCTCTATCAC<br>TGATAGGAGTGGCTTATCTAGATCTCTATCACTGATAGGGAGTTCACA<br>TCCTAGGTCTCTATCACTGATAGGGAGTACTAGCTCTCTATCACTGATA<br>GGGAGTATTGACAAGCTTTCTCTATCACTGATAGGGAGTGGCTTATCTA<br>GATCTCTATCACTGATAGGGAGTTCACATCCTAGGTCTCTATCACTGAT<br>AGGGAGTACTAGTTCTCCCCGGAAACTGTGGCCTTTTCTGGCACACAT<br>GATCTCCACGATTTCAACATATAAATAGCTTTTGATAATGGCAATATTAA<br>TCAAATTTATTTTACTTCTTTCTTGTAACATCTCTCTTGTAATCCCTTATT<br>CCTTCTAGCTATTTTTCATAAAAAACCAAGCAACTGCTTATCAACACACA<br>AACACTTAATTAAA<u>ATGTGGTCTCATCCACAATTTGAAAAATCTAAAGG<br>TGAAGAATTATTCACTGGTGTTGTCCCAATTTTGGTTGAATTAGATGGT<br>GATGTTAATGGTCACAAATTTTCTGTCTCCGGTGAAGGTGAAGGTGAT<br>GCTACTTACGGTAAATTGACCTTAAAATTGATTTGTACTACTGGTAAAT<br>TGCCAGTTCCATGGCCAACCTTAGTCACTACTTTAGGTTATGGTTTGC<br>AATGTTTTGCTAGATACCCAGATCATATGAAACAACATGACTTTTTCAA<br>GTCTGCCATGCCAGAAGGTTATGTTCAAGAAAGAACTATTTTTTTCAA<br>AGATGACGGTAACTACAAGACCAGAGCTGAAGTCAAGTTTGAAGGTG<br>ATACCTTAGTTAATAGAATCGAATTAAAAGGTATTGATTTTAAAGAAG<br>ATGGTAACATTTTAGGTCACAAATTGGAATACAACTATAACTCTCACA<br>ATGTTTACATCACTGCTGACAAACAAAAGAATGGTATCAAAGCTAACT<br>TCAAAATTAGACACAACATTGAAGATGGTGGTGTTCAATTAGCTGACC<br>ATTATCAACAAAATACTCCAATTGGTGATGGTCCAGTCTTGTTACCAG<br>ACAACCATTACTTATCCTATCAATCTGCCTTATCCAAAGATCCAAACG<br>AAAAGAGAGACCACATGGTCTTGTTAGAATTTGTTACTGCTGCTGGTA<br>TTACCCATGGTATGGATGAATTGTACAAAGGATCC</u>TAAGTCGACGCTA<br>*ATTAACATAAAACTCATGATTCAACGTTTGTGTATTTTTTTACTTTTGAAG<br>GTTATAGATGTTTAGGTAAATAATTGGCATAGATATAGTTTTAGTATAAT<br>AAATTTCTGATTTGGTTTAAAATATCAACTATTTTTTTTCACATATGTTCTT<br>GTAATTACTTTTCTGTCCTGTCTTCCAGGTTAAAGATTAGCTTCTAATAT<br>TTTAGGTGGTTTATTATTTAATTTTATGCTGATTAATTTATTTACTTTCGTA<br>TTCGGTTTTGTACCTTTAGCTATGATCTTAGCTAATTGAAGGGGCCTCG<br>AGGCTAGC*<u>AGCTGAAAAAAAAGGTTGAAACCAGTTCCCTGAAATTATTC<br>CCCTACTTGACTAATAAGTATATAAAGACGGTAGGTATTGATTGTAATTC<br>TGTAAATCTATTTCTTAAACTTCTTAAATTCTACTTTTATAGTTAGTCTTTT<br>TTTTAGTTTTAAAACACCAAGAACTTAGTTTCGAATAAACACCATAATTA<br>ATTAAATCTAGACA</u>*ATGAGTAGATTAGACAAATCAAAAGTGATAAATTC<br>TGCATTAGAATTGTTGAATGAAGTAGGCATTGAAGGTTTGACTACCCG<br>TAAGTTAGCTCAGAAACTAGGTGTTGAACAACCTACATTATACTGGCA<br>CGTTAAAAATAAAAGGGCATTGTTGGATGCGCTTGCCATTGAGATGTT<br>GGATAGGCATCATACCCACTTTTGCCCATTAGAAGGAGAGTCTTGGC<br>AGGACTTTTTGAGGAATAATGCCAAGTCATTTAGATGTGCATTGTTGT<br>CTCATAGAGATGGGGCCAAGGTTCATCTAGGTACCCGTCCTACGGAA<br>AAACAATATGAGACGTTGGAAAATCAGTTAGCGTTCTTATGCCAACAA<br>GGCTTTAGCTTGGAAAATGCTTTATATGCTCTATCAGCTGTCGGTCATT<br>TTACATTGGGATGCGTTTTAGAAGACCAGGAGCACCAGGTGGCAAAG<br>GAAGAAAGAGAAACACCAACAACTGATTCAATGCCACCCCTACTGAG<br>ACAAGCTATCGAATTATTTGATCATCAAGGTGCGGAACCTGCCTTCTT<br>GTTTGGCCTAGAATGATCATTTGTGGTTTAGAAAAGCAGTTAAAATG<br>TGAGAGTGGCTCAGAATTCCCTCCCAAGAAGAAGCGCAAGGTCAGCA<br>CGGCCCCCCCACGGACGTGTCCCTCGGCGACGAGCTCCACCTGGA<br>CGGCGAGGACGTCGCCATGCCCACGCCGACGCCCTCGACGACTTC<br>GACCTCGACATGCTGGGCGACGGCGACAGCCCCGGCCCCGGCTTTA* |

TABLE 3-continued

DNA sequence of the expression system tested in *Kazachstania exigua* and *Saccharomyces cerevisiae*. The functional DNA parts are indicated: 8 × TetR binding site (black text, bolded); core promoters (underlined); Venus coding region (black text, bolded, underlined); terminators (italics highlight); TetR-sTF (bolded italics).
DNA sequence of the expression system tested in *Kazachstania exigua* and *Saccharomyces cerevisiae*

*CCCCCCACGACTCCGCCCCCTACGGCGCCCTGGACATGGCCGACTTC*
*GAGTTTGAGCAGATGTTCACCGACGCCCTGGGCATTGACGAGTACGG*
*CGGCTGA* (SEQ ID NO: 70)

TABLE 4

DNA sequences of the expression systems tested in *Nicotiana benthamiana*. The functional DNA parts are indicated: 8 × sTF binding site (black text, bolded); core promoters (underlined); mCherry coding region (black text, bolded, underlined); terminators (italics); sTFs (bolded italics).
DNA sequence of the expression system tested in *Nicotiana benthamiana*

8BS(BM3R1)-
At-ATTI7cp-
mCherry +
At-RPL41Dcp -
BM3R1_sTF

CATTTGCTCGGCTAGTCGGAATGAACATTCATTCCGAGACCTAGGATG
TGACCGGAATGAAGGTTCATTCCGGACTCTAGATAAGCA**CGGAATGAAC
TTTCATTCCGCTGAAGCTTGTCAATCGGAATGAAGGTTCATTCCG**GCTA
GTCGGAATGAACATTCATTCCGAGACCTAGGATGTGAC**CGGAATGAAG
GTTCATTCCGGACTCTAGATAAGCACGGAATGAACTTTCATTCCG**CTG
AAGCTTGTCAATCGGAATGAAGGTTCATTCCGGCTAGTTCTCCCCGGA
AACTGGAATTTGTGGTTCTCGTGAAGTCGTGATAATAGTTTGTCCAAGC
GATAAATATAAAATAGTATTGCACCTCAACAAGTGTTAAGCATGCAAATC
CATTTACGCATACATATTAACTCCGAGTGAAATATAAATATTAGAGAGTA
GAGACAGAGAAAAGACAGAGACAAAGTTAATTAAAATGGTAAGCAAG
GGAGAAGAGGATAACATGGCAATCATAAAGGAATTTATGCGTTTCAA
GGTCCACATGGAAGGTTCTGTCAATGGGCACGAGTTCGAGATTGAAG
GCGAGGGGGAGGGTAGACCGTATGAAGGGACCCAGACTGCCAAATT
GAAGGTAACAAAAGGCGGGCCGCTTCCATTCGCTTGGGATATCCTCA
GTCCGCAGTTCATGTATGGCTCCAAGGCCTATGTGAAGCATCCTGCA
GATATACCCGACTATTTAAAGCTCAGTTTCCCCGAGGGCTTCAAATGG
GAAAGAGTTATGAATTTTGAGGACGGAGGTGTTGTAACCGTCACGCA
GGATAGCAGCTTACAGGACGGCGAATTTATTTACAAGGTAAAGTTGC
GTGGTACGAATTTTCCTTCAGATGGTCCGGTCATGCAGAAGAAGACTA
TGGGTTGGGAAGCAAGCTCTGAGAGGATGTATCCCGAAGATGGGGCT
CTTAAAGGCGAGATAAAGCAGAGGCTGAAACTGAAGGACGGCGGGC
ACTACGATGCCGAAGTCAAAACCACCTATAAGGCTAAAAAGCCCGTA
CAGCTTCCCGGTGCTTACAACGTGAACATCAAATTAGACATTACCTCC
CACAATGAAGACTATACCATCGTGGAGCAATACGAGAGGGCCGAGG
GAAGGCACTCTACAGGAGGAATGGATGAACTCTACAAAGGATCCTAA
*TAGCTATATATCTTTCTTACATCATTATTGTAATCTGTTCTCCTTCTGTGT*
*ATTCGTTTCAATGTTGCAGCAATGAACTTTTGGATAAAAGTCAAATTTGT*
*TGTTTCCTTAATTCGAAAGACGATTGAGACTTGAAATCATAACACTAAGC*
*TTCATTGAATCAAGATTCAATAGTATTCATCAATTCATAATATAATAGTGT*
*ACTAAACTCGAGCTTGCATATTCTGAGTTAATTGAAATACCTCACTGTAA*
*TACCTAGAACGAACTTACCTTACGAGCAAATCAAGCATGTATTTACTCTC*
*GGATGTATAATTCACCTTATCAACCTTCACAACAGTCATCTTCACTCTTT*
*GTTCATCCCCATACGATTCCTCTTTGATCTTCAGCTTCATTTAAATGCGA*
TCCCCTCTGGCAAATTCTTATCCATTTGGGTTTTATTGGGCTTTTGAAAT
AATAAAGCCCATTAAGTTAGTTACTAGGGTTTTGTTGTTGTTTAAAGGAG
GAATAAGAGCGTAAGCTACAAAATCTTTCTATTCATCTCCGCCGCTCCT
CATCCTGTAAAGCTAAACAAATAATCAGAGGAACGAAGGAGACAGCTTC
TGCTTAATTAAAATGGAGAGTACACCAACCAAACAGAAAGCTATTTTT
AGCGCAAGCCTGTTATTATTTGCTGAGCGTGGCTTTGACGCTACGACG
ATGCCCATGATAGCCGAAAATGCTAAAGTTGGGGCTGGAACCATATA
CCGATACTTCAAAAACAAAGAAAGTCTGGTGAATGAACTGTTTCAACA
ACACGTAAACGAGTTCTTGCAGTGCATCGAGTCTGGACTCGCTAACG
AGCGTGACGGCTATAGAGATGGATTTCATCATATATTTGAGGGCATGG
TCACCTTCACAAAAAACCACCCAAGGGCTCTGGGTTTCATAAAAACG
CACAGTCAAGGCACATTCCTTACGGAGGAGAGCAGATTAGCATATCA
GAAATTAGTGGAGTTCGTATGTACTTTCTTTAGAGAAGGACAGAAGCA
AGGAGTTATTCGAAACCTGCCGGAAAACGCCTTAATTGCCATCCTGTT
TGGGTCTTTCATGGAAGTTTACGAAATGATAGAGAATGATTACCTCTC
CCTTACCGACGAATTGTTGACTGGCGTCGAAGAATCATTGTGGGCAG
CATTGTCTAGGCAATCAGAATTCCCACCTAAGAAGAAAAGGAAAGTA
TCCGCCTCCGGTTCTGGGCGTGCCGACGCTCTGGACGATTTCGACCT
CGATATGTTGGGGTCAGACGCATTGGACGACTTTGATTTGGACATGTT
AGGTAGTGATGCTTTAGACGATTTCGACTTGGACATGTTAGGCTCCGA
TGCATTGGACGATTTTGACTTAGATATGTTGATTAATAGTAGGT*AA*TGA

TABLE 4-continued

DNA sequences of the expression systems tested in *Nicotiana benthamiana*. The functional DNA parts are indicated: 8 × sTF binding site (black text, bolded); core promoters (underlined); mCherry coding region (black text, bolded, underlined); terminators (italics); sTFs (bolded italics).
DNA sequence of the expression system tested in *Nicotiana benthamiana*

| | |
|---|---|
| | *GTCGACTCTTTAATCAAAATGTAATATGAATAAAAGTTGATGTGGGCT*<br>*CATCTATTGAGCTCATGTCTCTCTTATTACTACTCTAGTATGGTGTG*<br>*ATGTAATGGGTTATGACCCTTCTTTCCCTTCCCTATAAAACTAAAGAAA*<br>*CTTGCAAGATAATTGAAAAGATGGTTTCTTTTTATTATCAATCGCATCA*<br>*AAATGGGATTTTGTATCAAATGCATACATTATCTCTTGCTTTTATACCC*<br>*TAAACCCATACCGGGTGATGAACAATCTTCTGTTGCTCATTCCTTTTGA*<br>*TGATCCATCAAATTACGTATTAGAAAAAGAAAAAAAAGTATCAGACGT*<br>*TGAAACCTTCTGCTCGGAGACAAATTTTATGAGCCTCGATCC*ATTTAAA<br>TCAAGCCCGGG (SEQ ID NO: 71) |
| 8BS(TetR)-<br>At-<br>ATTI7cp-<br>mCherry +<br>At-<br>RPL41Dcp -<br>TetR_sTF | CATTTGCTCGGCTAGCTCTCTATCACTGATAGGGAGTATTGACAAGCTT<br>TCTCTATCACTGATAGGAGTGGCTTATCTAGATCTCTATCACTGATAGG<br>GAGTTCACATCCTAGGTCTCTATCACTGATAGGGAGTACTAGCTCTCT<br>ATCACTGATAGGGAGTATTGACAAGCTTTCTCTATCACTGATAGGAGT<br>GGCTTATCTAGATCTCTATCACTGATAGGGAGTTCACATCCTAGGTCTC<br>TATCACTGATAGGGAGTACTAGTTCTCCCCGGAAACTGGAATTTGTGG<br>TTCTCGTGAAGTCGTGATAATAGTTTGTCCAAGCGATAAATATAAAATAG<br>TATTGCACCTCAACAAGTGTTAAGCATGCAAATCCATTTACGCATACATA<br>TTAACTCCGAGTGAAATATAAATATTAGAGAGTAGAGACAGAGAAAAAG<br>ACAGAGACAAAGTTAATTAAAA<u>ATGGTAAGCAAGGGAGAAGAGGATAAC</u><br><u>ATGGCAATCATAAAGGAATTTATGCGTTTCAAGGTCCACATGGAAGGT</u><br><u>TCTGTCAATGGGCACGAGTTCGAGATTGAAGGCGAGGGGGAGGGTA</u><br><u>GACCGTATGAAGGGACCCAGACTGCCAAATTGAAGGTAACAAAAGG</u><br><u>CGGGCCGCTTCCATTCGCTTGGGATATCCTCAGTCCGCAGTTCATGTA</u><br><u>TGGCTCCAAGGCCTATGTGAAGCATCCTGCAGATATACCCGACTATTT</u><br><u>AAAGCTCAGTTTCCCCGAGGGCTTCAAATGGGAAAGAGTTATGAATTT</u><br><u>TGAGGACGGAGGTGTTGTAACCGTCACGCAGGATAGCAGCTTACAGG</u><br><u>ACGGCGAATTTATTTACAAGGTAAAGTTGCGTGGTACGAATTTTCCTT</u><br><u>CAGATGGTCCGGTCATGCAGAAGAAGACTATGGGTTGGGAAGCAAG</u><br><u>CTCTGAGAGGATGTATCCCGAAGATGGGGCTCTTAAAGGCAGATAA</u><br><u>AGCAGAGGCTGAAACTGAAGGACGGCGGGCACTACGATGCCGAAGT</u><br><u>CAAAACCACCTATAAGGCTAAAAAGCCCGTACAGCTTCCCGGTGCTT</u><br><u>ACAACGTGAACATCAAATTAGACATTACCTCCCACAATGAAGACTATA</u><br><u>CCATCGTGGAGCAATACGAGAGGGCCGAGGGAAGGCACTCTACAGG</u><br><u>AGGAATGGATGAACTCTACAAAGGATCC</u>TAATAGCTATATATCTTTCTT<br>*ACATCATTATTGTAATCGTTCTCCTTCTGTGTATTCGTTTCAATGTTGC*<br>*AGCAATGAACTTTTGGATAAAAGTCAAATTTGTTGTTTCCTTAATTCGAA*<br>*AGACGATTGAGACTTGAAATCATAACACTAAGCTTCATTGAATCAAGATT*<br>*CAATAGTATTCATCAATTCATAATATAATAGTGTACTAAACTCGAGCTTG*<br>*CATATTCTGAGTTAATTGAAATACCTCACTGTAATACCTAGAACGAACTT*<br>*ACCTTACGAGCAAATCAAGCATGTATTTACTCTCGGATGTATAATTCACC*<br>*TTATCAACCTTCACAACAGTCATCTTCACTCTTTGTTCATCCCCATACGA*<br>*TTCCTCTTTGATCTTCAGCTTCATTTAAATGCG*ATCCCCTCTGGCAAATT<br>CTTATCCATTTGGGTTTTATTGGGCTTTTGAAATAATAAAGCCCATTAAG<br>TTAGTTACTAGGGTTTTGTTGTTGTTTAAAGGAGGAATAAGAGCGTAAG<br>CTACAAAATCTTTCTATTCATCTCCGCCGCTCCTCATCCTGTAAAGCTAA<br>ACAAATAATCAGAGGAACGAAGGAGACAGCTTCTGCTTAATTAAA*ATGT*<br>*CAAGATTAGACAAAAGCAAAGTAATCAATAGTGCATTAGAACTTTTAA*<br>*ACGAGGTCGGAATAGAGGGATTAACTACACGTAAACTCGCCCAGAAG*<br>*CTCGGAGTTGAACAACCTACGCTGTATTGGCATGTTAAAAATAAACGA*<br>*GCATTATTGGATGCTCTGGCTATTGAGATGCTCGATAGGCACCATACC*<br>*CACTTTTGCCCTCTGGAGGGGGAATCTTGGCAAGACTTCTTGCGTAAC*<br>*AACGCCAAGTCATTCAGATGTGCCTTGCTGAGTCACCGTGACGGCGC*<br>*TAAAGTCCATCTCGGAACCCGACCGACCGAGAAGCAATACGAGACCT*<br>*TAGAAAACCAATTAGCCTTTCTTTGCCAGCAAGGGTTTTCATTAGAGA*<br>*ATGCTCTCTACGCCCTTTCCGCTGTTGGGCATTTCACCCTGGGTTGCG*<br>*TCTTGGAGGATCAGGAACATCAAGTAGCAAAGGAGGAACGAGAGAC*<br>*ACCTACTACGGATTCTATGCCGCCCCTCCTCAGGCAGGCAATTGAACT*<br>*GTTCGATCATCAGGGAGCTGAACCTGCTTTTCTGTTTGGCCTGGAATT*<br>*GATAATATGCGGACTGGAGAAACAGTTAAAGTGCGAGAGCGGTAGC*<br>*GAATTCCCACCTAAAAAAAAGAGAAAAGTTTCCACTGCCCCCCCAAC*<br>*GGACGTCTCTCTGGGCGACGAGCTGCACCTCGATGGTGAGGACGTG*<br>*GCTATGGCTCATGCTGATGCCTTAGACGACTTCGACTTAGATATGCTG*<br>*GGAGATGGCGACTCACCGGGACCAGGGTTTACACCTCATGATTCTGC*<br>*TCCTTACGGAGCTTTAGATATGGCCGATTTTGATTTGAGCAAATGTT*<br>*CACTGACGCCCTTGGAATAGACGAATACGGGGC*TAA*TGAGTCGACT*<br>*CTTTAATCAAAATGTAATATGAATAAAAGTTGATGTGGGCTCATCTATT*<br>*GAGCTCATGTCTCTCTTATTACTACTCTCAGTATGGTGTGATGTAATG*<br>*GGTTATGACCCTTCTTTCCCTTCCCTATAAAACTAAAGAAACTTGCAA*<br>*GATAATTGAAAAGATGGTTTCTTTTTATTATCAATCGCATCAAAATGGG*<br>*ATTTTGTATCAAATGCATACATTATCTCTTGCTTTTATACCCTAAACCC*<br>*ATACCGGGTGATGAACAATCTTCTGTTGCTCATTCCTTTTGATGATCCA* |

TABLE 4-continued

DNA sequences of the expression systems tested in *Nicotiana benthamiana*. The functional DNA parts are indicated: 8 × sTF binding site (black text, bolded); core promoters (underlined); mCherry coding region (black text, bolded, underlined); terminators (italics); sTFs (bolded italics).
DNA sequence of the expression system tested in *Nicotiana benthamiana*

| |
|---|
| *TCAAATTTACGTATTAGAAAAAGAAAAAAAAGTATCAGACGTTGAAACC TTCTGCTCGGACAAATTTTATGAGCCTCGATCC*ATTTAAATCAAGCC CGGG (SEQ ID NO: 72) |

TABLE 5

DNA sequences of the expression systems tested in *Chlamydomonas reinhardtii*. The functional DNA parts are indicated: 8 × sTF binding site (black text, bolded); core promoters (underlined); mCherry coding region (black text, bolded, underlined); terminators (italics); sTFs (bolded italics).
DNA sequence of the expression system tested in *Chlamydomonas reinhardtii*

| | |
|---|---|
| 8BS(BM3R1)-<br>Cr-<br>eIF-5Acp-<br>mCherry +<br>Cr-<br>RPS3Acp -<br>BM3R1_sTF | GCATTTGCTCGGCTAGTCGGAATGAACATTCATTCCGAGACCTAGGAT<br>GTGACGGAATGAAGGTTCATTCCGGACTCTAGATAAGCACGGAATGAA<br>CTTTCATTCCGCTGAAGCTTGTCAATCGGAATGAAGGTTCATTCCGGC<br>TAGTCGGAATGAACATTCATTCCGAGACCTAGGATGTGACGGAATGAA<br>GGTTCATTCCGGACTCTAGATAAGCACGGAATGAACTTTCATTCCGCT<br>GAAGCTTGTCAATCGGAATGAAGGTTCATTCCGGCTAGTTCTCCCCGG<br>AAACTGCGACGAAGGGATGTCTCCGCAAGGCAAGTATATAACGGCTAG<br>CAACGTATGCCTTAGCATAGTAGAGCAATTAGTTGTCTATGTGCCTCGG<br>TGCAAGCGCACACGCCGGGAATAATGCGGCATGGGGGCTTCTGTTGG<br>CCCCATGCGAGCCCCCAGGAAGAAAAGTCGCGCGGCGCCCGTATTCT<br>GCCCTCTTGCTGTGCCAACCTCCTAGTCGCTTCTTCGCACTTTTTAATT<br>AAAATGGTCTCCAAGGGTGAGGAGGACAACATGGCTATCATCAAGGA<br>GTTCATGCGCTTCAAGGTCCATATGGAGGGAGCGTGAACGGCCACG<br>AGTTTGAGATCGAGGGGGAGGGCGAGGGCCGCCCCTACGAGGGCAC<br>CCAGACGGCGAAGCTCAAGGTGACCAAGGGTGGCCCCCTGCCCTTT<br>GCGTGGGACATCCTGTCCCCCCAGTTTATGTACGGGAGCAAGGCTTA<br>CGTCAAGCACCCTGCGGACATCCCTGACTACCTGAAGCTCTCCTTCC<br>CCGAGGGTTTTAAGTGGGAGCGGGTCATGAACTTTGAGGACGGTGGT<br>GTGGTCACCGTGACCCAGGACAGCAGCCTCCAGGATGGTGAGTTTAT<br>TTACAAGGTGAAGCTCCGGGGCACGAACTTCCCCAGCGATGGGCCG<br>GTGATGCAGAAGAAGACGATGGGCTGGGAGGCCTCGTCGGAGCGCA<br>TGTACCCTGAGGACGGCGCCCTGAAGGGTGAGATCAAGCAGCGCCT<br>GAAGCTGAAGGATGGGGGGCATTACGACGCTGAGGTCAAGACGACG<br>TACAAGGCCAAGAAGCCGGTGCAGCTGCCCGGTGCCTACAACGTGA<br>ACATCAAGCTGGACATCACCAGCCACAACGAGGATTACACCATTGTC<br>GAGCAGTACGAGCGGGCTGAGGGCCGCCACTCCACCGGGGGTATGG<br>ACGAGCTGTACAAGGATATC</u>TAAATGGAGGCGCTCGTTGATCTGAGCC<br>*TTGCCCCCTGACGAACGGCGGTGGATGGAAGATACTGCTCTCAAGTGC<br>TGAAGCGGTAGCTTAGCTCCCCGTTTCGTGCTGATCAGTCTTTTTCAAC<br>ACGTAAAAAGCGGAGGAGTTTTGCAATTTTGTTGGTTGTAACGATCCTC<br>CGTTGATTTTGGCCTCTTTCTCCATGGGCGGGCTGGGCGTATTTGAAG<br>CGCTTTTGGAAAAGTTGCTGCGGGGTTCATCAGCTGAAGGGGACTCGG<br>TTCGCAGATCAGTTACACACTAAAGAACGGCGGGTAGCAACACCAGCA<br>AACGTGACGAAACGGAACCGTGCAGCATTTAAATGGC*CCGAACTTGCT<br>CTCGGTGTCATATTGCACCATCCCATCTTGTATAACCGATATAACATAG<br>CTTCGAGTGTGCCGATAAATTATTGTGAGGGCGTCGGGGGGCGAGCT<br>GAGGGAAATGGAGGGGGCACTCATCTCGGCCGCCCCTCCCATCGCGA<br>CCTCGGCGCTCAAGCGGGGGICCCGCACTCGCTTCGGTCTCTTTTGGT<br>CAGCAGCCGTTTGTTGACTACCGTTAATTAAA**ATGGAGAGCACCCCTA<br>*CCAAGCAGAAGGCGATCTTTTCGGCTTCGCTGCTGCTGTTTGCCGAG<br>CGCGGGTTTGATGCTACCACCATGCCCATGATCGCTGAGAACGCTAA<br>GGTCGGGGCGGGCACGATTTACCGGTACTTCAAGAACAAGGAGTCG<br>CTCGTCAACGAGCTGTTTCAGCAGCATGTGAACGAGTTCCTGCAGTG<br>CATTGAGTCCGGTCTCGCCAACGAGCGGGATGGCTACCGCGATGGTT<br>TCCATCACATCTTCGAGGGCATGGTCACGTTTACGAAGAACCATCCTC<br>GCGCTCTCGGTTTTATCAAGACCCATTCCCAGGGGACCTTTCTCACGG<br>AGGAGTCGCGGCTGGCTTACCAGAAGCTGGTCGAGTTTGTCTGCACC<br>TTTTTCCGGGAGGGTCAGAAGCAGGGTGTGATTCGGAACCTGCCGGA<br>GAACGCTCTCATTGCTATCCTCTTTGGCTCGTTTATGGAGGTCTACGA<br>GATGATTGAGAACGATTACCTGTCCCTGACGGACGAGCTGCTCACGG<br>GCGTCGAGGAGAGCCTCTGGGCTGCTCTGTCGCGGCAGTCGGAGCT<br>CCCCCCTAAGAAGAAGCGCAAGGTGTCGGCCTCCGGGAGCGGCCGG<br>GCTGATGCTCTGGATGACTTCGACCTGGACATGCTGGGTAGCGACGC<br>TCTCGACGATTTTGACCTGGACATGCTCGGCTCGGATGCCCTGGACG<br>ATTTCGATCTGGATATGCTGGGTAGCGACGCGCTCGACGACTTTGATC* |

TABLE 5-continued

DNA sequences of the expression systems tested in *Chlamydomonas reinhardtii*. The functional DNA parts are indicated: 8 x sTF binding site (black text, bolded); core promoters (underlined); mCherry coding region (black text, bolded, underlined); terminators (italics); sTFs (bolded italics). DNA sequence of the expression system tested in *Chlamydomonas reinhardtii*

| | |
|---|---|
| | *TGGACATGCTCATTAACAGCCGC*TAAACGCGT*GGCCCCACCGTTGCG*<br>*TGTGCGCCCGCGGTGCGCTGCGCGGTCGGCAGCTTGGGTGTGGCAT*<br>*CCGGTGCGGCTTGTCCCGCCGGCATGTAGCTCTTATGTAACGGGCTG*<br>*TCTGTACTCACTTGTGTCCAACCGCCTCTCTGGATGTCTGGTTCATGA*<br>*CCAACAGCTAAGCAAAGAAGCAGCTGGGACACCAGGGGACGCTGAC*<br>*AATGGAGTGGGCAGCCGACGCAGCAGAGGGGGACTGCGAGTTATA*<br>*CGGTATTAGGCTGGGCTGGCAGGTCCGGTAGACGGTAATGCGACACA*<br>*CAAGCCGTGGGAGAAGGTTGCGTCAGGAAGTCCAAGCAGGTTCTGT*A<br>TTTAAATGCGGCCGC (SEQ ID NO: 73) |
| 8BS(TetR)-<br>Cr-<br>eIF-5A-<br>cp-<br>mCherry +<br>Cr-<br>RPS3Acp -<br>TetR_sTF | TTGCTCGGCTAGCTCTCTATCACTGATAGGGAGTATTGACAAGCTTTCT<br>CTATCACTGATAGGAGTGGCTTATCTAGATCTCTATCACTGATAGGGA<br>GTTCACATCCTAGGTCTCTATCACTGATAGGGAGTACTAGCTCTCTATC<br>ACTGATAGGGAGTATTGACAAGCTTTCTCTATCACTGATAGGAGTGGC<br>TTATCTAGATCTCTATCACTGATAGGGAGTTCACATCCTAGGTCTCTAT<br>CACTGATAGGGAGTACTAGTTCTCCCCGGAAACTGCGACGAAGGGAT<br>GTCTCCGCAAGGCAAGTATATAACGGCTAGCAACGTATGCCTTAGCATA<br>GTAGAGCAATTAGTTGTCTATGTGCCTCGGTCAAGCGCACACGCCGG<br>GAATAATGCGGCATGGGGGCTTCTGTTGGCCCCATGCGAGCCCCCAG<br>GAAGAAAAGTCGCGCGGCGCCCGTATTCTGCCCTCTTGCTGTGCCAAC<br>CTCCTAGTCGCTTCTTCGCACTTTTTAATTAAAATGGTCTCCAAGGGTG<br>AGGAGGACAACATGGCTATCATCAAGGAGTTCATGCGCTTCAAGGTC<br>CATATGGAGGGGAGCGTGAACGGCCACGAGTTTGAGATCGAGGGGG<br>AGGGCGAGGGCCGCCCCTACGAGGGCACCCAGACGGCGAAGCTCAA<br>GGTGACCAAGGGTGGCCCCCTGCCCTTTGCGTGGGACATCCTGTCCC<br>CCCAGTTTATGTACGGGAGCAAGGCTTACGTCAAGCACCCTGCGGAC<br>ATCCCTGACTACCTGAAGCTCTCCTTCCCCGAGGGTTTTAAGTGGGAG<br>CGGGTCATGAACTTTGAGGACGGTGGTGTGGTCACCGTGACCCAGGA<br>CAGCAGCCTCCAGGATGGTGAGTTTATTTACAAGGTGAAGCTCCGGG<br>GCACGAACTTCCCCAGCGATGGGCCGGTGATGCAGAAGAAGACGAT<br>GGGCTGGGAGGCCTCGTCGGAGCGCATGTACCCTGAGGACGGCGCC<br>CTGAAGGGTGAGATCAAGCAGCGCCTGAAGCTGAAGGATGGGGGGC<br>ATTACGACGCTGAGGTCAAGACGACGTACAAGGCCAAGAAGCCGGT<br>GCAGCTGCCCGGTGCCTACAACGTGAACATCAAGCTGGACATCACCA<br>GCCACAACGAGGATTACACCATTGTCGAGCAGTACGAGCGGGCTGA<br>GGGCCGCCACTCCACCGGGGTATGGACGAGCTGTACAAGGATATCT<br>AAATGGAGGCGCTCGTTGATCTGAGCCTTGCCCCCTGACGAACGGCG<br>*GTGGATGGAAGATACTGCTCTCAAGTGCTGAAGCGGTAGCTTAGCTCC*<br>*CCGTTTCGTGCTGATCAGTCTTTTTCAACACGTAAAAAGCGGAGGAGTT*<br>*TTGCAATTTTGTTGGTTGTAACGATCCTCCGTTGATTTTGGCCTCTTTCT*<br>*CCATGGGCGGGCTGGGCGTATTTGAAGCGCTTTTGGAAAAGTTGCTGC*<br>*GGGGTTCATCAGCTGAAGGGGACTCGGTTCGCAGATCAGTTACACACT*<br>*AAAGAACGGCGGGTAGCAACACCAGCAAACGTGACGAAACGGAACCG*<br>*TGCAGCATTTAAATGGCCCGAACTTGCTCTCGGTGTCATATTGCACCAT*<br>*CCCATCTTGTATAACCGATATAACATAGCTTCGAGTGTGCCGATAAATT*<br>*ATTGTGAGGGCGTCGGGGGGCGAGCTGAGGGAAATGGAGGGGGCAC*<br>*TCATCTCGGCCGCCCCTCCCATCGCGACCTCGGCGCTCAAGCGGGGG*<br>*TCCCGCACTCGCTTCGGTCTCTTTTGGTCAGCAGCCGTTTGTTGACTAC*<br>*CGTTAATTAAA*<u>ATGAGCCGGCTGGATAAGTCCAAGGTCATCAACTCCG</u><br><u>CGCTCGAGCTGCTCAACGAGGTCGGGATCGAGGGCCTGACGACCCG</u><br><u>GAAGCTGGCGCAGAAGCTGGGGGTGGAGCAGCCGACCCTGTACTGG</u><br><u>CACGTCAAGAACAAGCGGGCCCTGCTCGATGCCCTCGCTATCGAGAT</u><br><u>GCTCGATCGGCATCATACGCATTTTTGCCCTCTCGAGGGGGAGTCCT</u><br><u>GGCAGGACTTTCTGCGGAACAACGCCAAGTCGTTCCGGTGCGCCCTG</u><br><u>CTGTCCCATCGGGATGGTGCTAAGGTCCATCTCGGGACGCGGCCTAC</u><br><u>CGAGAAGCAGTACGAGACCCTGGAGAACCAGCTCGCTTTTCTGTGCC</u><br><u>AGCAGGGGTTCTCCCTGGAGAACGCTCTCTACGCCCTCTCCGCTGTG</u><br><u>GGTCATTTTACCCTCGGTTGCGTCCTGGAGGATCAGGAGCATCAGGT</u><br><u>CGCCAAGGAAGGAGCGGGAGACCCCTACCACGGACTCGATGCCCCT</u><br><u>CTCCTCCGGCAGGCTATTGAGCTGTTTGACCATCAGGGCGCGGAGCC</u><br><u>TGCCTTTCTCTTTGGGCTCGAGCTGATTATTTGCGGCCTCGAGAAGCA</u><br><u>GCTCAAGTGCGAGTCCGGTTCGGAGCTCCCTCCTAAGAAGAAGCGCA</u><br><u>AGGTGAGCACCGCCCCCCCCACGGATGTGTCCCTGGGTGATGAGCTG</u><br><u>CATCTCGACGGCGAGGATGTCGCCATGGCTCATGCCGATGCCCTGGA</u><br><u>TGATTTCGATCTCGATATGCTGGGTGATGGTGACTCCCCCGGTCCGG</u><br><u>GTTTTACGCCTCACGATAGCGCCCCTTACGGCGCTCTGGACATGGCC</u><br><u>GATTTTGAGTTTGAGCAGATGTTCACGGACGCGCTCGGCATCGACGA</u><br><u>GTACGGCGGT</u>*TAAACGCGT*GGCCCCACCGTTGCGTGTGCGCCCGCGG<br>*TGCGCTGCGCGGTCGGCAGCTTGGGTGTGGCATCCGGTGCGGCTTGT*<br>*CCCGCCGGCATGTAGCTCTTATGTAACGGGCTGTCTGTACTCACTTGT*<br>*GTCCAACCGCCTCTCTGGATGTCTGGTTCATGACCAACAGCTAAGCA*<br>*AAGAAGCAGCTGGGACACCAGGGGACGCTGACAATGGAGTGGGCAG* |

TABLE 5-continued

DNA sequences of the expression systems tested in *Chlamydomonas reinhardtii*. The functional DNA parts are indicated: 8 × sTF binding site (black text, bolded); core promoters (underlined); mCherry coding region (black text, bolded, underlined); terminators (italics); sTFs (bolded italics). DNA sequence of the expression system tested in *Chlamydomonas reinhardtii*

| |
|---|
| *CCGACGCAGCAGAGGGGGGACTGCGAGTTATACGGTATTAGGCTGG* *GCTGGCAGGTCCGGTAGACGGTAATGCGACACACAAGCCGTGGGAG* *AAGGTTGCGTCAGGAAGTCCAAGCAGGTTCTGT* CG (SEQ ID NO: 74) |

TABLE 6

DNA sequence of the expression systems tested in Chinese hamster ovary cells (CHO cells - *Cricetulus griseus*). The functional DNA parts are indicated: 8 × sTF binding site (black, text, bolded); core promoters (underlined); mCherry coding region (black text, bolded, underlined); terminators (italics); sTF (bolded italics). DNA sequence of the expression system tested in the CHO cells (*Cricetulus griseus*)

| | |
|---|---|
| 8BS(BM3R1) -<br>Mm-<br>Eef2-cp -<br>mCherry +<br>Mm-<br>Atp5b-cp -<br>BM3R1_VP64 | TTTGCTCGGCTAGTCGGAATGAACATTCATTCCGAGACCTAGGATGTG<br>ACGGAATGAAGGTTCATTCCGGACTCTAGATAAGCACGGAATGAACTT<br>TCATTCCGCTGAAGCTTGTCAATCGGAATGAAGGTTCATTCCGGCTAG<br>TCGGAATGAACATTCATTCCGAGACCTAGGATGTGACGGAATGAAGGT<br>TCATTCCGGACTCTAGATAAGCACGGAATGAACTTTCATTCCGCTGAA<br>GCTTGTCAATCGGAATGAAGGTTCATTCCGGCTAGTTCTCCCCGGAAA<br>CTG<u>CCGGACGAGCACCCGGCGCCGTCACGTGACGCACCCAACCGGC</u><br><u>GTTGACCTATAAAAGGCCGGGCGTTGACGTCAGCGGTCTCTTCCGCCG</u><br><u>CAGCCGCCGCCATCGTCGGCGCGCTTCCCTGTTCACCTCTGACTCTGA</u><br><u>GAATCCGTCGCCATCCGCCACC</u>ATGGATCCGTGTCTAAAGGGGAGG<br>AAGACAACATGGCTATTATTAAGGAGTTCATGAGGTTTAAGGTGCATA<br>TGGAGGGGAGCGTAAACGGTCACGAATTTGAGATTGAAGGCGAAGG<br>GGAAGGAAGACCCTATGAAGGTACTCAAACTGCAAAACTCAAGGTCA<br>CCAAAGGTGGACCACTGCCCTTCGCTTGGGATATACTTAGCCCACAG<br>TTTATGTACGGGTCTAAAGCCTATGTAAAGCATCCAGCAGATATACCA<br>GACTACCTTAAACTGAGCTTTCCTGAAGGTTTTAAGTGGGAGCGGGTG<br>ATGAATTTCGAAGACGGTGGCGTGGTTACCGTTACCCAGGACAGCAG<br>TTTGCAAGATGGAGAATTTATCTACAAGGTAAAACTGCGGGGACCA<br>ATTTCCCAAGTGACGGACCCGTAATGCAGAAAAAGACTATGGGGTGG<br>GAGGCTTCTTCAGAACGCATGTACCCCGAAGACGGTGCTCTGAAAGG<br>CGAAATAAAGCAACGATTGAAGCTCAAAGATGGGGGCCATTACGACG<br>CCGAGGTAAAAACTACCTATAAAGCCAAAAAGCCTGTTCAGCTGCCT<br>GGTGCTTATAATGTGAATATAAAGTTGGACATAACCTCACATAACGAA<br>GATTACACTATTGTTGAACAGTACGAGAGAGCAGAGGGGCGGCATTC<br>TACAGGAGGGATGGACGAACTGTACAAATAAGATATC*TTCCCCAAAGC*<br>*CACGTGACTTTACTGGTCACTGAGGCAGTGCATGCATGTCAGGCTGCC*<br>*TTCATCTTTTCTATAAGTTGCACCAAAACATCTGCTTAAGTTCTTTAATTT*<br>*GTACCATTTCTTCAAATAAAGAATTTTGGTACCCAGCTTCTTTTCTTTGT*<br>*GATTGAGGATAAGCATTCCAGCTTCCAGTTGCTTCACCGCCAGTTATAC*<br>*TAATCACACTGAAACACCTAAAAGAATATTCACGTTTATTAAACTCCTTA*<br>*GTTTGGGAAAGATCGTAAAATACAGGTGTTTTCAGGCAGGACTATTAAG*<br>*TACTCTTGGTTCTGAGTTACATGCTAGACTGTCGTGGGAACACACTCCT*<br>*GGGTGTCGCTGCTTGTGTGCCTTTGACTGGGTCAGTGATTTAAATA*<u>TTG</u><br><u>GCACCAGTTTAGACCAATAGCTGATAAGCTCCGAGTTTTTTTACCCTAT</u><br><u>AGAAGCGTTAGTGGTGATGACGAACAGCAAAATCACCCAATTACTGTG</u><br><u>CCTACGGCGGAGGTTGCCCCGCCCCAGCTGCAGGACCGGCGGAGAG</u><br><u>GACCGCTTCGGCGCTCAGTCTCCACCCGGATTCCGCC</u>*ATGGAAAGCA*<br>*CACCAACAAAGCAAAAAGCAATATTTTCAGCCTCACTTCTTTTGTTTG*<br>*CCGAGAGGGGTTTCGACGCTACAACAATGCCCATGATAGCCGAAAAT*<br>*GCCAAAGTAGGAGCCGGGACAATATACAGGTATTTTAAAAACAAGGA*<br>*AAGTCTGGTCAATGAACTTTTCCAGCAGCACGTAAATGAGTTTCTTCA*<br>*ATGTATTGAATCTGGCCTGGCTAACGAACGCGACGGTTATCGTGATG*<br>*GCTTTCATCACATATTTGAGGGAATGGTCACTTTCACCAAAAATCACC*<br>*CTAGGGCCTTGGGCTTTATCAAAACACATTCTCAGGGTACATTCCTCA*<br>*CCGAGGAATCTCGACTCGCCTATCAAAAGCTCGTTGAGTTTGTCGTA*<br>*CTTTCTTTAGGGAGGGACAAAAGCAAGGCGTAATCCGAAACTCCCA*<br>*GAGAACGCCTTGATCGCTATTCTCTTCGGATCTTTTATGGAGGTCTAT*<br>*GAGATGATCGAAAATGACTATCTTAGTCTGACAGATGAGCTTCTGACA*<br>*GGTGTTGAAGAATCATTGTGGGCTGCTTTGTCTAGACAGAGTGAATTC*<br>*CCTCCCAAGAAGAAACGAAAGGTAAGCGCCTCTGGTTCAGGTCGTGC*<br>*TGACGCTCTGGATGATTTTGATCTCGACATGCTTGGTTCTGATGCTCTT*<br>*GACGACTTCGACCTTGATATGCTGGGCAGTGACGCATTGGACGACTT*<br>*TGATTTGGACATGTTGGGAGCGATGCCTTGGACGACTTTGACCTTGA*<br>*TATGCTGATAAATAGTCGC*TAATAG*CTCGAGCGCCTCCTCCTCCCATA* |

TABLE 6-continued

DNA sequence of the expression systems tested in Chinese hamster ovary cells (CHO cells - *Cricetulus griseus*). The functional DNA parts are indicated: 8 × sTF binding site (black, text, bolded); core promoters (underlined); mCherry coding region (black text, bolded, underlined); terminators (italics); sTF (bolded italics). DNA sequence of the expression system tested in the CHO cells (*Cricetulus griseus*)

GCCGATGGCCACAGTCAATTCACCACCCCAGGGTCCTCAGCTAGGAG
GAGGACAGAGTGTGGAAAGTAGACAGTTTCCACTTCCTTTTCCCTACA
TCTTTCAGTATGAGGGTACCATATCCTGCTCCACCCAGGTCCTGTGGA
TAACAATAAAAAAGGAAGTGTGTGTGCCTTTGTATGTGTTCCCCTCAC
GTCTTTGACAATGGGGTTGGGGAGGTCTGGGGTCAGAGAGAATTGCG
TTGTGGGATTTTGAGTTAACTGCTTTTGGCTTTAGAGATCGACAGTCTA
AGAGGTAAAATTAGATGTGAATTAGTTGGGAAGCTGCCAAGTGTCCC
AGAGCTTTGGACACCCACTCTAGGGACACATTGTCCCCTT*ATTTAAAT
AGGGCCCGTTTAAACC* (SEQ ID NO: 75)

EXAMPLES

Example 1

The Bacterial DNA-Binding Proteins and their Binding Sites Used in the Expression Systems:

LexA (transcription repressor from *Escherichia coli*; GenBank: EDV67321.1) LexA binding sites (regardless of the DNA strand):

CTGTATATAAACACAG; (SEQ ID NO: 76)

CTGTATATATACCCAG; (SEQ ID NO: 77)

CTGTATATAAACCAG; (SEQ ID NO: 78)

GTGGTTATATATACAG (SEQ ID NO: 79)

SrpR (transcriptional regulator from *Pseudomonas putida*; NCBI Reference Sequence: WP_019437727.1)
SrpR binding sites (regardless of the DNA strand):

ATATACATACATGCTTGTTTGTTTGTAAAC; (SEQ ID NO: 80)

ATTTACATACATTCTTGTTTGTTTGTAAAC (SEQ ID NO: 81)

PhlF (transcriptional regulator from *Pseudomonas protegens*; GenBank: AAF20928.1)
PhlF binding sites (regardless of the DNA strand):

ATGATACGAAACGTACCGTATCGTTAAGGT; (SEQ ID NO: 82)

ATGATACGGAACGTTACGTATCGTTAAGCT; (SEQ ID NO: 83)

ATGATACGGAAGCTACCGTATCGTAAAGGT; (SEQ ID NO: 84)

ATGATACGTAACGTACCGTATCGTAAAGGT (SEQ ID NO: 85)

TetR (transcriptional regulator from *Escherichia coli*; GenBank: EFK45326.1)
TetR binding site (regardless of the DNA strand):

ACTCCCTATCAGTGATAGAGA (SEQ ID NO: 86)

BM3R1 (transcriptional regulator from *Bacillus megaterium*; NCBI Reference Sequence: WP_013083972.1)
BM3R1 binding sites (regardless of the DNA strand):

CGGAATGAAGGTTCATTCCG; (SEQ ID NO: 87)

CGGAATGAACTTTCATTCCG; (SEQ ID NO: 88)

CGGAATGAACATTCATTCCG; (SEQ ID NO: 89)

CGGAATGAACGTTCATTCCG (SEQ ID NO: 90)

TarA (transcriptional regulator *Streptomyces lavenduligriseus*; NCBI Reference Sequence: WP_030788560.1)
TarA binding sites (regardless of the DNA strand):

AACATACCGTGTGGTATGTT; (SEQ ID NO: 91)

AACATACCGAGTGGTATGTT; (SEQ ID NO: 92)

AACATACCGTGAGGTATGTT; (SEQ ID NO: 93)

AAACATACCGTGTGGTATGTTC (SEQ ID NO: 94)

LacI (lac repressor from *Escherichia coli*; NCBI Reference Sequence: WP 048339836.1)
LacI binding site (regardless of the DNA strand):

AATTGTGAGCGGCTCACAATT (SEQ ID NO: 95)

Example 2

Test of Different Versions of the sTFs and Assessment of Modulation of the Expression System Performance in *Saccharomyces cerevisiae*. (FIG. 5)

The expression systems (individual expression cassettes for the sTFs and for the reporters) were constructed as two separate DNA molecules (plasmids) (FIG. 5A). The plasmids with the expression cassettes for each sTF contained: 1) the *Saccharomyces cerevisiae* codon-optimized coding region of the DNA binding protein (LexA, PhlF, SrpR, TetR, BM3R1, and TarA; Example 1) in each sTF coding region, 2) NLS and the VP16 activation domain in each sTF coding region, 3) the Sc-TDH3 cp (Table 1) controlling the expression of each sTF, 4) the URA3 selection marker gene (of *Kluyveromyces lactis* origin), 5) the flanks for integration into the genome by homologous recombination into the ura3-52 locus (for replacing the mutated coding region of the locus), 6) regions needed for propagation of the plasm id in *E. coli*. The plasm ids with the reporter cassettes contained 1) the *Saccharomyces cerevisiae* codon-optimized coding region of the Venus (yellow fluorescent) protein, 2) the Sc-ENO1 cp (Table 1) controlling the expression of Venus together with 3) upstream positioned sTF-specific binding sites (0, 1, 2, 4, or 8) (Example 1), 4) the LEU2 selection marker gene (of *Kluyveromyces lactis* origin), 5) the flanks for integration into the genome by homologous recombination into the leu2-3_112 locus (replacing the mutated coding region of the locus), and 6) regions needed for propagation of the plasm id in *E. coli*.

*Saccharomyces cerevisiae* CEN.PK (MATα, ura3-52 leu2-3_112 his3Δ1 MAL2-8C SUC2) was used as the parental strain. The expression cassettes (FIG. 5A) were introduced into cells through transformation of the linearized integrative plasmids, the sTF and the corresponding reporter expression cassettes were transformed into a single strain. Each integration cassette was released by NotI restriction endonuclease from the plasmid prior to the transformation. Transformations were performed using the standard lithium acetate protocol. The single copy integrations were confirmed by qPCR, where the qPCR signal of the Venus gene was compared to a qPCR signal of a unique native sequence in each strain.

For all cultivations, 6.7 g/L of yeast nitrogen base (YNB, Becton, Dickinson and Company), synthetic complete amino acid mixture lacking uracil and leucine supplemented with 20 g/L D-glucose (SCD-LU) was used. In case of agar plate cultivations, 20 g/L agar was used in addition to the above mentioned components.

Pre-cultures of the tested strains were grown for 24-48 hours on the SCD-LU agar plates prior to inoculation of 4 ml of SCD-LU in 24-well cultivation plates to OD600=0.2. The cultures were grown for 18 hours at 800 rpm (Infors HT Microtron) and 28° C. in triplicates, centrifuged, washed, and resuspended in 0.2 ml of sterile water. Two hundred µl of the cell suspension was analysed in black 96-well (Black Cliniplate; Thermo Scientific) using the Varioskan (Thermo Electron Corporation) fluorimeter. The settings for Venus were 510 nm (excitation) and 530 nm (emission), respectively. For normalization of the fluorescence results, the analyzed cell-suspensions were diluted 100× and OD600 was measured in transparent 96-well microtiter plates (NUNC) using Varioskan (Thermo Electron Corporation).

The results from the fluorescent analysis are shown in FIG. 5B.

Example 3

Quantitative Analysis of the Expression System Performance in Diverse Fungal Hosts (FIG. 6)

The expression systems (Table 2, FIG. 4) and their negative control versions (the expression systems with deleted regions spanning the core promoter controlling the sTF and the sTF itself) were cloned into plasmids introducing selection markers and genome-integration flanks for 6 different species. 1) *Saccharomyces cerevisiae* CEN.PK strain was used as the parental strain. The expression systems (including the versions with the *Saccharomyces cerevisiae* codon-optimized coding region of the DNA binding protein, BM3R1), including the LEU2 selection marker gene (of *Kluyveromyces lactis* origin), were integrated into the leu2-3_112 locus (replacing the mutated coding region of the locus) using the corresponding flanking regions for homologous recombination. The transformations were done by the standard lithium acetate protocol. 2) *Aspergillus niger* ATCC1015 strain was used as the parental strain. The expression systems, including a hygromycin-resistance selection marker gene with a suitable promoter and terminator, were integrated into gaaC locus (replacing the native coding region) using the corresponding flanking regions for homologous recombination. The transformations were carried out by using the CRISPR transformation protocol (see below), including: protoplasts of the *A. niger* strain, linear donor DNA (expression cassette with the selection marker and the integration flanks), protein Cas9 (IDT) and mix of synthetic crRNA and tracrRNA (IDT). Cas9, crRNA and tracrRNA form a ribonucleoprotein (RNP) complex that generates a double-stranded brake at the target genomic locus which is then repaired with the linear donor DNA by homologous recombination. 3) *Trichoderma reesei* strain M124 (VTT culture collection) was used as the parental strain. The expression systems, including a hygromycin-resistance selection marker gene with a suitable promoter and terminator, were integrated into pep4 locus (replacing the native coding region) using the corresponding flanking regions for homologous recombination. The transformations were done by using the CRISPR transformation protocol (see below), including: protoplasts of the *T. reesei* strain, linear donor DNA (expression cassette with the selection marker and flanking regions) and RNP complex that generates a double-stranded brake at the target genomic locus which is then repaired with the linear donor DNA. 4) *Pichia kudriavzevii* ATCC 32196 strain was used as the parental strain. The expression systems, including a hygromycin-resistance selection marker gene with a suitable promoter and terminator, were integrated into PDC1 locus (replacing the native coding region) using corresponding flanking regions for homologous recombination. The transformations were done by using the standard lithium acetate protocol. 5) *Pichia pastoris* X-33 strain (Invitrogen) was used as the parental strain. The expression systems (with the coding region of the DNA binding protein, BM3R1, that was codon-optimized to fit the codon usage of *Saccharomyces cerevisiae*), including a zeocin-resistance selection marker gene with suitable promoter and terminator, were integrated into the AOX1 locus (integration into the AOX1 promoter region) using the corresponding flanking regions for homologous recombination. The transformations were done by using the standard lithium acetate protocol. 6) *Yarrowia lipolytica* C-00365 (VTT culture collection) was used as the parental strain. The expression systems, including a nourseothricin-resistance selection marker gene with a suitable promoter and terminator, were integrated into the ANTI locus (replacing the native coding region) using the corresponding flanking regions for homologous recombination. The transformations were done by using the standard lithium acetate protocol.

The CRISPR transformation protocol: Isolated protoplasts were suspended into 200 µl of STC solution (1.33 M sorbitol, 10 mM Tris-HCl, 50 mM $CaCl_2$), pH 8.0). One hundred µl of protoplast suspension was mixed with 3.5 µg of donor DNA and 20 µl of RNP-solution (1 µM Cas9 protein (IDT), 1 µM synthetic crRNA (IDT), and 1 µM tracrRNA (IDT)) and 100 µl of the transformation solution (25% PEG 6000, 50 mM $CaCl_2$), 10 mM Tris-HCl, pH 7.5). The mixture was incubated on ice for 20 min. Two ml of transformation solution was added and the mixture was incubated 5 min at room temperature. Four ml of STC was added followed by addition of 7 ml of the molten (50° C.) top agar (200 g/L D-sorbitol, 6.7 g/L of yeast nitrogen base (YNB, Becton, Dickinson and Company), synthetic complete amino acid, 20 g/L D-glucose, 400 mg/L (for *A. niger*) or 100 mg/L (for *T. reesei*) of hygromycin B, and 20 g/L agar). The mixture was poured onto a hygromycin selection plate (200 g/L D-sorbitol, 6.7 g/L of yeast nitrogen base (YNB, Becton, Dickinson and Company), synthetic complete amino acid, 20 g/L D-glucose, 400 mg/L (for *A. niger*) or 100 mg/L (for *T. reesei*) of hygromycin B, 20 g/L agar). Cultivation was done at +28° C. for five or seven days, colonies were picked and re-cultivated on the YPD plates containing 400 mg/L (for *A. niger*) or 100 mg/L (for *T. reesei*) of hygromycin B.

The correct integrations were confirmed by PCR of the genomic DNA of each transformed strain, where the amplicon (amplified DNA region) spanned the integrated construct and the genomic DNA outside of the integration flanks. The single copy integrations were confirmed by qPCR, where the qPCR signal of the mCherry gene was compared to a qPCR signal of a unique native sequence in each host.

For the liquid cultivations, 6.7 g/L of yeast nitrogen base (YNB, Becton, Dickinson and Company), synthetic complete amino acid supplemented with 20 g/L D-glucose (SCD) was used. In case of agar plate cultivations, solidified medium containing 20 g/L agar, 20 g/L bacto peptone (Becton Dickinson), 10 g/L yeast extract, and 20 g/L D-glucose (YPD plates). To obtain spores of the filamentous fungi, PDA agar plates were used for sporulation (39 g/L BD-Difco Potato dextrose agar).

For the flow-cytometry analysis of the mCherry production in the tested strains (FIG. 6A), pre-cultures of the tested yeast strains were grown for 24-48 hours on YPD agar plates and the filamentous fungi (*A. niger* and *T. reesei* strains) were sporulated on PDA plates (7 days), spores collected, and diluted in 1×PBS prior to analysis. In case of yeasts strains, 4 ml of SCD medium in 24-well cultivation plates was inoculated from pre-cultures to OD600=0.2 by every tested yeast strain. The cultures were grown for 18 hours at 800 rpm (Infors HT Microtron) and 28° C. One hundred μL of the culture was combined with 1.5 mL of 1×PBS prior to analysis. Measurements were done with FACSAria III (BD), where 10000 events were recorded and results were normalized by dividing mCherry fluorescence values by cell size (forward scatter, FSC-A). The results from the flow-cytometry fluorescent analysis are shown in FIG. 6A.

For the quantitative fluorometry analysis (FIG. 6B), pre-cultures of the tested yeast strains were grown for 24-48 hours on YPD agar plates and pre-cultures (inoculated by spores) of *Trichoderma reesei* strains were grown for 24 hours in YPG medium (20 g/L bacto peptone, 10 g/L yeast extract, and 30 g/L gelatin). Four ml of the SCD medium in 24-well cultivation plates was inoculated to OD600=0.2 by every tested yeast strain (OD600=0.5 in case of *T. reesei*). The cultures were grown for 18 hours at 800 rpm (Infors HT Microtron) and 28° C. in triplicates, centrifuged, washed, and resuspended in 0.2 ml of sterile water. Two hundred μl of each cell suspension was analyzed in black 96-well plates (Black Cliniplate; Thermo Scientific) using the Varioskan (Thermo Electron Corporation) fluorimeter. The settings for mCherry were 587 nm (excitation) and 610 nm (emission), respectively. For normalization of the fluorescence results, the analyzed cell-suspensions were diluted 100× and OD600 was measured in transparent 96-well microtiter plates (NUNC) using Varioskan (Thermo Electron Corporation). The results from the analysis are shown in FIG. 6B.

Example 4

Analysis of the Adjustable Expression Levels in Different Hosts (*Pichia kudriavzevii, Aspergillus Niger*, and *Trichoderma reesei*) (FIG. 7)

The expression systems for *Pichia kudriavzevii* and *Aspergillus niger* with diverse numbers of the sTF-specific binding sites (0, 1, 2, 4, or 8) (FIG. 7A) were constructed analogously to the Example 3 (the version of the expression system A shown in FIG. 4 was used). In case of *Pichia kudriavzevii*, the ATCC 32196 strain was used as the parental strain. The expression systems, including hygromycin-resistance selection marker gene with a suitable promoter and terminator, were integrated into PDC1 locus (replacing the native coding region) using the corresponding flanking regions for homologous recombination. The transformations were done using the standard lithium acetate protocol. In case of *Aspergillus niger*, the ATCC1015 strain was used as the parental strain. The expression systems, including a hygromycin-resistance selection marker gene with a suitable promoter and terminator, were integrated into the gaaC locus (replacing the native coding region) using the corresponding flanking regions for homologous recombination. The transformations were done using the CRISPR transformation protocol, including: protoplasts of the *A. niger* strain, linear donor DNA (expression cassette with the selection marker and the integration flanks) and RNP complex that generates a double-stranded brake at the target genomic locus which is then repaired with the linear donor DNA.

The DNA molecule, containing the expression systems for *Trichoderma reesei* for adjustable expression of the CBH1 gene (FIG. 7C), contained the 201 cp (Table 1) together with upstream positioned BM3R1-specific binding sites (0, 1, 2, 4, or 8) controlling the expression of the CBH1 coding region, the *T. reesei* PDC1 terminator, 533 cp (Table 1) controlling the expression of the sTF coding region, the sTF coding region, the *Trichoderma reesei* TEF1 terminator, the hygromycin-resistance selection marker gene with suitable promoter and terminator, and the flanks for integration into the genome by homologous recombination into the CBH1 locus (replacing the native coding region). The *T. reesei* strain M124 (VTT culture collection) was used as the parental strain. The transformations were done by the protoplast transformation protocol (see below), including: protoplasts of the *T. reesei* strain and linear donor DNA (expression cassette with the selection marker and the integration flanks).

The protoplast transformation protocol: Isolated protoplasts were suspended into 200 μl of STC solution (1.33 M sorbitol, 10 mM Tris-HCl, 50 mM $CaCl_2$), pH 8.0). One hundred μl of protoplast suspension was mixed with 10 μg of the donor DNA and 100 μl of the transformation solution (25% PEG 6000, 50 mM $CaCl_2$), 10 mM Tris-HCl, pH 7.5). The mixture was incubated on ice for 20 min. Two ml of transformation solution was added and the mixture was incubated 5 min at room temperature. Four ml of STC was added followed by addition of 7 ml of the molten top agar (200 g/L D-sorbitol, 6.7 g/L of yeast nitrogen base (YNB, Becton, Dickinson and Company), synthetic complete amino acid, 20 g/L D-glucose, 100 mg/L hygromycin B, 20 g/L agar). The mixture was poured onto a selection plate (200 g/L D-sorbitol, 6.7 g/L of yeast nitrogen base (YNB, Becton, Dickinson and Company), synthetic complete amino acid, 20 g/L D-glucose, 100 mg/L hygromycin B, and 20 g/L agar). Cultivation was done at +28° C. for five days; colonies were picked and re-cultivated on the YPD plates containing 100 mg/L hygromycin B.

The correct integrations were confirmed by PCR of the genomic DNA of each transformed strain, where the amplicon (amplified DNA region) spanned the integrated construct and the genomic DNA outside of the integration flanks. The single copy integrations were confirmed by qPCR, where the qPCR signal of the mCherry gene (for *Pichia kudriavzevii* and *Aspergillus niger* strains) or the BM3R1 coding region (for *Trichoderma reesei* strains) was compared to a qPCR signal of a unique native sequence in each host.

For liquid cultivations, 6.7 g/L of yeast nitrogen base (YNB, Becton, Dickinson and Company), synthetic complete amino acid supplemented with 20 g/L D-glucose (SCD) was used. In case of agar plate cultivations, solidified medium containing 20 g/L agar, 20 g/L bacto peptone (Becton Dickinson), 10 g/L yeast extract, and 20 g/L D-glucose (YPD plates) was used. To obtain spores of the filamentous fungi, PDA agar plates were used for sporulation (39 g/L BD-Difco Potato dextrose agar).

For the flow-cytometry analysis of mCherry production in the tested strains (FIG. 7B), pre-cultures of the *Pichia kudriavzevii* strains were grown for 24-48 hours on the YPD agar plates and the *Aspergillus niger* strains were sporulated on PDA plates (for 7 days), spores collected, and diluted in 1×PBS prior to analysis. In case of the *Pichia kudriavzevii* strains, 4 ml of the SCD medium in 24-well cultivation plates was inoculated from pre-culture to OD600=0.2. The cultures were grown for 18 hours at 800 rpm (Infors HT Microtron) and 28° C. One hundred μL of the culture was combined with 1.5 mL of 1×PBS prior to analysis. Measurements were done with FACSAria III (BD), where 10000 events were recorded and results were normalized by dividing mCherry fluorescence values by cell size (forward scatter, FSC-A). The results from flow-cytometry fluorescent analysis are shown in FIG. 7B.

For the western blot analysis of the CBH1 production in the *Trichoderma reesei* strains, pre-cultures (inoculated by spores) were grown for 24 hours in YPG medium (20 g/L bacto peptone, 10 g/L yeast extract, and 30 g/L gelatine). Four ml of either SGE-lactose (15 g/L $KH_2PO_4$, 5.4 g/L $Na_2SO_4$, 1 mL/L trace elements (3.7 mg/L $CoCl_2$, 5 mg/L $FeSO_4 \cdot 7H_2O$, 1.4 mg/L $ZnSO_4 \cdot 7H_2O$, 1.6 mg/L $MnSO_4 \cdot 7H_2O$), 40 g/L lactose, 333.25 g/L spent grain extract, 8.6 g/L $(NH_4)_2$-citrate, 100 mM PIPPS, 2.4 mM $MgSO_4$, and 4.1 mM $CaCl_2$), pH adjusted to 4.8 with KOH) or the SCD medium in 24-well cultivation plates was inoculated to OD600=0.5 for each tested strain. The cultures were grown for 3 days at 800 rpm (Infors HT Microtron) and 28° C., centrifuged, and the supernatant transferred into a clean tube. Fifteen μL of each supernatant was mixed with 4 μL of 4×SDS loading buffer (400 ml/L glycerol, 100 ml/L β-mercaptoethanol, 2 g/L OrangeG dye (Sigma), 40 g/L SDS, and 125 mM Tris-HCl pH 6.8), boiled and loaded on the 4-20% SDS-PAGE gradient gel. The gel was transferred onto a nitrocellulose membrane, and the CBH1 protein was detected with specific (mouse) anti-CBH1 primary antibody (and anti-mouse-IR680-conjugated secondary antibody), and visualization of the signal was performed on the Odyssey CLx Imaging System instrument (LICOR Biosciences). The results from the analysis are shown in FIG. 7D.

Example 5

Test of the Expression System in *Kazachstania exigua* (FIG. 8)

The expression system used for *Kazachstania exigua* (Table 3, FIG. 8A) was cloned into a plasmid containing flanking regions for the *K. exigua* gene g706 encoding a homolog of *S. cerevisiae* ALD2. In the resulting construct, *K. exigua* g706 3'-UTR flanking region formed a terminator sequence for the sTF in the expression system. The expression system, including flanking regions for homologous recombination, was integrated into the g706 locus (replacing the native coding region).

*Kazachstania exigua* C-02458 (VTT culture collection) strain was modified by the replacement of both KU70 loci with the Cas9 expression cassette (containing suitable promoter and terminator). The resulting strain (MAT a/a ura3Nura36 ku70,6::Cas9/ku70::Cas9) was used as the parental strain (WT in FIG. 8B). Transformation of the expression system (donor DNA) into the background strain was carried out together with a centromeric plasmid containing URA3 selection marker and an expression cassette for a sgRNA that targets Cas9 into the g706 locus (sgRNA was expressed under the control of *S. cerevisiae* RNA polymerase III promoter SNR52 and terminator SUP4). The resulting strain is shown as "SES" in FIG. 8B.

Transformation was done by the electroporation protocol: Cells were inoculated in YPD medium and cultivated overnight at 250 rpm and 30° C. The overnight culture was diluted to an OD600=0.2 and grown to an OD600=1.3. The harvested and washed cells were resuspended in 10 mL Tris-EDTA (pH 7.5) containing 10 mM dithiothreitol and incubated at 30° C. for 30 minutes. Forty mL of ice cold water was added to cells followed by centrifugation. This was followed with two washing steps, first with 50 mL of ice cold sterile water, then with 10 mL of ice cold 1 M sorbitol. Finally, cells were resuspended in 125 μL of ice cold 1 M sorbitol. Fifty μL of cell suspension was combined with 15 μL of a DNA mix (containing 5 μg of the donor DNA and 5 μg of the gRNA plasmid). Electroporation was performed in 2 mm cuvettes at 1.25 kV, 200 S2 and 25 μF. Nine hundred fifty μL of recovery solution (10 g/L yeast extract, 10 g/L Bacto peptone, 20 g/L glucose, 1 M sorbitol) was added immediately after electroporation. The cells were recovered for 30 minutes at 250 rpm and 30° C. before plating on SCD medium lacking uracil.

For expression analysis, the two strains (WT and SES) were cultivated in triplicates in SCD medium for 10 hours, and the SES strain also for 22 hours to reach stationary phase when all glucose had been consumed ("SES_stat" in the FIG. 8B). Total RNA was isolated from the strains (RNeasy Kit—QIAGEN), cDNA was produced (Transcriptor First Strand cDNA Synthesis Kit Roche), and transcription of the Venus and the ADH1 (a glycolytic gene highly expressed in exponential growth phase and down-regulated in the absence of glucose) genes were analyzed by qPCR with primers specific for each gene. The ALG9 gene was used as the normalization control for expression quantification. The results from the analysis are shown in FIG. 8B.

Example 6

The Expression System Used for Production of a Secreted Protein in Fungi (*Trichoderma Reesei* and *Pichia pastoris*) (FIG. 9)

The DNA molecule, containing the expression system for *Trichoderma reesei* (FIG. 9A), contained the 114 cp (Table 1) together with upstream positioned eight BM3R1-specific binding sites controlling the expression of the CBH1 coding region, the coding region for the CBH1 gene, the *Trichoderma reesei* PDC1 terminator, 533 cp (Table 1) controlling the expression of the sTF coding region, the sTF coding region, the *Trichoderma reesei* TEF1 terminator, the hygromycin-resistance selection marker gene with a suitable promoter and terminator, and flanking regions for genomic integration into the CBH1 locus (replacing the native coding region) by homologous recombination. The *T. reesei* strain M1763 (VTT culture collection) was used as the parental strain ("WT" in FIG. 9B). Transformations were done by the protoplast transformation protocol (Example 4), using protoplasts of the *T. reesei* strain and linear donor DNA (expression cassette with the selection marker and integration flanks).

The correct integrations were confirmed using PCR from genomic DNA, where the amplicon (amplified DNA region) spanned the integrated construct and the genomic DNA outside of the integration flanks. Single copy integration was tested using qPCR, where the qPCR signal from the BM3R1 coding region was compared to the signal from a unique native sequence in the host. The strain containing the expression cassette ("SES" in the FIG. 9B) was analyzed for the CBH1 production and compared to the background strain in cellulase-inducing and repressing conditions.

The CBH1 production in *Trichoderma reesei* strains was carried out in 1 L bioreactors. Pre-cultures (inoculated with spores) for the cellulase-inducing conditions cultivations were grown for 24 hours in SGE-lactose medium (Example 4) to produce sufficient amount of mycelium for bioreactor inoculations. Pre-cultures (inoculated with spores) for the cellulase-repressing conditions cultivations were grown for 24 hours in YE-glucose-A medium (20 g/L glucose, 10 g/L yeast extract, 15 g/L $KH_2PO_4$, 5 g/L $(NH_4)_2SO_4$, 1 mL/L trace elements (3.7 mg/L $CoCl_2$, 5 mg/L $FeSO_4.7H_2O$, 1.4 mg/L $ZnSO_4.7H_2O$, 1.6 mg/L $MnSO_4.7H_2O$), 2.4 mM $MgSO_4$, and 4.1 mM $CaCl_2$), pH adjusted to 4.8). The cellulase-inducing bioreactor cultivations were inoculated in SGM medium ("SGM" in FIG. 9B) (20 g/L spent grain extract, 20 g/L sold spent grain, 60 g/L lactose, 5 g/l $KH_2PO_4$, 5 g/l $NR_4SO_4$, 1 mL/L trace elements, 2.4 mM $MgSO_4$, and 4.1 mM $CaCl_2$), 1 mL/L Antifoam J647, pH 4.8), air flow at 0.5 slpm (0.4-0.6 vvm), and stirring at 600 rpm. The cellulase-repressing bioreactor cultivations were inoculated in the YE-glucose-B medium ("glucose" in FIG. 9B) (10 g/L glucose, 20 g/L yeast extract, 5 g/L $KH_2PO_4$, 5 g/L $NR_4SO_4$, 1 mL/L trace elements, 2.4 mM $MgSO_4$, and 4.1 mM $CaCl_2$), 1 mL/L Antifoam J647, pH 4.8), and these cultures were continuously fed with glucose (300 g/L glucose with flow rate at 4.4 g/h), air flow at 0.5 slpm (0.4-0.6 vvm), and stirring at 900 rpm. The cultivation was carried out for 150 hours, samples taken at various times, subset shown in FIG. 9B.

For the coomassie stain analysis (FIG. 9B upper left panel), 1.54 of each culture (time-point) supernatant was mixed with 15 μL of 1×SDS loading buffer (100 ml/L glycerol, 25 ml/L β-mercaptoethanol, 0.5 g/L OrangeG dye (Sigma), 10 g/L SDS, and 31.2 mM Tris-HCl pH 6.8), boiled and loaded on the 4-20% SDS-PAGE gradient gel together with dilutions of purified CBH1 protein as a standard. The gel was stained with colloidal coomassie stain (PageBlue Protein Staining Solution; Thermo Fisher Scientific) according to the manufacture's protocol. The visualization of the stained gel was performed on the Odyssey CLx Imaging System instrument (LI-COR Biosciences). Protein concentration in the culture supernatant was estimated from the CBH1 standard in the same gel (FIG. 9B upper right table). For the western analysis (FIG. 9B lower left panel), 0.0754 of each culture (time-point) supernatant was mixed with 154 of 1×SDS loading buffer, boiled and loaded on the 4-20% SDS-PAGE gradient gel together with dilutions of purified CBH1 protein. The gel was transferred onto a nitrocellulose membrane, and the CBH1 protein was detected with specific (mouse) anti-CBH1 primary antibody (and anti-mouse-IR680-conjugated secondary antibody), and the visualization of the signal was performed on the Odyssey CLx Imaging System instrument (LI-COR Biosciences). The CBH1 concentration in the culture supernatant was estimated (FIG. 9B lower right table).

The DNA molecule, containing the expression system for *Pichia pastoris* (FIG. 9C), consisted of the 201 cp (Table 1) together with upstream positioned eight BM3R1-specific binding sites controlling expression of the fusion protein coding region, the coding region for the fusion protein (consisting of N-terminal *Saccharomyces cerevisiae* secretion signal (a-factor), KEX/spe13 protease cleavage site, carbohydrate-binding module (CBM), elastin-like protein (ELP5), and another CBM), followed by the *S. cerevisiae* ADH1 terminator, 008 cp (Table 1) controlling the expression of the sTF coding region, the sTF coding region (the coding region of the DNA binding protein, BM3R1, of the sTF was codon-optimized to fit the codon usage of *Saccharomyces cerevisiae*), the *Trichoderma reesei* TEF1 terminator, the zeocin-resistance selection marker gene with suitable promoter and terminator, and the flanks for integration into the genome by homologous recombination into the AOX1 locus (integration into the AOX1 promoter region). Transformations were done by using the standard lithium acetate protocol. The strain containing a single copy of the expression cassette was tested for production of the protein in diverse conditions (FIG. 9D).

The CBM-ELP5-CBM production in *Pichia pastoris* was carried out in Erlenmeyer flasks. The pre-culture was done for 24 hours in the YPP medium (10 g/L yeast extract, 20 g/L peptone, 13.4 g/L yeast nitrogen base, 0.4 mg/L biotin, 20 g/L glycerol, 13.2 mM $K_2HPO_4$, and 86.8 mM $KH_2PO_4$, pH=6.0) with 20 g/L glycerol (YPP-Gly). To test the effect of different carbon sources, glycerol was replaced either by 20 g/L glucose ("YPP-Glc" in FIG. 9D) or by 20 g/L ethanol ("YPP-EtOH" in FIG. 9D). The cells from the pre-culture were inoculated (to OD600=1.0) in YPP-Gly, YPP-Glc, or YPP-EtOH and cultured for 2 days, also addition of protease inhibitors (chymostatin and pepstatin) was tested. The pre-culture was also cultivated for additional two days (three days in total).

For the western analysis (FIG. 9D), 22.5 μL of each culture supernatant was mixed with 7.54 of 4×SDS loading buffer, boiled and loaded on the 4-20% SDS-PAGE gradient gel. The gel was transferred onto a nitrocellulose membrane, and the CBM-ELP5-CBM protein was detected with specific (mouse) anti-CBM primary antibody (and anti-mouse-IR680-conjugated secondary antibody), and the visualization of the signal was performed on the Odyssey CLx Imaging System instrument (LI-COR Biosciences) (FIG. 9D).

Example 7

Test of the Expression System Performance in Plant Organism (*Nicotiana benthamiana*)

Two expression systems are tested in *Nicotiana benthamiana* (Table 4): The expression systems assembled in single DNA molecules comprise two expression cassettes: 1) sTF expression cassette, which comprises a core promoter used for the sTF expression control, exemplified here with the At-RPL41D_cp (Table 1); the sTF version with the DNA-binding protein, exemplified here by either BM3R1 or TetR, and with the activation domain, exemplified here by either VP16AD or VP64AD; and a terminator, exemplified here by the *Arabidopsis thaliana* MT3 terminator. And 2) the target gene expression cassette, which comprises a number of sTF specific binding sites, exemplified here by either eight BM3R1-specific binding sites or by eight TetR-specific binding sites; another core promoter, exemplified here by At-ATTI7_cp (see Table 1), the target gene coding region, exemplified here by the mCherry (red fluorescent protein reporter) coding region; and a terminator, exemplified here by the *Arabidopsis thaliana* PSBX terminator. The coding regions of the sTFs and the mCherry are codon-optimized to fit the codon usage of *Nicotiana benthamiana*. Also, negative control versions (the expression systems with deleted regions spanning the At-RPL41D_cp, the sTF, and the MT3 terminator) are constructed.

The expression systems (and the negative control versions) are cloned into a plasmid containing the plant (NptII) selectable marker coding region with suitable promoter and terminator, and the sequences for propagation in *Agrobacterium tumefaciens*, including kanamycin selection marker. The plasm ids are transformed into *Agrobacterium tumefaciens* (strain EHA105) by electroporation (2 mm cuvettes; with settings: 1.25 kV, 200 S2 and 25 µF), and the transformants are grown in presence of kanamycin and rifampicin prior to infection of *Nicotiana benthamiana* leaves. The leaves of 6-weeks-old plants are infiltrated with the 1:1 mixture of the *Agrobacterium tumefaciens* cultures, one with the strain carrying the expression system and the other with a strain carrying an expression vector for post transcriptional gene silencing inhibitor p19 (Silhavy et al., 2002) (both cultures diluted to OD600=0.7 with 10 mM MgCl2+10 mM MES–pH=5.8). The infiltrated leaf discs (corresponding to the infiltrated area) are harvested after 6 days incubation in a greenhouse, grinded in 1×PBS, and the crude extracts are analysed for mCherry fluorescence using the Varioskan instrument (Thermo Electron Corporation).

Example 8

Test of the Expression System Performance in Green Algae (*Chlamydomonas Reinhardtii*)

Two expression systems are tested in *Chlamydomonas reinhardtii* (Table 5): The expression systems assembled in single DNA molecules comprise two expression cassettes: 1) sTF expression cassette, which comprises a core promoter used for the sTF expression control, exemplified here with the Cr-eIF-5A_cp (Table 1); the sTF version with the DNA-binding protein, exemplified here by either BM3R1 or TetR, and with the activation domain, exemplified here by either VP16AD or VP64AD; and a terminator, exemplified here by the *Chlamydomonas reinhardtii* RPS27A terminator. And 2) the target gene expression cassette, which comprises a number of sTF specific binding sites, exemplified here by either eight BM3R1-specific binding sites or by eight TetR-specific binding sites; another core promoter, exemplified here by Cr-RPS3A_cp (Table 1), the target gene coding region, exemplified here by the mCherry (red fluorescent protein reporter) coding region; and a terminator, exemplified here by the *Chlamydomonas reinhardtii* RBCS2 terminator. The coding regions of the sTFs and the mCherry are codon-optimized to fit the codon usage of *Chlamydomonas reinhardtii*. Also, negative control versions (the expression systems with deleted regions spanning the Cr-eIF-5A_cp, the sTF, and the RPS27A terminator) are constructed.

The expression systems (and the negative control versions) are cloned into the NcoI site of the plasmid pChlamy_4 (Invitrogen). The resulting plasmids (including unmodified pChlamy_4 plasmid), after linearization, are transformed into *Chlamydomonas reinhardtii* (strain 137c; Invitrogen). The transformations are performed according to protocol in the GeneArt *Chlamydomonas* Protein Expression Kit manual (Invitrogen). The transformants are grown in the Gibco Tap Growth medium in presence of Zeocin and analyzed for mCherry fluorescence using the Varioskan instrument (Thermo Electron Corporation).

Example 9

Test of the Expression System Performance in CHO Cells (*Cricetulus griseus*)

Expression system for *Cricetulus griseus* (Table 6) assembled in single DNA molecules comprises two expression cassettes: 1) sTF expression cassette, which comprises a core promoter used for the sTF expression control, exemplified here with the Mm-Atp5b_cp (Table 1); the sTF version with the DNA-binding protein, exemplified here by BM3R1, and with the activation domain, exemplified here by VP64AD; and a terminator, exemplified here by the *Mus musculus* INHA terminator. And 2) the target gene expression cassette, which comprises a number of sTF specific binding sites, exemplified here by either eight BM3R1-specific binding sites; another core promoter, exemplified here by Mm-Eef2_cp (Table 1), the target gene coding region, exemplified here by the mCherry (red fluorescent protein reporter) coding region; and a terminator, exemplified here by the *Mus musculus* FTH1 terminator. The coding regions of sTF and mCherry are codon-optimized to fit the codon usage of *Cricetulus griseus*. Also, negative control versions (the expression systems with deleted regions spanning the Mm-Atp5b_cp, the sTF, and the INHA terminator) are constructed.

The expression system (and the negative control version) is cloned between MluI and XbaI sites of the plasmid pcDNA3.1 (Invitrogen). The resulting plasmids are transfected into Chinese hamster ovary cells (CHO-K1; American Type Culture Collection (Rockville, Md.)). Prior to the transformation, the CHO-K1 cells are cultured in Ham's F-12K (Kaighn's) Medium (Gibco) containing 2 mM L-glutamine and 1500 mg/L sodium bicarbonate, supplemented with 10% fetal bovine serum (FBS), 100 U/ml of penicillin, and 100 mg/mL of streptomycin.

The cells are maintained in an atmosphere of 5% $CO_2$ and 90% relative humidity at 37° C. A flask of cells are cultured, split, and $3 \times 10^5$ cells are seeded into 6-well culture plates and grown in 2 ml of medium until 70% confluent. The transfection is done with FuGene 6 (Roche) according to the manufacturer's instructions with approximately 1 µg of plasmid DNA added per well. The transfected cells are allowed to continue growing for up to 5 days. The mCherry expression is monitored daily post transfection by fluorescence microscopy.

LITERATURE REFERENCES

1. Hubmann G, Thevelein J, Nevoigt E (2014) Natural and Modified Promoters for Tailored Metabolic Engineering of the Yeast *Saccharomyces cerevisiae*. In: Mapelli V, editor. Yeast Metabolic Engineering: Springer New York. pp. 17-42.
2. Blumhoff M, Steiger M G, Marx H, Mattanovich D, Sauer M (2013) Six novel constitutive promoters for metabolic engineering of *Aspergillus niger*. Appl Microbiol Biotechnol 97(1):259-67.
3. Ito Y, Yamanishi M, Ikeuchi A, Matsuyama T (2015) A highly tunable system for the simultaneous expression of multiple enzymes in *Saccharomyces cerevisiae*. ACS Synth Biol 4: 12-16.
4. Pachlinger R, Mitterbauer R, Adam G, Strauss J (2005) Metabolically independent and accurately adjustable *Aspergillus* sp. expression system. Appl Environ Microbiol 71: 672-678.

5. Silhavy D, Molnar A, Lucioli A, Szittya G, Hornyik C, Tavazza M, Burgyan J. (2002) A viral protein suppresses RNA silencing and binds silencing-generated, 21- to 25-nucleotide double-stranded RNAs. EMBO J. 21(12): 3070-80.

PATENT REFERENCES

US2002081667

The invention claimed is:

1. An expression system for a eukaryotic host, comprising:
   (a) an expression cassette comprising a core promoter, and a DNA sequence encoding a synthetic transcription factor (sTF), said core promoter being the only regulatory sequence for controlling expression of the DNA sequence encoding the synthetic transcription factor, and
   (b) one or more expression cassettes, each comprising a DNA sequence encoding a desired product and being operably linked to a synthetic promoter, said synthetic promoter comprising the core promoter identified in (a) or another core promoter different from the core promoter identified in (a), and sTF-specific binding sites upstream of the core promoter identified in (a) or upstream of the other core promoter different from the core promoter identified in (a).

2. The expression system according to claim 1, wherein the core promoter comprises a DNA sequence containing a 5'upstream region of a eukaryotic gene, starting 10-50 bp upstream of a TATA-box and ending 9 bp upstream of an ATG start codon, and wherein distance between the TATA-box and the start codon is no greater than 180 bp and no smaller than 80 bp, and a DNA sequence at 3' end comprising random 1-20 bp.

3. The expression system according to claim 1, wherein the core promoter is a universal core promoter (UCP) functional in eukaryotic organisms.

4. The expression system according to claim 1, wherein said synthetic transcription factor (sTF) comprises a prokaryotic transcription regulator, a nuclear localization signal, and a transcription activation domain.

5. A eukaryotic host cell, comprising the expression system of claim 1.

6. The eukaryotic host cell according to claim 5, wherein the core promoter is a universal core promoter (UCP) functional in eukaryotic organisms.

7. The eukaryotic host cell of claim 5, wherein the eukaryotic host is selected from the group consisting of fungal species including yeast and filamentous fungi, plant species including flowering plants and green algae species, and animal species.

8. The expression system of claim 1, wherein the eukaryotic host is selected from the group consisting of fungal species including yeast and filamentous fungi, plant species including flowering plants and green algae species, and animal species.

9. An in vitro method for producing a desired protein product in a eukaryotic host cell the method comprising cultivating a eukaryotic host cell under suitable cultivation conditions, said eukaryotic host cell comprising an expression system comprising:
   (a) an expression cassette comprising a core promoter, and a DNA sequence encoding a synthetic transcription factor (sTF), said core promoter being the only regulatory sequence for controlling expression of the DNA sequence encoding the synthetic transcription factor, and
   (b) one or more expression cassettes, each comprising a DNA sequence encoding a desired protein product and being operably linked to a synthetic promoter, said synthetic promoter comprising the core promoter identified in (a) or another core promoter different from the core promoter identified in (a), and sTF-specific binding sites upstream of the core promoter identified in (a) or upstream of the other core promoter different from the core promoter identified in (a).

* * * * *

SEQUENCE LISTING

```
<160> NUMBER OF SEQ ID NOS: 95

<210> SEQ ID NO 1
<211> LENGTH: 165
<212> TYPE: DNA
<213> ORGANISM: Artificial Sequence
<220> FEATURE:
<223> OTHER INFORMATION: DNA sequence based on Saccharomyces cerevisiae
      THI4 core promoter

<400> SEQUENCE: 1
atcatgaaat tgattttttg attttcaatt tatgaactac ccagatatat aaatattgga    60
ataaattgtg tattaagtag tcgggaaata tcttttatgt tctctttctt atcatctaga   120
aataataaat cacaaccaaa aaaatcaact aacttaatta aaatg                   165

<210> SEQ ID NO 2
<211> LENGTH: 154
<212> TYPE: DNA
<213> ORGANISM: Artificial Sequence
<220> FEATURE:
<223> OTHER INFORMATION: DNA sequence based on Saccharomyces cerevisiae
      TEF1 core promoter

<400> SEQUENCE: 2
ctctttcgat gacctcccat tgatatttaa gttaataaac ggtcttcaat ttctcaagtt    60
tcagtttcat ttttcttgtt ctattacaac ttttttttact tcttgctcat tagaaagaaa   120
gcatagcaat ctaatctaag ttttaattaa aatg                               154

<210> SEQ ID NO 3
<211> LENGTH: 203
<212> TYPE: DNA
<213> ORGANISM: Artificial Sequence
<220> FEATURE:
<223> OTHER INFORMATION: DNA sequence based on Saccharomyces cerevisiae
      TDH3 core promoter

<400> SEQUENCE: 3
agctgaaaaa aaaggttgaa accagttccc tgaaattatt ccctacttg actaataagt     60 atataaagac ggtaggtatt gattgtaatt ctgtaaatct atttcttaaa cttcttaaat   120
tctactttta tagttagtct ttttttagt tttaaaacac caagaactta gtttcgaata    180
aacacacata attaattaaa atg                                           203

<210> SEQ ID NO 4
<211> LENGTH: 203
<212> TYPE: DNA
<213> ORGANISM: Artificial Sequence
<220> FEATURE:
<223> OTHER INFORMATION: DNA sequence based on Saccharomyces cerevisiae
      ENO1 core promoter

<400> SEQUENCE: 4
tctccccgga aactgtggcc ttttctggca cacatgatct ccacgatttc aacatataaa    60
tagcttttga taatggcaat attaatcaaa tttattttac ttctttcttg taacatctct   120
```

```
cttgtaatcc cttattcctt ctagctattt ttcataaaaa accaagcaac tgcttatcaa      180
cacacaaaca cttaattaaa atg                                              203
```

<210> SEQ ID NO 5
<211> LENGTH: 203
<212> TYPE: DNA
<213> ORGANISM: Artificial Sequence
<220> FEATURE:
<223> OTHER INFORMATION: DNA sequence based on Saccharomyces cerevisiae
      PGK1 core promoter

<400> SEQUENCE: 5

```
aaggggtgg tttagtttag tagaacctcg tgaaacttac atttacatat atataaactt       60
gcataaattg gtcaatgcaa gaaatacata tttggtcttt tctaattcgt agttttcaa      120 gttcttagat gctttctttt tctcttttt acagatcatc aaggaagtaa ttatctactt      180
tttacaacaa attaattaaa atg                                              203
```

<210> SEQ ID NO 6
<211> LENGTH: 148
<212> TYPE: DNA
<213> ORGANISM: Artificial Sequence
<220> FEATURE:
<223> OTHER INFORMATION: DNA sequence based on Aspergillus niger core
      promoter 201205

<400> SEQUENCE: 6

```
ttctcttttc ttaagaatat gttcaaagac taggatggat aaatgggta tataaagcac       60 cctgactccc ttcctccaag ttctatctaa ccagccatcc tacactctac atatccacac     120
caatctacta caattattaa ttaaaatg                                         148
```

<210> SEQ ID NO 7
<211> LENGTH: 161
<212> TYPE: DNA
<213> ORGANISM: Artificial Sequence
<220> FEATURE:
<223> OTHER INFORMATION: DNA sequence based on Aspergillus niger core
      promoter 53301

<400> SEQUENCE: 7

```
cgccccaaga gagctgaaga tgctgagtag ggttgtccag gcagcacata tataagatgc      60
ttcgtcccct cccatcgagt ccttcttttc tctctctcat caatcactct acttcctact     120
ctaccttaaa ctcttcacta cttcatacat taattaaaat g                         161
```

<210> SEQ ID NO 8
<211> LENGTH: 210
<212> TYPE: DNA
<213> ORGANISM: Artificial Sequence
<220> FEATURE:
<223> OTHER INFORMATION: DNA sequence based on Aspergillus niger core
      promoter 205017

<400> SEQUENCE: 8

```
tatagtacta ttgatttagt attgttgttg gatgtgctgg taggtgtgta gtatatatag      60
gagatagtag aggcagatga tgatgatggt actattttga atcacctcaa acgatactat     120
tcgcatcttt gataaagata tcaagaaacc agaacaatca ttactactct ccataaggat     180
atatatatac tttacatctt aattaaaatg                                       210
```

```
<210> SEQ ID NO 9
<211> LENGTH: 205
<212> TYPE: DNA
<213> ORGANISM: Artificial Sequence
<220> FEATURE:
<223> OTHER INFORMATION: DNA sequence based on Aspergillus niger core
      promoter 00850

<400> SEQUENCE: 9
aacccaaagt aataagtctg tagtaattgg tctcgccctg aattccaaac tataaatcaa      60
ccactttccc tcctcccccc cgcccccact tggtcgattc ttcgttttct ctctaccttc     120
tttctattcg gttttcttct tcttttattt tccctctccc atcaatcaaa ttcatatttg     180
aaaaaaatta acattaatta aaatg                                           205

<210> SEQ ID NO 10
<211> LENGTH: 204
<212> TYPE: DNA
<213> ORGANISM: Artificial Sequence
<220> FEATURE:
<223> OTHER INFORMATION: DNA sequence based on Aspergillus niger core
      promoter 1114556

<400> SEQUENCE: 10
ggggcggaaa cttgaaactg gacgccttgt gaacggcgta tgtggtatat aaggaaccaa      60
gtcccgctgt agtcttcggt tcatcagacc cagcacagca cagcaacaca acattacagc    120
atagcaagca cttctctata tttctacaca tcacagcaca tttctataca gtttacgtct    180
aattatctcc tgttaattaa aatg                                            204

<210> SEQ ID NO 11
<211> LENGTH: 173
<212> TYPE: DNA
<213> ORGANISM: Artificial Sequence
<220> FEATURE:
<223> OTHER INFORMATION: DNA sequence based on Aspergillus niger core
      promoter 1147651

<400> SEQUENCE: 11
gccctgcagt gcctgatcac cttatcaagt ggccaaatat cccactataa aaggcttggg      60 aaccctcgt tctgtcttac cttctatcat cttaccaaat ccactcctct tccttcatac     120
atcaatctta ccaatcaact acctctacaa ctccaataca cttaattaaa atg            173

<210> SEQ ID NO 12
<211> LENGTH: 178
<212> TYPE: DNA
<213> ORGANISM: Artificial Sequence
<220> FEATURE:
<223> OTHER INFORMATION: DNA sequence based on Aspergillus niger core
      promoter 1178623

<400> SEQUENCE: 12
ggctactcgg gttttaagcc gtcttaaaag ccgacacgaa ttagttataa aagactctgt      60
acttgagcag gatattcctt cattcttttc atttagattg atatcgaatt cattctacaa    120
ggatcggata ctcttccatc ctttattttg tctctgtgaa tcaaacttaa ttaaaatg      178

<210> SEQ ID NO 13
<211> LENGTH: 218
<212> TYPE: DNA
<213> ORGANISM: Artificial Sequence
<220> FEATURE:
<223> OTHER INFORMATION: DNA sequence based on Aspergillus niger core
      promoter 57241
```

<400> SEQUENCE: 13
aggtaatgaa tattggttgc tggcgggctg atcttctccc gacacgtcta tataaactgg     60
tcaccttctg gcccttcctt tctatctctt ccttctcatc atcagtctca aacaagcctc    120
tttctctcct accttcactc tccactttct cctttcgaaa gggataaaac tctcctcctc    180
attctcacct atatatacct tgtgctttaa ttaaaatg                            218

<210> SEQ ID NO 14
<211> LENGTH: 214
<212> TYPE: DNA
<213> ORGANISM: Artificial Sequence
<220> FEATURE:
<223> OTHER INFORMATION: DNA sequence based on Aspergillus niger core
      promoter 06590

<400> SEQUENCE: 14
gatttctaga aatttctgcc ctttacttgc cttccctctt tgtcaacaaa tataagaga      60 ctccaattcc ccttctctga tttccaacat ttttcattct ccacttcaga accatctgaa    120
ggagcttggc tgtctcgctt cttcttcttt ccttctttac taacatccct acccctcctt    180
agaaaaccaa gtctctcctc ctttaattaa aatg                                214

<210> SEQ ID NO 15
<211> LENGTH: 176
<212> TYPE: DNA
<213> ORGANISM: Artificial Sequence
<220> FEATURE:
<223> OTHER INFORMATION: DNA sequence based on Aspergillus niger core
      promoter 1141688

<400> SEQUENCE: 15
acttggatga tggaggagtt gatcgaggtc aatgaggaga ggcttgcaag tataagaaga     60
gactgctcga ccagcagaat ggatcttctt gttcatcaac caagagtcca aggcttcttt    120
gtctggttct atctcttctc cgaactctct tgcttgacat tctcttaatt aaaatg        176

<210> SEQ ID NO 16
<211> LENGTH: 160
<212> TYPE: DNA
<213> ORGANISM: Artificial Sequence
<220> FEATURE:
<223> OTHER INFORMATION: DNA sequence based on Trichoderma reesei core
      promoter 123979

<400> SEQUENCE: 16
tagccagcag tgaagaagag gggaagaaga taaacctgta ggttggacag agtgtataaa     60
agggagggct gtgcccaacg aggagcgaga ttaactttgg atttggagca gaacaatatt    120
ggaatcacaa gaagaaggat ctctgtcttt aattaaaatg                           160

<210> SEQ ID NO 17
<211> LENGTH: 192
<212> TYPE: DNA
<213> ORGANISM: Artificial Sequence
<220> FEATURE:
<223> OTHER INFORMATION: DNA sequence based on Trichoderma reesei core
      promoter 112258

<400> SEQUENCE: 17
tagccacatc cttggagatc agttgcagtc tattcattca ggctcaacat ataagatgg      60 gatacttcca acagatgata gttgtcaaac aacctctttg atcctacaca atttggccca    120
agacacacaa gacgctcaca tctcctacct aaccaaacaa agaaaaaaac atccaccaac      180
ttaattaaaa tg                                                         192

<210> SEQ ID NO 18
<211> LENGTH: 161
<212> TYPE: DNA
<213> ORGANISM: Artificial Sequence
<220> FEATURE:
<223> OTHER INFORMATION: DNA sequence based on Trichoderma reesei core
      promoter 123236

<400> SEQUENCE: 18
atcttacaaa gttgcttggc agtaaaccgt gcaatggaca ccaggtataa agtcagtgat      60
atcctccccg aattcaaagt ttcatcacca agctcctcaa tcaactctac ttgaacaata     120
ctacaaacaa ccaaacctca ttcaacaact taattaaaat g                         161

<210> SEQ ID NO 19
<211> LENGTH: 174
<212> TYPE: DNA
<213> ORGANISM: Artificial Sequence
<220> FEATURE:
<223> OTHER INFORMATION: DNA sequence based on Trichoderma reesei core
      promoter 123989

<400> SEQUENCE: 19
taaacggaat gagctagtag gcaaagtcag cgaatgtgta tatataaagg ttcgaggtcc      60
gtgcctccct catgctctcc ccatctactc atcaactcag atcctccagg agacttgtac     120
accatctttt gaggcacaga aacccaatag tcaaccgcgg acttaattaa aatg           174

<210> SEQ ID NO 20
<211> LENGTH: 204
<212> TYPE: DNA
<213> ORGANISM: Artificial Sequence
<220> FEATURE:
<223> OTHER INFORMATION: DNA sequence based on Trichoderma reesei core
      promoter 119989

<400> SEQUENCE: 20
aacagcctgc gagagctgga agatgaagag ggccagaaaa aaaagtataa agaagacctc      60
gattcccgcc atccaacaat cttttccatc ctcatcagca cactcatcta caaccatcac     120
cacattcact caactcctct ttctcaactc tccaaacaca acattctttt gttgaatacc     180
aaccatcacc acttaattaa aatg                                            204

<210> SEQ ID NO 21
<211> LENGTH: 150
<212> TYPE: DNA
<213> ORGANISM: Artificial Sequence
<220> FEATURE:
<223> OTHER INFORMATION: DNA sequence based on Trichoderma reesei core
      promoter 123232

<400> SEQUENCE: 21
ggtctggatg aaacgtcttg gccaaatcgt gatcgattga tactcgcatc tataagatgg      60
cacagatcga ctcttgattc acagacatcc gtcagccctc aagccgtttg caagtccaca     120
aacacaagca caagcatatt aattaaaatg                                      150

<210> SEQ ID NO 22
<211> LENGTH: 177
<212> TYPE: DNA
<213> ORGANISM: Artificial Sequence

```
<220> FEATURE:
<223> OTHER INFORMATION: DNA sequence based on Trichoderma reesei core
      promoter 73638

<400> SEQUENCE: 22
ccggcacaaa tcaggagcaa caggcactgc aaaatgacct ggcagtatat atagacctga    60
ccgtatgagt ctattgtaga cattctagct aagagatccg agcctagttc ataatacagt   120
agttgagttc atagcaactt cactctctag ctgaacaaat tatctttaat taaaatg      177

<210> SEQ ID NO 23
<211> LENGTH: 189
<212> TYPE: DNA
<213> ORGANISM: Artificial Sequence
<220> FEATURE:
<223> OTHER INFORMATION: DNA sequence based on Trichoderma reesei core
      promoter 123818

<400> SEQUENCE: 23
gagacgaggc aagcttgatg aggccaaatt atccgtcaac tgtcttataa aggagcccat    60
gccaaacccc ccctaaagac tcaagaagcc aaacctgaac aaccccagca cctgaacagt   120
catacaaccc ctccaagccc aaaagacaca acaactccta ctagctgaag caagaagtta   180
attaaaatg                                                            189

<210> SEQ ID NO 24
<211> LENGTH: 156
<212> TYPE: DNA
<213> ORGANISM: Artificial Sequence
<220> FEATURE:
<223> OTHER INFORMATION: DNA sequence based on Trichoderma reesei core
      promoter 123979

<400> SEQUENCE: 24
cagcagtgaa gaagagggga agaagataaa cctgtaggtt ggacagagtg tataaaaggg    60
agggctgtgc ccaacgagga gcgagattaa ctttggattt ggagcagaac aatattggaa   120
tcacaagaag aaggatctct gtctttaatt aaaatg                              156

<210> SEQ ID NO 25
<211> LENGTH: 154
<212> TYPE: DNA
<213> ORGANISM: Artificial Sequence
<220> FEATURE:
<223> OTHER INFORMATION: DNA sequence based on Trichoderma reesei core
      promoter 69465

<400> SEQUENCE: 25 gaaaatggt gaggagatct gccttcgagt gcgtgtagaa aaatgtatat aaggatgtgt     60
ttcactcaac ttgtcttaag aatcggttct ctagccgcgc tttcaattac ttcgagactt   120
tcgcttaaaa tcgccctgcc atttaattaa aatg                                154

<210> SEQ ID NO 26
<211> LENGTH: 183
<212> TYPE: DNA
<213> ORGANISM: Artificial Sequence
<220> FEATURE:
<223> OTHER INFORMATION: DNA sequence based on Trichoderma reesei core
      promoter 49976

<400> SEQUENCE: 26
tgcccctggc gttgcaagcc gcgtacaact gcccttttac ctaggtataa agacctgta    60 gtaaccaact actattgcaa ttcttcttca cgtgggcatc tattcgtatc ttacacaagg   120
```

```
gcgctgcaac taattgactt gatcttccat ctcgtgtctt gcttgtaacc attaattaaa    180
atg                                                                  183

<210> SEQ ID NO 27
<211> LENGTH: 204
<212> TYPE: DNA
<213> ORGANISM: Artificial Sequence
<220> FEATURE:
<223> OTHER INFORMATION: DNA sequence based on Trichoderma reesei core
      promoter 123946

<400> SEQUENCE: 27
ctgttaggct gtgagttata aaggttgatg gattgggtcg aggttgtcaa tgtcagagca     60
tcttacctct cacgcttcaa tcttacctac acgcttcctc tcaatccttg aacaccaatt    120
gttgctctag cgcctatcct tcactcatca ctcgcctcgt acactaaact cttcatcccg    180
aacagacacg gcttaattaa aatg                                           204

<210> SEQ ID NO 28
<211> LENGTH: 189
<212> TYPE: DNA
<213> ORGANISM: Artificial Sequence
<220> FEATURE:
<223> OTHER INFORMATION: DNA sequence based on Arabidopsis thaliana CRA1
      core promoter

<400> SEQUENCE: 28
aagtcataaa tagcaattta agtgaagtgt aaattgtaca tagtcgactc tatatacctg     60
gttcttatct cattcaattt atcctcaaca actttaatag aaaatatca aataaattcc    120 ctataaatag cttcacataa tgcaagtgag aaaccacaaa aagtaagaaa tataagatta    180
attaaaatg                                                            189

<210> SEQ ID NO 29
<211> LENGTH: 214
<212> TYPE: DNA
<213> ORGANISM: Artificial Sequence
<220> FEATURE:
<223> OTHER INFORMATION: DNA sequence based on Arabidopsis thaliana
      RPL41D core promoter

<400> SEQUENCE: 29
atcccctctg gcaaattctt atccatttgg gtttttattgg gcttttgaaa taataaagcc     60
cattaagtta gttactaggg ttttgttgtt gtttaaagga ggaataagag cgtaagctac    120
aaaatctttc tattcatctc cgccgctcct catcctgtaa agctaaacaa ataatcagag    180
gaacgaagga gacagcttct gcttaattaa aatg                                214

<210> SEQ ID NO 30
<211> LENGTH: 183
<212> TYPE: DNA
<213> ORGANISM: Artificial Sequence
<220> FEATURE:
<223> OTHER INFORMATION: DNA sequence based on Arabidopsis thaliana
      ATTI7 core promoter

<400> SEQUENCE: 30
gaatttgtgg ttctcgtgaa gtcgtgataa tagtttgtcc aagcgataaa tataaaatag     60
tattgcacct caacaagtgt taagcatgca aatccattta cgcatacata ttaactccga    120
gtgaaatata aatattagag agtagagaca gagaaaaaga cagagacaaa gttaattaaa    180
atg                                                                  183
```

<210> SEQ ID NO 31
<211> LENGTH: 234
<212> TYPE: DNA
<213> ORGANISM: Artificial Sequence
<220> FEATURE:
<223> OTHER INFORMATION: DNA sequence based on Arabidopsis thaliana
      THI1 core promoter

<400> SEQUENCE: 31

```
atcgttactt tccattgatg gctaaaaatt aaataatcca cgataaatat taataataca    60
aaaaacaatt aaaataacaa aaaaagatca aaaattctct aacccttcat tccttatctc   120
tgacgtggcc atcaatcttc agattttctt cttcttctaa tttaaatact caacaaccac   180
tcttcacttc accatcagca tcactaaact cgaacccctaa agttaattaa aatg         234
```

<210> SEQ ID NO 32
<211> LENGTH: 167
<212> TYPE: DNA
<213> ORGANISM: Artificial Sequence
<220> FEATURE:
<223> OTHER INFORMATION: DNA sequence based on Arabidopsis thaliana
      MT2B core promoter

<400> SEQUENCE: 32

```
gtggacaaag atcgttgaca cgtggacggt ctacaaattc taattttgcc tataaatatc    60
aaagctcctg aatatgtaag tttcattcac tgattatcgt ttaaggcaaa ttaagatcat   120
cttcataaat cttctcagat ctcttccaat tttctttaat taaaatg                  167
```

<210> SEQ ID NO 33
<211> LENGTH: 185
<212> TYPE: DNA
<213> ORGANISM: Artificial Sequence
<220> FEATURE:
<223> OTHER INFORMATION: DNA sequence based on Arabidopsis thaliana
      TCTP1 core promoter

<400> SEQUENCE: 33

```
ccaaaattgt aatttaccga gaattgtaaa tttacctgaa aaccctacgc tatagtttcg    60
actataaata ccaaacttag gacctcactt cagaatcccc tcgtcgctgc gtctctctcc   120
cgcaaccttc gattttcgtt tattcgcatc catcggagag agaaaacaat caattaatta   180
aaatg                                                                185
```

<210> SEQ ID NO 34
<211> LENGTH: 238
<212> TYPE: DNA
<213> ORGANISM: Artificial Sequence
<220> FEATURE:
<223> OTHER INFORMATION: DNA sequence based on Arabidopsis thaliana
      RPL26A core promoter

<400> SEQUENCE: 34

```
gaattaactt ttactaggcc agaagtgtag ctaacataga agaggcccat tataaaactc    60
tttaaaatca aaatctaaaa caggcccagc ccattcataa caaagcccta atatatcgag   120
taaacctagc tccactcaaa acctaactat ataaccttca cacacactca taacctcttc   180
ctcatcccct taaaaaaccc taagagtaga gactctctca atcccgttaa ttaaaatg     238
```

<210> SEQ ID NO 35
<211> LENGTH: 188
<212> TYPE: DNA
<213> ORGANISM: Artificial Sequence
<220> FEATURE:
<223> OTHER INFORMATION: DNA sequence based on Arabidopsis thaliana
      MED37E core promoter

<400> SEQUENCE: 35 accaatttt gaccgtccga tggaaactct agcctcaacc caaaactcta tataaagaaa    60
tcttttcctt cgttattgct taccaaatac aaaccctagc cgccttattc gtcttcttcg   120
ttctctagtt ttttcctcag tctctgttct tagatccctt gtagtttcca aatctttaa   180 ttaaaatg                                                            188

<210> SEQ ID NO 36
<211> LENGTH: 165
<212> TYPE: DNA
<213> ORGANISM: Artificial Sequence
<220> FEATURE:
<223> OTHER INFORMATION: DNA sequence based on Arabidopsis thaliana
      AT1G15270 core promoter

<400> SEQUENCE: 36
atacactttc agagcccatt taataggttg cgttgttact acgaactcat tataaatatg    60
aaccgtagcc ccaatcagag agattcgata ccgtctgcaa ctctcagcta cttttccc    120 aattttgagc tcaacatcga accctagctc aacttaatta aaatg                  165

<210> SEQ ID NO 37
<211> LENGTH: 236
<212> TYPE: DNA
<213> ORGANISM: Artificial Sequence
<220> FEATURE:
<223> OTHER INFORMATION: DNA sequence based on Arabidopsis thaliana
      FKBP12 core promoter

<400> SEQUENCE: 37
tctgcttctt aattcggtct ggtacagtat tatattatcc acctttgaga agaataaat    60 aatgggccta aatttcatcg aatttgggttt tggattattg ttaggcccag atagggttta  120
gatcaaacag catgataatt gataaataac aaaatatata ggcaaaagct actccgagat  180
tcgaagctgc aaagaacgcg aaacagtgag agagacagag agaattaatt aaaatg      236

<210> SEQ ID NO 38
<211> LENGTH: 155
<212> TYPE: DNA
<213> ORGANISM: Artificial Sequence
<220> FEATURE:
<223> OTHER INFORMATION: DNA sequence based on Arabidopsis thaliana
      AT4G25140 core promoter

<400> SEQUENCE: 38
caattgcatg atgtctccat tgacacgtga cttctcgtct cctttcttaa tatatctaac   60
aaacactcct acctcttcca aaatatatac acatcttttt gatcaatctc tcattcaaaa  120
tctcattctc tctagtaaac aagttaatta aaatg                             155

<210> SEQ ID NO 39
<211> LENGTH: 216
<212> TYPE: DNA
<213> ORGANISM: Artificial Sequence
<220> FEATURE:
<223> OTHER INFORMATION: DNA sequence based on Arabidopsis thaliana
      DRT112 core promoter

<400> SEQUENCE: 39

```
atgccatgtc acgacacagt atctaaaatc aaccaatcac aacgcgtctt tatagataac    60
ttgttttttt atggagtttg cttttagagc catccattgt cctatctcac tttctctctt   120
tcaccacata aaaactcata aactcgatcg aaccaaagct aaacgaaaaa cttaaaaccc   180
aaatcttatc actactctaa aagattaatt aaaatg                             216
```

<210> SEQ ID NO 40
<211> LENGTH: 222
<212> TYPE: DNA
<213> ORGANISM: Artificial Sequence
<220> FEATURE:
<223> OTHER INFORMATION: DNA sequence based on Arabidopsis thaliana
      AT1G13930 core promoter

<400> SEQUENCE: 40

```
ttttcacatt tacgtctaca atcacaatgt atgttattta gaacaataat tatagtggct    60
taaaaatcat taatgaaagt agataatagt atacttttc tttttctttg tgtggccaac   120
atatccattt tctagtctat atatacacat atccatctct taactcttcc atccaaaaaa   180
aacaaaacaa aaattatat tcaagagaaa ttaattaaaa tg                       222
```

<210> SEQ ID NO 41
<211> LENGTH: 145
<212> TYPE: DNA
<213> ORGANISM: Artificial Sequence
<220> FEATURE:
<223> OTHER INFORMATION: DNA sequence based on Arabidopsis thaliana
      RPL14B core promoter

<400> SEQUENCE: 41

```
tatttagtaa agataggccc aaaccacaaa accctagaat gaagattata tatagtgcaa    60
aacctaatcg atttttttcct ctgctgtcgc tcgtctacat ttacactcgg agcttagacc   120
ttccaatcta ccgttaatta aaatg                                         145
```

<210> SEQ ID NO 42
<211> LENGTH: 148
<212> TYPE: DNA
<213> ORGANISM: Artificial Sequence
<220> FEATURE:
<223> OTHER INFORMATION: DNA sequence based on Arabidopsis thaliana
      BDF2 core promoter

<400> SEQUENCE: 42

```
ttaaaaatgc aattctctaa tagactatca aatatcccga tacctctttta tatagtgcca    60 tcttcatcct tagtaatgta cacacacaca cataacactt atttccaact ctgtctctct   120
caattttctt tctcttttaa ttaaaatg                                      148
```

<210> SEQ ID NO 43
<211> LENGTH: 240
<212> TYPE: DNA
<213> ORGANISM: Artificial Sequence
<220> FEATURE:
<223> OTHER INFORMATION: DNA sequence based on Chlamydomonas reinhardtii
      eIF-5A core promoter

<400> SEQUENCE: 43

```
cgacgaaggg atgtctccgc aaggcaagta tataacggct agcaacgtat gccttagcat    60
agtagagcaa ttagttgtct atgtgcctcg gtgcaagcgc acacgccggg aataatgcgg   120
```

```
catggggget tctgttggcc ccatgcgagc ccccaggaag aaaagtcgcg cggcgcccgt    180
attctgccct cttgctgtgc caacctccta gtcgcttctt cgcacttttt aattaaaatg    240
```

<210> SEQ ID NO 44
<211> LENGTH: 223
<212> TYPE: DNA
<213> ORGANISM: Artificial Sequence
<220> FEATURE:
<223> OTHER INFORMATION: DNA sequence based on Chlamydomonas reinhardtii
    RPS27E1 core promoter

<400> SEQUENCE: 44

```
ggatggtgcc aagggtccgg gtcaccgagt agcattggcc cactctaaga tataagttga     60
gccgtgttta acttgttgca acatcaggcc tcgcgcgcaa cgtcaggaat ggctgcatgg    120
ggccaccgta ccatggcgcg gagggagggt attgtcgctg agcgcgactc agagctccct    180
ctccttttgc tgaccgcgga gcctgcccct cttaattaaa atg                      223
```

<210> SEQ ID NO 45
<211> LENGTH: 221
<212> TYPE: DNA
<213> ORGANISM: Artificial Sequence
<220> FEATURE:
<223> OTHER INFORMATION: DNA sequence based on Chlamydomonas reinhardtii
    RPS8 core promoter

<400> SEQUENCE: 45

```
ctgttctgga cgggtccaat gagcccgctc taaataaacg tctaggagaa gcagttaacc     60
taagggaagg tggcagcagg ggagagaggg agagagggag cgggtccatt gctccagggc    120
gagccggaat ggggccggcg ctgcctgggc tttgtccggc tgcagacaca cggctctttc    180
tctttccatt ccttaggggc tgggaacggt taattaaat g                         221
```

<210> SEQ ID NO 46
<211> LENGTH: 237
<212> TYPE: DNA
<213> ORGANISM: Artificial Sequence
<220> FEATURE:
<223> OTHER INFORMATION: DNA sequence based on Chlamydomonas reinhardtii
    RPS3A core promoter

<400> SEQUENCE: 46

```
ccgaacttgc tctcggtgtc atattgcacc atcccatctt gtataaccga tataacatag     60
cttcgagtgt gccgataaat tattgtgagg gcgtcggggg gcgagctgag ggaaatggag    120
ggggcactca tctcggccgc ccctcccatc gcgacctcgg cgctcaagcg ggggtcccgc    180
actcgcttcg gtctcttttg gtcagcagcc gtttgttgac taccgttaat taaaatg      237
```

<210> SEQ ID NO 47
<211> LENGTH: 199
<212> TYPE: DNA
<213> ORGANISM: Artificial Sequence
<220> FEATURE:
<223> OTHER INFORMATION: DNA sequence based on Chlamydomonas reinhardtii
    RPL17 core promoter

<400> SEQUENCE: 47

```
aagcggacag aaatttagtt caggaagaat tgtcagattt gctactggca tataattttt     60
tctgcagggt ctggcgtgga agaatgccaa atgcgcgga gctggctgca tgggcgcca     120 cctcccagca agggccacca ctgcaacctg ctctttctct ttcgtcgcgc cttgcacgta    180
gcgttaatta attaaaatg                                                 199
```

<210> SEQ ID NO 48
<211> LENGTH: 225
<212> TYPE: DNA
<213> ORGANISM: Artificial Sequence
<220> FEATURE:
<223> OTHER INFORMATION: DNA sequence based on Chlamydomonas reinhardtii
      RPL19 core promoter

<400> SEQUENCE: 48
agaacgcgcc tagtactcat gccacgagag tttcatcatt ccagcatgca taataaattt      60
gtcactcagg cagagcattt gcggggcgcg caatgtttag cggggcccaa agtcgccatc     120
gcggtcgcgc ccccatgcag cgttccaccc tggctttcag gcgcgggcgc acctggacta     180
tcccttcctt tgcgtcgtcc gcttgcaaac agattaatta aaatg                    225

<210> SEQ ID NO 49
<211> LENGTH: 229
<212> TYPE: DNA
<213> ORGANISM: Artificial Sequence
<220> FEATURE:
<223> OTHER INFORMATION: DNA sequence based on Chlamydomonas reinhardtii
      RPS24 core promoter

<400> SEQUENCE: 49
agcgagcgaa ctagtctcgc gccccggccc cccgtcgcc aacagaccgc tataaccaag       60
taattttgtg tggctttatt tgtattgcta aaaaccccg agcggggtga gcccaagaca      120
agaaacgaag gcggcccct cctggagcaa tgggcgtctg agagacgggg caagaccagg      180
gagagtccca gcctcctccc tctttctctt ggcacactta attaaaatg                229

<210> SEQ ID NO 50
<211> LENGTH: 226
<212> TYPE: DNA
<213> ORGANISM: Artificial Sequence
<220> FEATURE:
<223> OTHER INFORMATION: DNA sequence based on Chlamydomonas reinhardtii
      RPS15 core promoter

<400> SEQUENCE: 50
tctaggaggg gttttcccctt gtttagccct atataacgta aagctcacac tttgaatgag    60
caacataaat tatatttagt gcgaaagccg gctatgaaaa tggacatggg gatcgcgatg    120 ggcgccccg cgcctggcg gcggtgtgca caggagcgag gccctcgcct gctccttcct      180
ctttctctcg ccgtcaggct cgtagtttca aaagttaatt aaaatg                   226

<210> SEQ ID NO 51
<211> LENGTH: 226
<212> TYPE: DNA
<213> ORGANISM: Artificial Sequence
<220> FEATURE:
<223> OTHER INFORMATION: DNA sequence based on Chlamydomonas reinhardtii
      ATPC core promoter

<400> SEQUENCE: 51
cgtgcaagct actcccaggc tcctgcattc tataagcgta attttatgcc gggtatgctt     60
gtgatttgac gaagatctac tcgacggcgt tctggtgggc aaaatcggag gcaaacccaa    120
ttggcccccc tggagtgata agtcctgggt gccaagtgcg caagtgaagc cttgaactgc    180
gcctttcctt gcaccttgtt cgccgctctt tctattaatt aaaatg                   226

```
<210> SEQ ID NO 52
<211> LENGTH: 224
<212> TYPE: DNA
<213> ORGANISM: Artificial Sequence
<220> FEATURE:
<223> OTHER INFORMATION: DNA sequence based on Chlamydomonas reinhardtii
      RPS9 core promoter

<400> SEQUENCE: 52
gcagaagggt gccaaaggga ggctctaagc agtccaggcg ggcacaaaca tataaagctg     60
aagctagtgg tatacctaaa ttaattttgg ggcgctccac tgaaaaatgg actgcctgca    120
tgggccctgt acggcttcgc cgagcgagcc cggtgcaagg gccgcgaccg tgcataagtc    180
tctctctttc aagttggcag agggagcgcc agttaattaa aatg                     224

<210> SEQ ID NO 53
<211> LENGTH: 179
<212> TYPE: DNA
<213> ORGANISM: Artificial Sequence
<220> FEATURE:
<223> OTHER INFORMATION: DNA sequence based on Chlamydomonas reinhardtii
      RPL10a core promoter

<400> SEQUENCE: 53
ctgggcctta ctttcatcat agggaaagca taaatcataa cagtgtagtt tatattatgc     60
atgatgtctt ccgcagaaga ggcaccgtga tgcccaccgc ccccatgcat caattgtgag    120
ggtcaagagc gcccgcggac ccctggacat tccttttcct tgggtgatta attaaaatg     179

<210> SEQ ID NO 54
<211> LENGTH: 172
<212> TYPE: DNA
<213> ORGANISM: Artificial Sequence
<220> FEATURE:
<223> OTHER INFORMATION: DNA sequence based on Chlamydomonas reinhardtii
      HSP70A core promoter

<400> SEQUENCE: 54
cgcgcggcgt ccagaaggcg ccatacggcc cgctggcggc acccatccgg tataaaagcc     60
cgcgaccccg aacggtgacc tccactttca gcgacaaacg agcacttata catacgcgac    120
tattctgccg ctatacataa ccactcaact cgcttaagag ttaattaaaa tg            172

<210> SEQ ID NO 55
<211> LENGTH: 154
<212> TYPE: DNA
<213> ORGANISM: Artificial Sequence
<220> FEATURE:
<223> OTHER INFORMATION: DNA sequence based on Chlamydomonas reinhardtii
      VIP1 core promoter

<400> SEQUENCE: 55
cagctgcggg caggccggct gcatggcttg cttctggaga gggccaattg taattaccgc     60
tttcctgcct ttccaagagc cccctacaac ctacgcactt taaaatcaca tacagcctgt    120
ggcccaactt ccttgttagt ccttaattaa aatg                                154

<210> SEQ ID NO 56
<211> LENGTH: 230
<212> TYPE: DNA
<213> ORGANISM: Artificial Sequence
<220> FEATURE:
<223> OTHER INFORMATION: DNA sequence based on Chlamydomonas reinhardtii
      NPC1 core promoter
```

<400> SEQUENCE: 56

```
cctggtaaat attctgcgcc gctttcgtaa caggtgcagg cgcaggtagc tatacaaata    60
tggtcgcggc tgcaaatgcg gggggaggag gagtacttgc atgggtcgcc cgcgatcggc   120
actcccgctc ggtccccgac tgaacacccg cgcgagcccc gtggttcccc cctttcaac    180 attagccaac tcgaccccag tcgacttttc tcgtcgtttt aattaaaatg              230
```

<210> SEQ ID NO 57
<211> LENGTH: 198
<212> TYPE: DNA
<213> ORGANISM: Artificial Sequence
<220> FEATURE:
<223> OTHER INFORMATION: DNA sequence based on Chlamydomonas reinhardtii AAA1 core promoter

<400> SEQUENCE: 57

```
tcgccattgg gggccgcatg gggccctgga gcaccgaaag tgcagagctc tatagagcgc    60
cactcgttct tcttgcctct tcactagccc gcccacaata attgggttgc agtcaagtga   120
gtgcgtagct tcacagcagg gtctataggg ccccgacact tgcaccaaac ctgccgatca   180
caagcattaa ttaaaatg                                                 198
```

<210> SEQ ID NO 58
<211> LENGTH: 164
<212> TYPE: DNA
<213> ORGANISM: Artificial Sequence
<220> FEATURE:
<223> OTHER INFORMATION: DNA sequence based on Mus musculus Eef2 core promoter

<400> SEQUENCE: 58

```
ccggacgagc acccggcgcc gtcacgtgac gcacccaacc ggcgtcgacc tataaaggc    60 cgggcgttga cgtcagcggt ctcttccgcc gcagccgccg ccatcgtcgg cgcgcttccc   120
tgttcacctc tgactctgag aatccgtcgc cattaattaa aatg                    164
```

<210> SEQ ID NO 59
<211> LENGTH: 196
<212> TYPE: DNA
<213> ORGANISM: Artificial Sequence
<220> FEATURE:
<223> OTHER INFORMATION: DNA sequence based on Mus musculus Col1a1 core promoter

<400> SEQUENCE: 59

```
tccccctctc cgagaggcag ggttcctccc agctctccat caagatggta taaaggggc    60 ccaggccagt cgtcggagca gacgggagtt tctcctcggg acggagcagg aggcacgcgg   120
agtgaggcca cgcatgagcc gaagctaacc ccccaccccca gccgcaaaga gtctacatgt   180
ctagttaatt aaaatg                                                   196
```

<210> SEQ ID NO 60
<211> LENGTH: 137
<212> TYPE: DNA
<213> ORGANISM: Artificial Sequence
<220> FEATURE:
<223> OTHER INFORMATION: DNA sequence based on Mus musculus Rpl4 core promoter

<400> SEQUENCE: 60
ctctaatttg attttgataa ggggcaggat gcggaagacg agtggaagga tatatagagt    60
acaagtgaca agtctttcct tttcctgtgg gagcagccgg gtagagagga gcgtggcctt   120
ctcctttaat taaaatg                                                  137

<210> SEQ ID NO 61
<211> LENGTH: 200
<212> TYPE: DNA
<213> ORGANISM: Artificial Sequence
<220> FEATURE:
<223> OTHER INFORMATION: DNA sequence based on Mus musculus Fabp9 core
      promoter

<400> SEQUENCE: 61
tagagaggct ccctgaatta aactttgcag gttagtttct gttggtggta tataaaatga    60
gtcaaccgcc ggtgcctgga atctcagatt cctggcagcc cattggttgc ttcaggaatg   120
ccacgtgaca aagatgttct ttaaaagaag gggctggcgg cacagcgatg cccacacttc   180
atggtttttt aattaaaatg                                               200

<210> SEQ ID NO 62
<211> LENGTH: 206
<212> TYPE: DNA
<213> ORGANISM: Artificial Sequence
<220> FEATURE:
<223> OTHER INFORMATION: DNA sequence based on Mus musculus Vim core
      promoter

<400> SEQUENCE: 62
gctcggcggc taggatggca gtgggagggg accctctttc ctaacagtgt tataaaagca    60
gcgcccttgg cgttgtccag tcctctgcca ctcttgctcc gggaccccag agaccccagc   120
gctcctacga ttcacagcca ccgcgccctc attcccttgt tgcagttttt ccagccgcag   180
caagccagcc caccttaatt aaaatg                                        206

<210> SEQ ID NO 63
<211> LENGTH: 172
<212> TYPE: DNA
<213> ORGANISM: Artificial Sequence
<220> FEATURE:
<223> OTHER INFORMATION: DNA sequence based on Mus musculus Rplp1 core
      promoter

<400> SEQUENCE: 63
gtcgggcatc gattggtcgg cgcggtccca taagaagctg cgcgcaggcg tatatgatct    60
tttcctcagc tgccgccaag gtgctcggtc cttccgagga agctaaggcc gcgttggggt   120
gaggccctca cttcatccgg cgactagcac cgtgccggca ttaattaaaa tg           172

<210> SEQ ID NO 64
<211> LENGTH: 187
<212> TYPE: DNA
<213> ORGANISM: Artificial Sequence
<220> FEATURE:
<223> OTHER INFORMATION: DNA sequence based on Mus musculus Atp5b core
      promoter

<400> SEQUENCE: 64
attggcacca gtttagacca atagctgata agctccgagt ttttttaccc tatagaagcg    60
ttagtggtga tgacgaacag caaaatcacc caattactgt gcctacggcg gaggttgccc   120

```
cgccccagct gcaggaccgg cggagaggac cgcttcggcg ctcagtctcc acccgttaat    180
taaaatg                                                              187

<210> SEQ ID NO 65
<211> LENGTH: 178
<212> TYPE: DNA
<213> ORGANISM: Artificial Sequence
<220> FEATURE:
<223> OTHER INFORMATION: DNA sequence based on Mus musculus Ppt1 core
      promoter

<400> SEQUENCE: 65
tgtaaaatga gagcagtgca taagatcaat taaaagatgg aaagccctta tatagtagag    60
tctggtgggt gttaagcaat gaataaacgt ctctgtcagg atgcagagcc ggcaggggg    120 cgtggccacc ggaattactt tggtccacag tccccgcggt catgtgttaa ttaaaatg    178

<210> SEQ ID NO 66
<211> LENGTH: 232
<212> TYPE: DNA
<213> ORGANISM: Artificial Sequence
<220> FEATURE:
<223> OTHER INFORMATION: DNA sequence based on Mus musculus Lgals1 core
      promoter

<400> SEQUENCE: 66
gactggtcac ctctgctcca aaattgactt tataatccat agactccact tctggtggcc    60
cccatccttg tcctgacatg caattggctg aactcccggg gagggcggg actcaccggg    120 tctgatccag ttaaaaggt cggagcgggc ctggggcccg tctctcgggt ggagtcttct    180
gactgctggt ggagcaggtc tcaggaatct cttcgcttca ttaattaaaa tg          232

<210> SEQ ID NO 67
<211> LENGTH: 231
<212> TYPE: DNA
<213> ORGANISM: Artificial Sequence
<220> FEATURE:
<223> OTHER INFORMATION: DNA sequence based on Mus musculus Fth1 core
      promoter

<400> SEQUENCE: 67
ggccagcgct cgcctgacgc aggatcccgc tataagtgcg gcccgctgtc ccctcctgcg    60
ccagacgttc tcgcccagag tcgccgcggt ttcctgcttc aacagtgctt gaacggaacc    120
cggtgctcga cccctccgac ccccgccggc cgcttcgagc ctgagccctt tgcaacttcg    180
tcgttccgcc gctccagcgt cgccaccgcg cctcgcccct taattaaat g             231

<210> SEQ ID NO 68
<211> LENGTH: 3047
<212> TYPE: DNA
<213> ORGANISM: Artificial Sequence
<220> FEATURE:
<223> OTHER INFORMATION: inter-species DNA sequences

<400> SEQUENCE: 68
gcatttgctc ggctagtcgg aatgaacatt cattccgaga cctaggatgt gacggaatga    60
aggttcattc cggactctag ataagcacgg aatgaacttt cattccgctg aagcttgtca    120
atcggaatga aggttcattc cggctagtcg gaatgaacat tcattccgag acctaggatg    180
tgacggaatg aaggttcatt ccggactcta gataagcacg gaatgaactt tcattccgct    240
gaagcttgtc aatcggaatg aaggttcatt ccggctagtt ctccccggaa actgtggcca    300
```

```
tatgttcaaa gactaggatg gataaatggg gtatataaag caccctgact cccttcctcc    360
aagttctatc taaccagcca tcctacactc tacatatcca caccaatcta ctacaattat    420
taattaaaat ggtgagcaag ggcgaggagg ataacatggc catcatcaag gagttcatgc    480
gcttcaaggt gcacatggag ggctccgtga acggccacga gttcgagatc gagggcgagg    540
gcgagggccg cccctacgag ggcacccaga ccgccaagct gaaggtgacc aagggtggcc    600
ccctgccctt cgcctgggac atcctgtccc ctcagttcat gtacggctcc aaggcctacg    660
tgaagcaccc cgccgacatc cccgactact tgaagctgtc cttccccgag ggcttcaagt    720
gggagcgcgt gatgaacttc gaggacggcg gcgtggtgac cgtgacccag gactcctccc    780
tgcaggacgg cgagttcatc tacaaggtga agctgcgcgg caccaacttc ccctccgacg    840
gccccgtaat gcagaagaag accatgggct gggaggcctc ctccgagcgg atgtaccccg    900
aggacggcgc cctgaagggc gagatcaagc agaggctgaa gctgaaggac ggcggccact    960
acgacgctga ggtcaagacc acctacaagg ccaagaagcc cgtgcagctg cccggcgcct   1020
acaacgtcaa catcaagttg gacatcacct cccacaacga ggactacacc atcgtggaac   1080
agtacgaacg cgccgagggc cgccactcca ccggcggcat ggacgagtta tacaagtaat   1140
gaggatccga atttcttatg atttatgatt tttattatta aataagttat aaaaaaaata   1200
agtgtataca aattttaaag tgactcttag gttttaaaac gaaaattctt attcttgagt   1260 aactcttttcc tgtaggtcag gttgctttct caggtatagc atgaggtcgc tcttattgac   1320
cacacctcta ccggccagct tttgttccct ttagtgaggg ttaattgcgc gtcgaggcta   1380
acaacccaaa gtaataagtc tgtagtaatt ggtctcgccc tgaattccaa actataaatc   1440
aaccactttc cctcctcccc cccgccccca cttggtcgat tcttcgtttt ctctctacct   1500
tctttctatt cggttttctt cttcttttat tttccctctc ccatcaatca aattcatatt   1560
tgaaaaaaat taaccattaa ttaacaatgg agtccacacc cacgaaacaa aaagctattt   1620
tttctgcctc gctccttctg ttcgccgaac gcggggtttga cgccactacg atgccgatga   1680
tcgctgaaaa tgctaaggtc ggcgcaggaa cgatttaccg atactttaag aataaggaga   1740
gtctggtcaa cgagctgttc cagcagcacg ttaatgaatt tttgcaatgt atcgagagtg   1800
gcttggcgaa cgaaagggac ggttatcgcg atgggttcca tcatatcttc gagggaatgg   1860
tcacattcac aaagaaccat ccgcgcgcct tgggatttat caagcacat tcccaaggta   1920 cattcctaac cgaagagtca cgccttgcat accaaaaact tgttgagttc gtctgcacct   1980
tctttcgaga gggacagaaa cagggcgtaa ttcgaaactt gcccgagaat gccctgatcg   2040
ccatcctatt cggatcgttt atggaggtct atgagatgat cgaaaacgat tatctctctc   2100
taacggatga gttgcttacg ggggtagagg aatcgctctg ggctgctctc tcccgacaat   2160
cggctagccc tcccaagaag aagcgcaagg tcagcacggc cccccccacg gacgtctccc   2220
tcggcgacga gctccacctg gacggcgagg acgtcgccat ggcccacgcc gacgccctcg   2280
acgacttcga cctcgacatg ctgggcgacg gcgacagccc cggccccggc tttacccccc   2340
acgactccgc cccctacggc gccctggaca tggccgactt cgagtttgag cagatgttca   2400
ccgacgccct gggcattgac gagtacgcg gctgaggccg gccgcgatac ccatcatcaa   2460
cacctgatgt tctggggtcc ctcgtgaggt ttctccaggt gggcaccacc atgcgctcac   2520
ttctacgacg aaacgatcaa tgttgctatg catgagcact cgactatgaa tcgaggcacg   2580
ttaattgaga ggctgggaat aagggttcca tcagaacttc tctgggaatg caaaacaaaa   2640
gggaacaaaa aaactagata gaagtgaatt catgacttcg acaaccaaat catcttgtct   2700
```

| | |
|---|---|
| ccgtctgcat acgtgaagct tgtgacgatt attctcgcga tgccacgaca aaggttgtgc | 2760 |
| gaccgtatct tgtccactgt cgtccagtct gcctattccc cctccagtgc tgccatgtgt | 2820 |
| cgtaccttga ggtaggtagt ctacctaggc cagggagctg ttagtgcccg gctactgggt | 2880 |
| aatttgtagc gctggagcga ttcggtcaca ggcgtcaaga gtgctgtagc aatgtccgac | 2940 |
| gccattgatc ctgatatcaa ataccacctg ggcaggtctg ggtatgtgag gtcttgtcgg | 3000 |
| atgtgtcgag ttcttctcca acgtagtgtt cattcgcgct catgccc | 3047 |

<210> SEQ ID NO 69
<211> LENGTH: 3044
<212> TYPE: DNA
<213> ORGANISM: Artificial Sequence
<220> FEATURE:
<223> OTHER INFORMATION: inter-species DNA sequence

<400> SEQUENCE: 69

| | |
|---|---|
| gcatttgctc ggctagtcgg aatgaacatt cattccgaga cctaggatgt gacggaatga | 60 |
| aggttcattc cggactctag ataagcacgg aatgaacttt cattccgctg aagcttgtca | 120 |
| atcggaatga aggttcattc cggctagtcg gaatgaacat tcattccgag acctaggatg | 180 |
| tgacggaatg aaggttcatt ccggactcta gataagcacg aatgaacttt tcattccgct | 240 |
| gaagcttgtc aatcggaatg aaggttcatt ccggctagtt ctccccggaa actgtggcca | 300 |
| tatgccctgc agtgcctgat caccttatca agtggcaaaa tatcccacta taaaaggctt | 360 |
| gggaacccct cgttctgtct taccttctat catcttacca aatccactcc tcttccttca | 420 |
| tacatcaatc ttaccaatca actacctcta caactccaat acacttaatt aaaatggtga | 480 |
| gcaagggcga ggaggataac atggccatca tcaaggagtt catgcgcttc aaggtgcaca | 540 |
| tggagggctc cgtgaacggc cacgagttcg agatcgaggg cgagggcgag ggccgcccct | 600 |
| acgagggcac ccagaccgcc aagctgaagg tgaccaaggg tggccccctg cccttcgcct | 660 |
| gggacatcct gtcccctcag ttcatgtacg gctccaaggc ctacgtgaag caccccgccg | 720 |
| acatccccga ctacttgaag ctgtccttcc ccgagggctt caagtgggag cgcgtgatga | 780 |
| acttcgagga cggcggcgtg gtgaccgtga cccaggactc ctccctgcag gacggcgagt | 840 |
| tcatctacaa ggtgaagctg cgcggcacca acttcccctc cgacggcccc gtaatgcaga | 900 |
| agaagaccat gggctgggag gcctcctccg agcggatgta ccccgaggac ggcgccctga | 960 |
| agggcgagat caagcagagg ctgaagctga aggacggcgg ccactacgac gctgaggtca | 1020 |
| agaccaccta caaggccaag aagcccgtgc agctgcccgg cgcctacaac gtcaacatca | 1080 |
| agttggacat cacctcccac aacgaggact acaccatcgt ggaacagtac gaacgcgccg | 1140 |
| agggcgccca ctccaccggc ggcatggacg agttatacaa gtaatgagga tccgaatttc | 1200 |
| ttatgattta tgattttat tattaaataa gttataaaaa aaataagtgt atacaaattt | 1260 |
| taaagtgact cttaggtttt aaaacgaaaa ttcttattct tgagtaactc tttcctgtag | 1320 |
| gtcaggttgc tttctcaggt atagcatgag gtcgctctta ttgaccacac ctctaccggc | 1380 |
| cagcttttgt tccctttagt gagggttaat tgcgcgtcga ggctagccgc cccaagagag | 1440 |
| ctgaagatgc tgagtagggt tgtccaggca gcacatatat aagatgcttc gtcccctccc | 1500 |
| atcgagtcct tcttttctct ctctcatcaa tcactctact tcctactcta ccttaaactc | 1560 |
| ttcactactt catacgatta acaatggagt ccacacccac gaaacaaaaa gctattttt | 1620 |
| ctgcctcgct ccttctgttc gccgaacgcg ggtttgacgc cactacgatg ccgatgatcg | 1680 |
| ctgaaaatgc taaggtcggc gcaggaacga tttaccgata cttaagaat aaggagagtc | 1740 |

```
tggtcaacga gctgttccag cagcacgtta atgaattttt gcaatgtatc gagagtggct    1800
tggcgaacga aagggacggt tatcgcgatg ggttccatca tatcttcgag gaatggtca     1860 cattcacaaa gaaccatccg cgcgccttgg gatttatcaa gacacattcc caaggtacat   1920
tcctaaccga agagtcacgc cttgcatacc aaaaacttgt tgagttcgtc tgcaccttct    1980
ttcgagaggg acagaaacag ggcgtaattc gaaacttgcc cgagaatgcc ctgatcgcca   2040
tcctattcgg atcgtttatg gaggtctatg agatgatcga aaacgattat ctctctctaa   2100
cggatgagtt gcttacgggg gtagaggaat cgctctgggc tgctctctcc cgacaatcgg   2160 ctagcccctcc caagaagaag cgcaaggtca gcacggcccc ccccacggac gtctccctcg   2220
gcgacgagct ccacctggac ggcgaggacg tcgccatggc ccacgccgac gccctcgacg   2280
acttcgacct cgacatgctg ggcgacggcg acagccccgg ccccggcttt acccccacg    2340 actccgcccc ctacggcgcc ctggacatgg ccgacttcga gtttgagcag atgttcaccg   2400
acgccctggg cattgacgag tacgcggct gaggccggcc gcgataccca tcatcaacac    2460
ctgatgttct ggggtccctc gtgaggtttc tccaggtggg caccaccatg cgctcacttc   2520
tacgacgaaa cgatcaatgt tgctatgcat gagcactcga ctatgaatcg aggcacgtta   2580
attgagaggc tgggaataag ggttccatca gaacttctct gggaatgcaa aacaaaaggg   2640
aacaaaaaaa ctagatagaa gtgaattcat gacttcgaca accaaatcat cttgtctccg   2700
tctgcatacg tgaagcttgt gacgattatt ctcgcgatgc cacgacaaag gttgtgcgac   2760
cgtatcttgt ccactgtcgt ccagtctgcc tattccccct ccagtgctgc catgtgtcgt   2820
accttgaggt aggtagtcta cctaggccag ggagctgtta gtgcccggct actgggtaat   2880
ttgtagcgct ggagcgattc ggtcacaggc gtcaagagtg ctgtagcaat gtccgacgcc   2940
attgatcctg atatcaaata ccacctgggc aggtctgggt atgtgaggtc ttgtcggatg   3000
tgtcgagttc ttctccaacg tagtgttcat tcgcgctcat gccc                    3044
```

<210> SEQ ID NO 70
<211> LENGTH: 2627
<212> TYPE: DNA
<213> ORGANISM: Artificial Sequence
<220> FEATURE:
<223> OTHER INFORMATION: DNA sequence

<400> SEQUENCE: 70

```
gctagctctc tatcactgat agggagtatt gacaagcttt ctctatcact gataggagtg     60
gcttatctag atctctatca ctgataggga gttcacatcc taggtctcta tcactgatag    120
ggagtactag ctctctatca ctgataggga gtattgacaa gctttctcta tcactgatag    180
gagtggctta tctagatctc tatcactgat agggagttca catcctaggt ctctatcact    240
gatagggagt actagttctc cccggaaact gtggcctttt ctggcacaca tgatctccac    300
gatttcaaca tataaatagc ttttgataat ggcaatatta atcaaattta ttttacttct    360
ttcttgtaac atctctcttg taatccctta ttccttctag ctattttca taaaaaacca     420 agcaactgct tatcaacaca caaacactta attaaaatgt ggtctcatcc acaatttgaa    480
aaatctaaag gtgaagaatt attcactggt gttgtcccaa ttttggttga attagatggt    540
gatgttaatg gtcacaaatt ttctgtctcc ggtgaaggtg aaggtgatgc tacttacggt    600
aaattgacct taaaattgat tgtactact ggtaaattgc agttccatg gccaaccta     660 gtcactactt taggttatgg tttgcaatgt tttgctagat acccagatca tatgaaacaa    720
catgactttt tcaagtctgc catgccagaa ggttatgttc aagaaagaac tatttttttc    780
```

| | |
|---|---|
| aaagatgacg gtaactacaa gaccagagct gaagtcaagt ttgaaggtga taccttagtt | 840 |
| aatagaatcg aattaaaagg tattgatttt aaagaagatg gtaacatttt aggtcacaaa | 900 |
| ttggaataca actataactc tcacaatgtt tacatcactg ctgacaaaca aaagaatggt | 960 |
| atcaaagcta acttcaaaat tagacacaac attgaagatg gtggtgttca attagctgac | 1020 |
| cattatcaac aaaatactcc aattggtgat ggtccagtct tgttaccaga caaccattac | 1080 |
| ttatcctatc aatctgcctt atccaaagat ccaaacgaaa agagagacca catggtcttg | 1140 |
| ttagaatttg ttactgctgc tggtattacc catggtatgg atgaattgta caaggatcc | 1200 |
| taagtcgacg ctaattaaca taaaactcat gattcaacgt ttgtgtattt ttttactttt | 1260 |
| gaaggttata gatgtttagg taaataattg gcatagatat agttttagta taataaattt | 1320 |
| ctgatttggt ttaaaatatc aactattttt tttcacatat gttcttgtaa ttacttttct | 1380 |
| gtcctgtctt ccaggttaaa gattagcttc taatatttta ggtggtttat tatttaattt | 1440 |
| tatgctgatt aatttattta ctttcgtatt cggttttgta cctttagcta tgatcttagc | 1500 |
| taattgaagg ggcctcgagg ctagcagctg aaaaaaaagg ttgaaaccag ttccctgaaa | 1560 |
| ttattcccct acttgactaa taagtatata aagacggtag gtattgattg taattctgta | 1620 |
| aatctatttc ttaaacttct taaattctac ttttatagtt agtctttttt ttagttttaa | 1680 |
| aacaccaaga acttagtttc gaataaacac acataattaa ttaaatctag acaatgagta | 1740 |
| gattagacaa atcaaaagtg ataaattctg cattagaatt gttgaatgaa gtaggcattg | 1800 |
| aaggtttgac tacccgtaag ttagctcaga aactaggtgt tgaacaacct acattatact | 1860 |
| ggcacgttaa aaataaaagg gcattgttgg atgcgcttgc cattgagatg ttggataggc | 1920 |
| atcataccca cttttgccca ttagaaggag agtcttggca ggacttttg aggaataatg | 1980 |
| ccaagtcatt tagatgtgca ttgttgtctc atagagatgg ggccaaggtt catctaggta | 2040 |
| cccgtcctac ggaaaaacaa tatgagacgt tggaaaatca gttagcgttc ttatgccaac | 2100 |
| aaggctttag cttggaaaat gctttatatg ctctatcagc tgtcggtcat tttacattgg | 2160 |
| gatgcgtttt agaagaccag gagcaccagg tggcaaagga agaaagagaa acaccaacaa | 2220 |
| ctgattcaat gccaccccta ctgagacaag ctatcgaatt atttgatcat caaggtgcgg | 2280 |
| aacctgcctt cttgtttggc ctagaattga tcatttgtgg tttagaaaag cagttaaaat | 2340 |
| gtgagagtgg ctcagaattc cctcccaaga agaagcgcaa ggtcagcacg gcccccccca | 2400 |
| cggacgtctc cctcggcgac gagctccacc tggacggcga ggacgtcgcc atggcccacg | 2460 |
| ccgacgccct cgacgacttc gacctcgaca tgctgggcga cggcgacagc cccgccccg | 2520 |
| gctttacccc ccacgactcc gccccctacg gcgccctgga catggccgac ttcgagtttg | 2580 |
| agcagatgtt caccgacgcc ctgggcattg acgagtacgg cggctga | 2627 |

<210> SEQ ID NO 71
<211> LENGTH: 3001
<212> TYPE: DNA
<213> ORGANISM: Artificial Sequence
<220> FEATURE:
<223> OTHER INFORMATION: DNA sequence

<400> SEQUENCE: 71

| | |
|---|---|
| catttgctcg gctagtcgga atgaacattc attccgagac ctaggatgtg acggaatgaa | 60 |
| ggttcattcc ggactctaga taagcacgga atgaactttc attccgctga agcttgtcaa | 120 |
| tcggaatgaa ggttcattcc ggctagtcgg aatgaacatt cattccgaga cctaggatgt | 180 |
| gacggaatga aggttcattc cggactctag ataagcacgg aatgaacttt cattccgctg | 240 |

```
aagcttgtca atcggaatga aggttcattc cggctagttc tccccggaaa ctggaatttg    300
tggttctcgt gaagtcgtga taatagtttg tccaagcgat aaatataaaa tagtattgca    360
cctcaacaag tgttaagcat gcaaatccat ttacgcatac atattaactc cgagtgaaat    420
ataaatatta gagagtagag acagagaaaa agacagagac aaagttaatt aaaatggtaa    480
gcaagggaga agaggataac atggcaatca taaaggaatt tatgcgtttc aaggtccaca    540
tggaaggttc tgtcaatggg cacgagttcg agattgaagg cgaggggag ggtagaccgt    600 atgaagggac ccagactgcc aaattgaagg taacaaaagg cgggccgctt ccattcgctt    660
gggatatcct cagtccgcag ttcatgtatg gctccaaggc ctatgtgaag catcctgcag    720
atatacccga ctatttaaag ctcagtttcc ccgagggctt caaatgggaa agagttatga    780
attttgagga cggaggtgtt gtaaccgtca cgcaggatag cagcttacag gacggcgaat    840
ttatttacaa ggtaaagttg cgtggtacga atttccttc agatggtccg gtcatgcaga    900
agaagactat gggttgggaa gcaagctctg agaggatgta tcccgaagat ggggctctta    960
aaggcgagat aaagcagagg ctgaaactga aggacggcgg gcactacgat gccgaagtca   1020
aaaccaccta taaggctaaa aagcccgtac agcttcccgg tgcttacaac gtgaacatca   1080
aattagacat tacctcccac aatgaagact ataccatcgt ggagcaatac gagagggccg   1140
agggaaggca ctctacagga ggaatggatg aactctacaa aggatcctaa tagctatata   1200
tctttcttac atcattattg taatctgttc tccttctgtg tattcgtttc aatgttgcag   1260
caatgaactt ttggataaaa gtcaaatttg ttgtttcctt aattcgaaag acgattgaga   1320
cttgaaatca taacactaag cttcattgaa tcaagattca atagtattca tcaattcata   1380
atataatagt gtactaaact cgagcttgca tattctgagt taattgaaat acctcactgt   1440
aatacctaga acgaacttac cttacgagca aatcaagcat gtatttactc tcggatgtat   1500
aattcacctt atcaaccttc acaacagtca tcttcactct tgttcatcc ccatacgatt   1560 cctctttgat cttcagcttc atttaaatgc gatcccctct ggcaaattct tatccatttg   1620
ggttttattg ggcttttgaa ataataaagc ccattaagtt agttactagg gttttgttgt   1680
tgtttaaagg aggaataaga gcgtaagcta caaaatcttt ctattcatct ccgccgctcc   1740
tcatcctgta aagctaaaca aataatcaga ggaacgaagg agacagcttc tgcttaatta   1800
aaatggagag tacaccaacc aaacagaaag ctattttag cgcaagcctg ttattatttg   1860
ctgagcgtgg ctttgacgct acgacgatgc ccatgatagc cgaaaatgct aaagttgggg   1920
ctggaaccat ataccgatac ttcaaaaaca aagaaagtct ggtgaatgaa ctgtttcaac   1980
aacacgtaaa cgagttcttg cagtgcatcg agtctggact cgctaacgag cgtgacggct   2040
atagagatgg atttcatcat atatttgagg gcatggtcac cttcacaaaa aaccacccaa   2100
gggctctggg tttcataaaa acgcacagtc aaggcacatt ccttacggag gagagcagat   2160
tagcatatca gaaattagtg gagttcgtat gtactttctt tagagaagga cagaagcaag   2220
gagttattcg aaacctgccg gaaaacgcct taattgccat cctgtttggg tctttcatgg   2280
aagtttacga aatgatagag aatgattacc tctcccttac cgacgaattg ttgactggcg   2340
tcgaagaatc attgtgggca gcattgtcta ggcaatcaga attcccacct aagaagaaaa   2400
ggaaagtatc cgcctccggt tctgggcgtg ccgacgctct ggacgatttc gacctcgata   2460
tgttggggtc agacgcattg gacgactttg atttggacat gttaggtagt gatgctttag   2520
acgatttcga cttggacatg ttaggctccg atgcattgga cgattttgac ttagatatgt   2580
tgattaatag taggtaatga gtcgactctt taatcaaaat gtaatatgaa taaaagttga   2640
```

```
tgtgggctca tctattgagc tcatgtctct cttattacta ctctctagta tggtgtgatg    2700
taatgggtta tgaccctcct ttcccttccc tataaaacta aagaaacttg caagataatt    2760
gaaaagatgg tttcttttta ttatcaatcg catcaaaatg ggattttgta tcaaatgcat    2820
acattatctc ttgcttttat accctaaacc cataccgggt gatgaacaat cttctgttgc    2880
tcattccttt tgatgatcca tcaaattacg tattagaaaa agaaaaaaaa gtatcagacg    2940 ttgaaaccctt ctgctcggag acaaatttta tgagcctcga tccatttaaa tcaagcccgg    3000
g                                                                     3001
```

<210> SEQ ID NO 72
<211> LENGTH: 3088
<212> TYPE: DNA
<213> ORGANISM: Artificial Sequence
<220> FEATURE:
<223> OTHER INFORMATION: DNA sequence

<400> SEQUENCE: 72

```
catttgctcg gctagctctc tatcactgat agggagtatt gacaagcttt ctctatcact      60
gataggagtg gcttatctag atctctatca ctgatagggga gttcacatcc taggtctcta    120
tcactgatag ggagtactag ctctctatca ctgataggga gtattgacaa gctttctcta    180
tcactgatag gagtggctta tctagatctc tatcactgat agggagttca catcctaggt    240
ctctatcact gataggagt actagttctc cccggaaact ggaatttgtg gttctcgtga    300
agtcgtgata atagtttgtc caagcgataa atataaaata gtattgcacc tcaacaagtg    360
ttaagcatgc aaatccattt acgcatacat attaactccg agtgaaatat aaatattaga    420
gagtagagac agagaaaaag acagagacaa agttaattaa aatggtaagc aagggagaag    480
aggataacat ggcaatcata aaggaattta tgcgtttcaa ggtccacatg gaaggttctg    540
tcaatgggca cgagttcgag attgaaggcg aggggagg tagaccgtat gaagggaccc    600
agactgccaa attgaaggta acaaaaggcg ggccgcttcc attcgcttgg gatatcctca    660
gtccgcagtt catgtatggc tccaaggcct atgtgaagca tcctgcagat atacccgact    720
atttaaagct cagtttcccc gagggcttca aatgggaaag agttatgaat tttgaggacg    780
gaggtgttgt aaccgtcacg caggatagca gcttacagga cggcgaattt atttacaagg    840
taaagttgcg tggtacgaat tttccttcag atggtccggt catgcagaag aagactatgg    900
gttgggaagc aagctctgag aggatgtatc ccgaagatgg ggctcttaaa ggcgagataa    960
agcagaggct gaaactgaag gacggcgggc actacgatgc cgaagtcaaa accacctata   1020
aggctaaaaa gcccgtacag cttcccggtg cttacaacgt gaacatcaaa ttagacatta   1080
cctcccacaa tgaagactat accatcgtgg agcaatacga gagggccgag gaaggcact   1140 ctacaggagg aatggatgaa ctctacaaag gatcctaata gctatatatc tttcttacat   1200
cattattgta atctgttctc cttctgtgta ttcgtttcaa tgttgcagca atgaactttt   1260
ggataaaagt caaatttgtt gttcccttaa ttcgaaagac gattgagact tgaaatcata   1320
acactaagct tcattgaatc aagattcaat agtattcatc aattcataat ataatagtgt   1380
actaaactcg agcttgcata ttctgagtta attgaaatac ctcactgtaa tacctagaac   1440
gaacttacct tacgagcaaa tcaagcatgt atttactctc ggatgtataa ttcacccttat  1500 caaccttcac aacagtcatc ttcactcttt gttcatcccc atacgattcc tctttgatct   1560
tcagcttcat ttaaatgcga tccctctgg caaattctta tccatttggg ttttattggg   1620
cttttgaaat aataaagccc attaagttag ttactagggt tttgttgttg tttaaaggag   1680
```

```
gaataagagc gtaagctaca aaatctttct attcatctcc gccgctcctc atcctgtaaa    1740
gctaaacaaa taatcagagg aacgaaggag acagcttctg cttaattaaa atgtcaagat    1800
tagacaaaag caaagtaatc aatagtgcat tagaactttt aaacgaggtc ggaatagagg    1860
gattaactac acgtaaactc gcccagaagc tcggagttga acaacctacg ctgtattggc    1920
atgttaaaaa taaacgagca ttattggatg ctctggctat tgagatgctc gataggcacc    1980
atacccactt ttgccctctg gaggggaat cttggcaaga cttcttgcgt aacaacgcca    2040
agtcattcag atgtgccttg ctgagtcacc gtgacggcgc taaagtccat ctcggaaccc    2100
gaccgaccga gaagcaatac gagaccttag aaaaccaatt agcctttctt tgccagcaag    2160
ggttttcatt agagaatgct ctctacgccc tttccgctgt tgggcatttc accctgggtt    2220
gcgtcttgga ggatcaggaa catcaagtag caaaggagga acgagagaca cctactacgg    2280
attctatgcc gcccctcctc aggcaggcaa ttgaactgtt cgatcatcag ggagctgaac    2340
ctgcttttct gtttggcctg gaattgataa tatgcggact ggagaaacag ttaaagtgcg    2400
agagcggtag cgaattccca cctaaaaaaa agagaaaagt ttccactgcc cccccaacgg    2460
acgtctctct gggcgacgag ctgcacctcg atggtgagga cgtggctatg gctcatgctg    2520
atgccttaga cgacttcgac ttagatatgc tgggagatgg cgactcaccg ggaccagggt    2580
ttacacctca tgattctgct ccttacggag ctttagatat ggccgatttt gaatttgagc    2640
aaatgttcac tgacgccctt ggaatagacg aatacggggg ctaatgagtc gactcttta    2700 tcaaaatgta atatgaataa agttgatgt gggctcatct attgagctca tgtctctctt    2760
attactactc tctagtatgg tgtgatgtaa tgggttatga cccttctttc ccttccctat    2820
aaaactaaag aaacttgcaa gataattgaa aagatggttt cttttttatta tcaatcgcat    2880 caaaatggga ttttgtatca aatgcataca ttatctcttg cttttatacc ctaaacccat    2940
accgggtgat gaacaatctt ctgttgctca ttccttttga tgatccatca aattacgtat    3000
tagaaaaaga aaaaaaagta tcagacgttg aaaccttctg ctcggagaca aattttatga    3060
gcctcgatcc atttaaatca agcccggg                                       3088
```

<210> SEQ ID NO 73
<211> LENGTH: 2992
<212> TYPE: DNA
<213> ORGANISM: Artificial Sequence
<220> FEATURE:
<223> OTHER INFORMATION: DNA sequence

<400> SEQUENCE: 73

```
gcatttgctc ggctagtcgg aatgaacatt cattccgaga cctaggatgt gacggaatga     60
aggttcattc cggactctag ataagcacgg aatgaacttt cattccgctg aagcttgtca    120
atcggaatga aggttcattc cggctagtcg gaatgaacat tcattccgag acctaggatg    180
tgacggaatg aaggttcatt ccggactcta gataagcacg gaatgaactt tcattccgct    240
gaagcttgtc aatcggaatg aaggttcatt ccggctagtt ctccccggaa actgcgacga    300
agggatgtct ccgcaaggca agtatataac ggctagcaac gtatgcctta gcatagtaga    360
gcaattagtt gtctatgtgc ctcggtgcaa gcgcacacgc cggaataat gcggcatggg    420 ggcttctgtt ggccccatgc gagcccccag gaagaaaagt cgcgcggcgc ccgtattctg    480
ccctcttgct gtgccaacct cctagtcgct tcttcgcact ttttaattaa aatggtctcc    540
aagggtgagg aggacaacat ggctatcatc aaggagttca tgcgcttcaa ggtccatatg    600
gaggggagcg tgaacggcca cgagtttgag atcgaggggg agggcgaggg ccgcccctac    660
```

```
gagggcaccc agacggcgaa gctcaaggtg accaagggtg gcccctgcc ctttgcgtgg      720
gacatcctgt cccccagtt tatgtacggg agcaaggctt acgtcaagca ccctgcggac      780
atccctgact acctgaagct ctccttcccc gagggtttta agtgggagcg ggtcatgaac     840
tttgaggacg gtggtgtggt caccgtgacc caggacagca gcctccagga tggtgagttt     900
atttacaagg tgaagctccg gggcacgaac ttccccagcg atgggccggt gatgcagaag     960
aagacgatgg gctgggaggc ctcgtcggag cgcatgtacc ctgaggacgg cgccctgaag    1020
ggtgagatca agcagcgcct gaagctgaag gatgggggc attacgacgc tgaggtcaag     1080
acgacgtaca aggccaagaa gccggtgcag ctgcccggtg cctacaacgt gaacatcaag    1140
ctggacatca ccagccacaa cgaggattac accattgtcg agcagtacga gcgggctgag    1200
ggccgccact ccaccggggg tatggacgag ctgtacaagg atatctaaat ggaggcgctc    1260
gttgatctga gccttgcccc ctgacgaacg gcggtggatg gaagatactg ctctcaagtg    1320
ctgaagcggt agcttagctc cccgtttcgt gctgatcagt cttttcaac acgtaaaaag      1380
cggaggagtt ttgcaatttt gttggttgta acgatcctcc gttgattttg gcctctttct    1440
ccatgggcgg gctgggcgta tttgaagcgc ttttggaaaa gttgctgcgg ggttcatcag    1500
ctgaagggga ctcggttcgc agatcagtta cacactaaag aacggcgggt agcaacacca    1560
gcaaacgtga cgaaacggaa ccgtgcagca tttaaatggc ccgaacttgc tctcggtgtc    1620
atattgcacc atcccatctt gtataaccga tataacatag cttcgagtgt gccgataaat    1680
tattgtgagg gcgtcggggg gcgagctgag ggaaatggag ggggcactca tctcggccgc    1740
ccctcccatc gcgacctcgg cgctcaagcg ggggtcccgc actcgcttcg gtctcttttg    1800
gtcagcagcc gtttgttgac taccgttaat taaaatggag agcaccccta ccaagcagaa    1860
ggcgatcttt tcggcttcgc tgctgctgtt tgccgagcgc gggtttgatg ctaccaccat    1920
gcccatgatc gctgagaacg ctaaggtcgg ggcgggcacg atttaccggt acttcaagaa    1980
caaggagtcg ctcgtcaacg agctgtttca gcagcatgtg aacgagttcc tgcagtgcat    2040
tgagtccggt ctcgccaacg agcgggatgg ctaccgcgat ggtttccatc acatcttcga    2100
gggcatggtc acgtttacga agaaccatcc tcgcgctctc ggttttatca agacccattc    2160
ccaggggacc tttctcacgg aggagtcgcg gctggcttac cagaagctgg tcgagtttgt    2220
ctgcaccttt ttccgggagg gtcagaagca gggtgtgatt cggaacctgc cggagaacgc    2280
tctcattgct atcctctttg gctcgtttat ggaggtctac gagatgattg agaacgatta    2340
cctgtccctg acggacgagc tgctcacggg cgtcgaggag agcctctggg ctgctctgtc    2400
gcggcagtcg gagctccccc ctaagaagaa gcgcaaggtg tcggcctccg ggagcggccg    2460
ggctgatgct ctggatgact cgacctgga catgctgggt agcgacgctc tcgacgattt     2520
tgacctggac atgctcggct cggatgccct ggacgatttc gatctggata tgctgggtag    2580
cgacgcgctc gacgactttg atctggacat gctcattaac agccgctaaa cgcgtggccc    2640
caccgttgcg tgtgcgcccg cggtgcgctg cgcggtcggc agcttgggtg tggcatccgg    2700
tgcggcttgt cccgccggca tgtagctctt atgtaacggg ctgtctgtac tcacttgtgt    2760
ccaaccgcct ctctggatgt ctggttcatg accaacagct aagcaaagaa gcagctggga    2820
caccagggga cgctgacaat ggagtgggca gccgacgcag cagagggggg actgcgagtt    2880
atacggtatt aggctgggct ggcaggtccg gtagacggta atgcgacaca caagccgtgg    2940
gagaaggttg cgtcaggaag tccaagcagg ttctgtattt aaatgcggcc gc            2992
```

<210> SEQ ID NO 74
<211> LENGTH: 3076
<212> TYPE: DNA
<213> ORGANISM: Artificial Sequence
<220> FEATURE:
<223> OTHER INFORMATION: DNA sequence

<400> SEQUENCE: 74

```
ttgctcggct agctctctat cactgatagg gagtattgac aagctttctc tatcactgat      60
aggagtggct tatctagatc tctatcactg atagggagtt cacatcctag gtctctatca     120
ctgataggga gtactagctc tctatcactg atagggagta ttgacaagct tctctatca     180
ctgataggag tggcttatct agatctctat cactgatagg gagttcacat cctaggtctc     240
tatcactgat agggagtact agttctcccc ggaaactgcg acgaagggat gtctccgcaa     300
ggcaagtata taacggctag caacgtatgc cttagcatag tagagcaatt agttgtctat     360
gtgcctcggt gcaagcgcac acgccgggaa taatgcggca tggggcttc tgttggcccc     420
atgcgagccc ccaggaagaa aagtcgcgcg gcgcccgtat tctgccctct tgctgtgcca     480
acctcctagt cgcttcttcg cactttttaa ttaaaatggt ctccaagggt gaggaggaca     540
acatggctat catcaaggag ttcatgcgct tcaaggtcca tatggagggg agcgtgaacg     600
gccacgagtt tgagatcgag ggggagggcg agggccgccc ctacgagggc acccagacgg     660
cgaagctcaa ggtgaccaag ggtggccccc tgccctttgc gtgggacatc ctgtcccccc     720
agtttatgta cgggagcaag gcttacgtca agcaccctgc ggacatccct gactacctga     780
agctctcctt ccccgagggt tttaagtggg agcgggtcat gaactttgag gacggtggtg     840
tggtcaccgt gacccaggac agcagcctcc aggatggtga gttatttac aaggtgaagc     900
tccggggcac gaacttcccc agcgatgggc cggtgatgca aagaagacg atgggctggg     960
aggcctcgtc ggagcgcatg taccctgagg acggcgccct gaagggtgag atcaagcagc    1020
gcctgaagct gaaggatggg gggcattacg acgctgaggt caagacgacg tacaaggcca    1080
agaagccggt gcagctgccc ggtgcctaca acgtgaacat caagctggac atcaccagcc    1140
acaacgagga ttacaccatt gtcgagcagt acgagcgggc tgagggccgc cactccaccg    1200
ggggtatgga cgagctgtac aaggatatct aaatggaggc gctcgttgat ctgagccttg    1260
cccccctgacg aacggcggtg gatggaagat actgctctca agtgctgaag cggtagctta    1320
gctccccgtt tcgtgctgat cagtcttttt caacacgtaa aaagcggagg agttttgcaa    1380
ttttgttggt tgtaacgatc ctccgttgat tttggcctct ttctccatgg gcgggctggg    1440
cgtatttgaa gcgcttttgg aaaagttgct gcggggttca tcagctgaag gggactcggt    1500
tcgcagatca gttacacact aaagaacggc gggtagcaac accagcaaac gtgacgaaac    1560
ggaaccgtgc agcatttaaa tggcccgaac ttgctctcgg tgtcatattg caccatccca    1620
tcttgtataa ccgatataac atagcttcga gtgtgccgat aaattattgt gagggcgtcg    1680
ggggcgagc tgagggaaat ggaggggca ctcatctcgg ccgcccctcc catcgcgacc    1740
tcggcgctca gcggggtc ccgcactcgc ttcggtctct tttggtcagc agccgtttgt    1800
tgactaccgt taattaaaat gagccggctg ataagtccaa aggtcatcaa ctccgcgctc    1860
gagctgctca acgaggtcgg gatcgagggc ctgacgaccc ggaagctggc gcagaagctg    1920
ggggtggagc agccgaccct gtactggcac gtcaagaaca gcgggccct gctcgatgcc    1980
ctcgctatcg agatgctcga tcggcatcat acgcattttt gccctctcga gggggagtcc    2040
tggcaggact ttctgcggaa caacgccaag tcgttccggt gcgccctgct gtcccatcgg    2100
```

```
gatggtgcta aggtccatct cgggacgcgg cctaccgaga agcagtacga gaccctggag    2160
aaccagctcg cttttctgtg ccagcagggg ttctccctgg agaacgctct ctacgccctc    2220
tccgctgtgg gtcattttac cctcggttgc gtcctggagg atcaggagca tcaggtcgcc    2280
aaggaggagc gggagacccc taccacggac tcgatgcccc ctctcctccg gcaggctatt    2340
gagctgtttg accatcaggg cgcggagcct gcctttctct ttgggctcga gctgattatt    2400
tgcggcctcg agaagcagct caagtgcgag tccggttcgg agctccctcc taagaagaag    2460
cgcaaggtga gcaccgcccc ccccacggat gtgtccctgg gtgatgagct gcatctcgac    2520
ggcgaggatg tcgccatggc tcatgccgat gccctggatg atttcgatct cgatatgctg    2580
ggtgatggtg actcccccgg tccgggtttt acgcctcacg atagcgcccc ttacggcgct    2640
ctggacatgg ccgattttga gtttgagcag atgttcacgg acgcgctcgg catcgacgag    2700
tacggcggtt aaacgcgtgg ccccaccgtt gcgtgtgcgc ccgcggtgcg ctgcgcggtc    2760
ggcagcttgg gtgtggcatc cggtgcggct tgtcccgccg gcatgtagct cttatgtaac    2820
gggctgtctg tactcacttg tgtccaaccg cctctctgga tgtctggttc atgaccaaca    2880
gctaagcaaa gaagcagctg gacaccagg ggacgctgac aatggagtgg gcagccgacg    2940
cagcagaggg gggactgcga gttatacggt attaggctgg gctggcaggt ccggtagacg    3000
gtaatgcgac acacaagccg tgggagaagg ttgcgtcagg aagtccaagc aggttctgta    3060
tttaaatgcg gccgcg                                                    3076
```

<210> SEQ ID NO 75
<211> LENGTH: 2980
<212> TYPE: DNA
<213> ORGANISM: Artificial Sequence
<220> FEATURE:
<223> OTHER INFORMATION: DNA sequence

<400> SEQUENCE: 75

```
tttgctcggc tagtcggaat gaacattcat tccgagacct aggatgtgac ggaatgaagg      60
ttcattccgg actctagata agcacggaat gaactttcat tccgctgaag cttgtcaatc     120
ggaatgaagg ttcattccgg ctagtcggaa tgaacattca ttccgagacc taggatgtga     180
cggaatgaag gttcattccg gactctagat aagcacggaa tgaactttca ttccgctgaa     240
gcttgtcaat cggaatgaag gttcattccg gctagttctc cccggaaact gccggacgag     300
cacccggcgc cgtcacgtga cgcacccaac cggcgttgac ctataaaagg ccgggcgttg     360
acgtcagcgc tctcttccgc cgcagccgcc gccatcgtcg gcgcgcttcc ctgttcacct     420
ctgactctga gaatccgtcg ccatccgcca ccatgggatc cgtgtctaaa ggggaggaag     480
acaacatggc tattattaag gagttcatga ggtttaaggt gcatatggag gggagcgtaa     540
acggtcacga atttgagatt gaaggcgaag ggaaggaag accctatgaa ggtactcaaa     600
ctgcaaaact caaggtcacc aaaggtggac cactgccctt cgcttgggat atacttagcc     660
cacagtttat gtacgggtct aaagcctatg taaagcatcc agcagatata ccagactacc     720
ttaaactgag ctttcctgaa ggttttaagt gggagcgggt gatgaatttc gaagacggtg     780
gcgtggttac cgttacccag gacagcagtt tgcaagatgg agaatttatc tacaaggtaa     840
aactgcgggg gaccaatttc ccaagtgacg gacccgtaat gcagaaaaag actatggggt     900 ggaggcttc ttcagaacgc atgtaccccg aagacggtgc tctgaaaggc gaaataaagc     960
aacgattgaa gctcaaagat gggggccatt acgacgccga ggtaaaaact acctataaag    1020
ccaaaaagcc tgttcagctg cctggtgctt ataatgtgaa tataaagttg gacataacct    1080
```

| | |
|---|---|
| cacataacga agattacact attgttgaac agtacgagag agcagagggg cggcattcta | 1140 |
| caggagggat ggacgaactg tacaaataag atatcttccc caaagccacg tgactttact | 1200 |
| ggtcactgag gcagtgcatg catgtcaggc tgccttcatc ttttctataa gttgcaccaa | 1260 |
| aacatctgct taagttcttt aatttgtacc atttcttcaa ataaagaatt ttggtaccca | 1320 |
| gcttcttttc tttgtgattg aggataagca ttccagcttc cagttgcttc accgccagtt | 1380 |
| atactaatca cactgaaaca cctaaaagaa tattcacgtt tattaaactc cttagtttgg | 1440 |
| gaaagatcgt aaaatacagg tgttttcagg caggactatt aagtactctt ggttctgagt | 1500 |
| tacatgctag actgtcgtgg gaacacactc ctgggtgtcg ctgcttgtgt gcctttgact | 1560 |
| gggtcagtga tttaaatatt ggcaccagtt tagaccaata gctgataagc tccgagtttt | 1620 |
| tttaccctat agaagcgtta gtggtgatga cgaacagcaa aatcacccaa ttactgtgcc | 1680 |
| tacggcggag gttgccccgc cccagctgca ggaccggcgg agaggaccgc ttcggcgctc | 1740 |
| agtctccacc cggattccgc catggaaagc acaccaacaa agcaaaaagc aatattttca | 1800 |
| gcctcacttc ttttgtttgc cgagaggggt ttcgacgcta caacaatgcc catgatagcc | 1860 |
| gaaaatgcca agtaggagc cgggacaata tacaggtatt ttaaaaacaa ggaaagtctg | 1920 |
| gtcaatgaac ttttccagca gcacgtaaat gagtttcttc aatgtattga atctggcctg | 1980 |
| gctaacgaac gcgacggtta tcgtgatggc tttcatcaca tatttgaggg aatggtcact | 2040 |
| ttcaccaaaa atcaccctag ggccttgggc tttatcaaaa cacattctca gggtacattc | 2100 |
| ctcaccgagg aatctcgact cgcctatcaa aagctcgttg agtttgtctg tactttcttt | 2160 |
| agggagggac aaaagcaagg cgtaatccga aacctcccag agaacgcctt gatcgctatt | 2220 |
| ctcttcggat cttttatgga ggtctatgag atgatcgaaa atgactatct tagtctgaca | 2280 |
| gatgagcttc tgacaggtgt tgaagaatca ttgtgggctg ctttgtctag acagagtgaa | 2340 |
| ttccctccca agaagaaacg aaaggtaagc gcctctggtt caggtcgtgc tgacgctctg | 2400 |
| gatgattttg atctcgacat gcttggttct gatgctcttg acgacttcga ccttgatatg | 2460 |
| ctgggcagtg acgcattgga cgactttgat ttggacatgt tgggaagcga tgccttggac | 2520 |
| gactttgacc ttgatatgct gataaatagt cgctaatagc tcgagcgcct cctcctccca | 2580 |
| tagccgatgg ccacagtcaa ttcaccaccc cagggtcctc agctaggagg aggacagagt | 2640 |
| gtggaaagta gacagtttcc acttcctttt ccctacatct ttcagtatga gggtaccata | 2700 |
| tcctgctcca cccaggtcct gtggataaca ataaaaaagg aagtgtgtgt gcctttgtat | 2760 |
| gtgttcccct cacgtctttg acaatggggt tggggaggtc tggggtcaga gagaattgcg | 2820 |
| ttgtgggatt ttgagttaac tgcttttggc tttagagatc gacagtctaa gaggtaaaat | 2880 |
| tagatgtgaa ttagttggga agctgccaag tgtcccagag ctttggacac ccactctagg | 2940 |
| gacacattgt ccccttattt aaatagggcc cgtttaaacc | 2980 |

<210> SEQ ID NO 76
<211> LENGTH: 16
<212> TYPE: DNA
<213> ORGANISM: Artificial Sequence
<220> FEATURE:
<223> OTHER INFORMATION: DNA sequence identical or derived from
    naturally occurring LexA binding site

<400> SEQUENCE: 76

| | |
|---|---|
| ctgtatataa acacag | 16 |

```
<210> SEQ ID NO 77
<211> LENGTH: 16
<212> TYPE: DNA
<213> ORGANISM: Artificial Sequence
<220> FEATURE:
<223> OTHER INFORMATION: DNA sequence identical or derived from
      naturally occurring LexA binding site

<400> SEQUENCE: 77
ctgtatatat acccag                                                 16

<210> SEQ ID NO 78
<211> LENGTH: 16
<212> TYPE: DNA
<213> ORGANISM: Artificial Sequence
<220> FEATURE:
<223> OTHER INFORMATION: DNA sequence identical or derived from
      naturally occurring LexA binding site

<400> SEQUENCE: 78
ctgtatataa aaccag                                                 16

<210> SEQ ID NO 79
<211> LENGTH: 16
<212> TYPE: DNA
<213> ORGANISM: Artificial Sequence
<220> FEATURE:
<223> OTHER INFORMATION: DNA sequence identical or derived from
      naturally occurring LexA binding site

<400> SEQUENCE: 79
gtggttatat atacag                                                 16

<210> SEQ ID NO 80
<211> LENGTH: 30
<212> TYPE: DNA
<213> ORGANISM: Artificial Sequence
<220> FEATURE:
<223> OTHER INFORMATION: DNA sequence identical or derived from
      naturally occurring SrpR binding site

<400> SEQUENCE: 80
atatacatac atgcttgttt gtttgtaaac                                  30

<210> SEQ ID NO 81
<211> LENGTH: 30
<212> TYPE: DNA
<213> ORGANISM: Artificial Sequence
<220> FEATURE:
<223> OTHER INFORMATION: DNA sequence identical or derived from
      naturally occurring SrpR binding site

<400> SEQUENCE: 81
atttacatac attcttgttt gtttgtaaac                                  30

<210> SEQ ID NO 82
<211> LENGTH: 30
<212> TYPE: DNA
<213> ORGANISM: Artificial Sequence
<220> FEATURE:
<223> OTHER INFORMATION: DNA sequence identical or derived from
      naturally occurring PhlF binding site

<400> SEQUENCE: 82
atgatacgaa acgtaccgta tcgttaaggt                                  30
```

```
<210> SEQ ID NO 83
<211> LENGTH: 30
<212> TYPE: DNA
<213> ORGANISM: Artificial Sequence
<220> FEATURE:
<223> OTHER INFORMATION: DNA sequence identical or derived from
      naturally occurring PhlF binding site

<400> SEQUENCE: 83
atgatacgga acgttacgta tcgttaagct                                30

<210> SEQ ID NO 84
<211> LENGTH: 30
<212> TYPE: DNA
<213> ORGANISM: Artificial Sequence
<220> FEATURE:
<223> OTHER INFORMATION: DNA sequence identical or derived from
      naturally occurring PhlF binding site

<400> SEQUENCE: 84
atgatacgga agctaccgta tcgtaaaggt                                30

<210> SEQ ID NO 85
<211> LENGTH: 30
<212> TYPE: DNA
<213> ORGANISM: Artificial Sequence
<220> FEATURE:
<223> OTHER INFORMATION: DNA sequence identical or derived from
      naturally occurring PhlF binding site

<400> SEQUENCE: 85
atgatacgta acgtaccgta tcgtaaaggt                                30

<210> SEQ ID NO 86
<211> LENGTH: 21
<212> TYPE: DNA
<213> ORGANISM: Artificial Sequence
<220> FEATURE:
<223> OTHER INFORMATION: DNA sequence identical or derived from
      naturally occurring TetR binding site

<400> SEQUENCE: 86
actccctatc agtgatagag a                                         21

<210> SEQ ID NO 87
<211> LENGTH: 20
<212> TYPE: DNA
<213> ORGANISM: Artificial Sequence
<220> FEATURE:
<223> OTHER INFORMATION: DNA sequence identical or derived from
      naturally occurring BM3R1 binding site

<400> SEQUENCE: 87
cggaatgaag gttcattccg                                           20

<210> SEQ ID NO 88
<211> LENGTH: 20
<212> TYPE: DNA
<213> ORGANISM: Artificial Sequence
<220> FEATURE:
<223> OTHER INFORMATION: DNA sequence identical or derived from
      naturally occurring BM3R1 binding site

<400> SEQUENCE: 88
cggaatgaac tttcattccg                                           20
```

```
<210> SEQ ID NO 89
<211> LENGTH: 20
<212> TYPE: DNA
<213> ORGANISM: Artificial Sequence
<220> FEATURE:
<223> OTHER INFORMATION: DNA sequence identical or derived from
      naturally occurring BM3R1 binding site

<400> SEQUENCE: 89
cggaatgaac attcattccg                                                  20

<210> SEQ ID NO 90
<211> LENGTH: 20
<212> TYPE: DNA
<213> ORGANISM: Artificial Sequence
<220> FEATURE:
<223> OTHER INFORMATION: DNA sequence identical or derived from
      naturally occurring BM3R1 binding site

<400> SEQUENCE: 90
cggaatgaac gttcattccg                                                  20

<210> SEQ ID NO 91
<211> LENGTH: 20
<212> TYPE: DNA
<213> ORGANISM: Artificial Sequence
<220> FEATURE:
<223> OTHER INFORMATION: DNA sequence identical or derived from
      naturally occurring TarA binding site

<400> SEQUENCE: 91
aacataccgt gtggtatgtt                                                  20

<210> SEQ ID NO 92
<211> LENGTH: 20
<212> TYPE: DNA
<213> ORGANISM: Artificial Sequence
<220> FEATURE:
<223> OTHER INFORMATION: DNA sequence identical or derived from
      naturally occurring TarA binding site

<400> SEQUENCE: 92
aacataccga gtggtatgtt                                                  20

<210> SEQ ID NO 93
<211> LENGTH: 20
<212> TYPE: DNA
<213> ORGANISM: Artificial Sequence
<220> FEATURE:
<223> OTHER INFORMATION: DNA sequence identical or derived from
      naturally occurring TarA binding site

<400> SEQUENCE: 93
aacataccgt gaggtatgtt                                                  20

<210> SEQ ID NO 94
<211> LENGTH: 22
<212> TYPE: DNA
<213> ORGANISM: Artificial Sequence
<220> FEATURE:
<223> OTHER INFORMATION: DNA sequence identical or derived from
      naturally occurring TarA binding site

<400> SEQUENCE: 94
aaacataccg tgtggtatgt tc                                               22
```

```
<210> SEQ ID NO 95
<211> LENGTH: 21
<212> TYPE: DNA
<213> ORGANISM: Artificial Sequence
<220> FEATURE:
<223> OTHER INFORMATION: DNA sequence identical or derived from
      naturally occurring LacI binding site

<400> SEQUENCE: 95
aattgtgagc ggctcacaat t                                              21
```